United States Patent [19]

Kellogg et al.

[11] 4,397,783

[45] Aug. 9, 1983

[54] PROCESS FOR CONVERTING 6,6-DISUBSTITUTED PENICILLANIC ACID DERIVATIVES TO THE 6-β-CONGENERS

[75] Inventors: Michael S. Kellogg, Waterford; Ernest S. Hamanaka, Groton, both of Conn.

[73] Assignee: Pfizer Inc., New York, N.Y.

[21] Appl. No.: 96,832

[22] Filed: Nov. 23, 1979

Related U.S. Application Data

[63] Continuation-in-part of Ser. No. 17,809, Mar. 5, 1979, abandoned.

[51] Int. Cl.$^3$ ............................................ C07D 499/04
[52] U.S. Cl. .......................... 260/245.2 R; 260/239.1; 424/270; 424/246
[58] Field of Search ................... 260/245.2 R; 424/270

[56]  References Cited

U.S. PATENT DOCUMENTS 4,180,506 12/1979 Pratt .............................. 260/245.2
4,203,992  5/1980 Gorden et al. ..................... 424/271

Primary Examiner—Nicholas S. Rizzo
Attorney, Agent, or Firm—Connolly and Hutz

[57]  ABSTRACT

6-β-Substituted penicillanic acids and derivatives thereof as useful enhancers of the effectiveness of several β-lactam antibiotics against many β-lactamase producing bacteria, and 6-β-substituted penicillanic acid derivatives wherein the carboxy group is protected by a conventional penicillin carboxy protecting group as useful intermediates leading to said synergistic agents. A process for converting 6,6-disubstituted penicillanic acid derivatives to the corresponding 6-β-substituted penicillanic acid congeners.

18 Claims, No Drawings

PROCESS FOR CONVERTING 6,6-DISUBSTITUTED PENICILLANIC ACID DERIVATIVES TO THE 6-β-CONGENERS

CROSS-REFERENCE TO RELATED APPLICATION

This application is a continuation-in-part of application Ser. No. 17,809, filed Mar. 5, 1979, and now abandoned.

BACKGROUND OF THE INVENTION

One of the most well-known and widely used class of antibacterial agents are the so-called β-lactam antibiotics. These compounds are characterized in that they have a nucleus consisting of a 2-azetidinone (β-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the β-lactam antibiotics as valuable chemotherapeutic agents, they suffer from the major drawback that certain members are not active against certain microorganisms. It is thought that in many instances this resistance of a particular microorganism to a given β-lactam antibiotic results because the microorganism produces a β-lactamase. The latter substances are enzymes which cleave the β-lactam ring of penicillins and cephalosporins to give products which are devoid of antibacterial activity. However, certain substances have the ability to inhibit β-lactamases, and when a β-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a β-lactamase inhibiting substance and a β-lactam antibiotic is significantly greater than the sum of the antibacterial activities of the individual components.

The present invention relates to a series of 6-β-substituted penicillanic acids and readily hydrolyzable in vivo esters thereof which are potent inhibitors of microbial β-lactamases and enhance the effectiveness of β-lactam antibiotics. The invention further relates to 6-β-substituted penicillanic acid esters wherein said ester portion is a penicillin carboxy protecting group, said esters being useful chemical intermediates to the corresponding acids.

The invention also relates to a process for the preparation of the 6-β-substituted penicillanic acids, their readily hydrolyzable in vivo esters and esters thereof wherein said ester portion is a penicillin carboxy protecting group.

Pharmaceutical compositions comprising the above-mentioned 6-β-substituted penicillanic acids and hydrolyzable esters with certain β-lactam antibiotics as well as a method for increasing the effectiveness of certain β-lactam antibiotics in combination with the above-mentioned 6-β-substituted penicillanic acids and hydrolyzable esters are also parts of the present invention.

6-Substituted penicillanic acids and certain esters have been prepared through 6-diazopenicillanic acid (Helv. Chim. Acta., 50, 1327 (1967), but the orientation of the substituent is in the α-position. 6-α-Hydroxypenicillanic acid is also prepared from 6-diazopenicillanic acid and esters thereof (J. Org. Chem., 39, 1444 (1974).

6-α-Benzyloxypenicillanic acid methyl ester is reported by Manhas, et al., J. Heterocycl. Chem., 15. 601 (1978).

Certain 6,6-dihalo- and 6-halopenicillanic acids are reported by Harrision, et al., J. Chem. Soc., 1772 (1977). In each instance of a mono substituted penicillanic acid the 6-α epimer is described.

More recently Loosemore, et al., J. Org. Chem., 43, 3611 (1978) reported that treatment of a 6-α-bromopenicillanic acid with base epimerized a portion of the compound to give a mixture of 6-α- and 6-β-bromopenicillanic acid which was comprised of about 12% of the β-epimer. A similar mixture was achieved through a hydrogenation of 6,6-dibromopenicillanic acid in which the β-epimer comprised about 30% of the total. It was also shown by Pratt, et al., Proc. Natl. Acad. Sci., 75, 4145 (1978) that the β-lactamase inhibitory characteristic of a mixture of 6-α- and 6-β-bromopenicillanic acid was related to the amount of 6-β-bromopenicillanic acid in said mixture. The findings of Pratt, et al., are corroborated by Knott-Hunziker, et al., Biochem. J., 177, 365 (1979) by the demonstration that a mixture of 5% 6-β-bromopenicillanic acid and 95% 6-α-bromopenicillanic acid inhibits β-lactamase while the α-epimer alone is essentially inactive.

U.S. Pat. No. 4,093,625 claims the preparation of 6-β-mercaptopenicillanic acid and derivatives thereof as antibacterial agents.

Cartwright et al., Nature 278, 360 (1979) reports that while 6α-chloropenicillanic is a poor inhibitor of β-lactamase, the corresponding sulfone is a moderately good inhibitor.

Roets, et al., J. Chem. Soc., (Perkin I) 704 (1976) identifies benzyl 6β-chloropenicillanate as a by-product in the reduction of benzyl 6-oxopenicillanate following hydrochloric acid treatment of the product.

Recently John, et al., J. Chem. Soc. Chem. Comm., 345 (1979) reported the preparation of benzyl 6β-bromopenicillanate from benzyl 6,6-dibromopenicillanate using a tin hydride reduction.

SUMMARY OF THE INVENTION

The 6-β-substituted penicillanic acids of this invention are of the formula

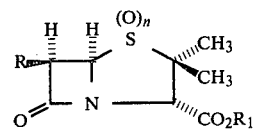

or a pharmaceutically acceptable base salt thereof wherein R is fluoro, chloro, iodo, fluoromethyl, chloro methyl, bromomethyl, alkoxy of one to four carbon atoms or alkylthio of one to four carbon atoms; n is an integer of 0 to 2; and $R_1$ is hydrogen, ester-forming residues readily hydrolyzable in vivo or penicillin carboxy protecting groups, with the proviso that when R is said alkylthio, chloro or iodo n is an integer of from 0 to 1.

A preferred group of β-lactamase inhibitors are those wherein n is 0 and $R_1$ is hydrogen. Within this group those compounds wherein R is chloro or iodo are especially preferred.

A second group of preferred compounds are those wherein n is 1 and $R_1$ is hydrogen. Especially preferred within this group are compounds where R is chloro or iodo.

A third group of compounds which are preferred are those where n is 0 and $R_1$ is a penicillin carboxy protecting group, said group consisting of (a) —$PR_2R_3$ where $R_2$ and $R_3$ are each alkyl of one to three carbon atoms, alkoxy of one to three carbon atoms or phenyl;

(b) 3,5-di-t-butyl-4-hydroxybenzyl;

(c) —$CH_2$—Y where Y is —$C(O)R_4$ wherein $R_4$ is phenyl or alkyl of one to three carbon atoms, cyano or carboalkoxy of two to four carbon atoms;

(d) —N=$CHR_5$ where $R_5$ is phenyl or alkyl of one to three carbon atoms;

(e) —$CH(COCH_3)CO_2R_6$ is alkyl of one to four carbon atoms;

(f) —$CR_7R_8R_9$ where $R_7$ and $R_8$ are each hydrogen, phenyl or methyl and $R_9$ is phenyl, 4-methoxyphenyl, or methyl with the proviso that when $R_7$ and $R_8$ are each methyl, $R_9$ is methyl, and when $R_7$ and $R_8$ are each hydrogen and $R_9$ is phenyl R is fluoro, iodo, fluoromethyl, chloromethyl, bromomethyl, alkoxy of one to four carbon atoms or alkylthio of one to four carbon atoms;

(g) —$Si(CH_3)_3$ and —$Si(CH_3)_2t$—$C_4H_9$;

(h) —$SnR_{16}R_{17}R_{18}$ where $R_{16}$ and $R_{17}$ and $R_{18}$ are each alkyl of one to five carbon atoms, phenyl or benzyl. Especially preferred within this group are those compounds wherein $R_1$ is tri-n-butyltin and R is chloro, wherein $R_1$ is trimethylsilyl and R is chloro, and wherein $R_1$ is 4-methoxybenzyl and R is iodo.

A fourth group of preferred compounds are those wherein $R_1$ is an ester-forming residue readily hydrolyzable in vivo, said group consisting of alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl and γ-butyrolacton-4-yl. Especially preferred within this group are those compounds wherein R is chloro, $R_1$ is pivaloyloxymethyl and n is 0, and wherein $R_1$ is pivaloyloxymethyl, R is iodo and n is 0.

The present invention also relates to a pharmaceutical compound useful for treating bacterial infections in mammals comprising a pharmaceutically-acceptable carrier, a β-lactam antibiotic and a compound of the formula

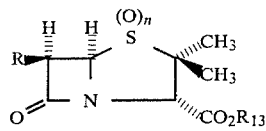

or a pharmaceutically acceptable base salt thereof, where R is fluoro, chloro, iodo, fluoromethyl, chloromethyl, bromomethyl, alkoxy of one to four carbon atoms or alkylthio of one to four carbon atoms; n is an integer of 0 to 2; and $R_{13}$ is hydrogen or an ester-forming residue readily hydrolyzable in vivo, with the proviso that when R is alkylthio n is an integer of 0 to 1.

Preferred within this group of compounds are those wherein $R_{13}$ is hydrogen or an ester-forming residue readily hydrolyzable in vivo selected from alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, and γ-butyrolacton-4-yl and n is 0, and said β-lactam antibiotics are selected from penicillins and cephalosporins. Especially preferred are compounds wherein R is chloro or iodo and $R_{13}$ is hydrogen and wherein R is iodo or chloro and $R_{13}$ is pivaloyloxymethyl.

This invention also consists of a method for increasing the effectiveness of a β-lactam antibiotic in a mammalian subject which comprises co-administration to said subject a β-lactam antibiotic effectiveness increasing amount of a compound of the formula

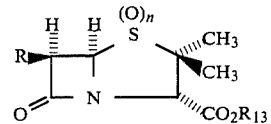

or a pharmaceutically-acceptable base salt thereof wherein R, n and $R_{13}$ are as previously defined. Preferred within this invention are compounds where n is 0 and $R_{13}$ is hydrogen or an ester-forming residue readily hydrolyzable in vivo as previously defined and said β-lactam antibiotics are selected from penicillins and cephalosporins. Especially preferred within this method are compounds wherein $R_{13}$ is hydrogen and R is chloro or iodo and $R_{13}$ is pivaloyloxymethyl and R is iodo or chloro.

Also part of the present invention are compounds of the formula

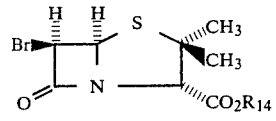

substantially free of the 6-α-bromo epimer, or a pharmaceutically-acceptable base salt thereof, where $R_{14}$ is hydrogen, ester-forming residues readily hydrolyzable in vivo or penicillin carboxy protecting groups. Especially preferred are the crystalline free acid wherein $R_{14}$ is hydrogen and the crystalline sodium salt thereof.

A preferred group of compounds are those wherein $R_{14}$ is a penicillin carboxy protecting group consisting of (a) —$PR_2R_3$ where $R_2$ and $R_3$ are each alkyl of one to three carbon atoms, alkoxy of one to three carbon atoms or phenyl;

(b) 3,5-di-t-butyl-4-hydroxybenzyl;

(c) —$CH_2$—Y where Y is —$C(O)R_4$ wherein $R_4$ is phenyl or alkyl of one to three carbon atoms, cyano or carboalkoxy of two to four carbon atoms;

(d) —N=CHR₅ where R₅ is phenyl or alkyl of one to three carbon atoms;

(e) —CH(COCH₃)CO₂R₆ where R₆ is alkyl of one to four carbon atoms.

(f) —CR₇R₈R₉ where R₇ and R₈ are each hydrogen, phenyl or methyl and R₉ is phenyl, 4-methoxyphenyl, or methyl with the proviso that when R₇ and R₈ are each methyl, R₉ is methyl;

(g) —Si(CH₃)₃ and —Si(CH₃)₂t—C₄H₉;

(h) —SnR₁₆R₁₇R₁₈ where R₁₆ and R₁₇ and R₁₈ are each alkyl of one to five carbon atoms, phenyl or benzyl. Especially preferred within this group are those compounds wherein R₁₄ is tri-n-butyltin and wherein R₁₄ is trimethylsilyl.

A second group of preferred compounds are those wherein R₁₄ is an ester-forming residue readily hydrolyzable in vivo, said group consisting of alkanoyloxymethyl of three to six carbon atoms, 1-(alkanoyloxy)ethyl of four to seven carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl and γ-butyrolacton-4-yl. Especially preferred within this group is the compound wherein R₁₄ is pivaloyloxymethyl.

Also inclusive within the present invention is a pharmaceutical composition for treating bacterial infections in mammals comprising a phramaceutically-acceptable carrier, a β-lactam antibiotic and a compound of the formula

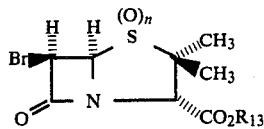

substantially free of the 6-α-bromo epimer, or a pharmaceutically-acceptable base salt thereof, wherein R₁₃ is selected from the group consisting of hydrogen and ester-forming residues readily hydrolyzable in vivo and n is an integer of 0 to 2.

Preferred within the group of compounds are those wherein R₁₃ is hydrogen or an ester-forming residue readily hydrolyzable in vivo selected from alkanoyloxymethyl of three to six carbon atoms, 1-(alkanoyloxy)ethyl of four to seven carbon atoms, 1-methyl-1-(alkanoyloxy)-ethyl of five to eight carbon atoms, alkoxycarbonyloxy-methyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, and γ-butyrolacton-4-yl and n is 0, and said β-lactam antibiotics are selected from penicillins and cephalosporins. Especially preferred is the compound wherein R₁₃ is hydrogen and n is 0 and the sodium salt thereof.

This invention also includes method for increasing the effectiveness of a β-lactam antibiotic in a mammalian subject which comprises co-administration to said subject a β-lactam antibiotic compound of the formula

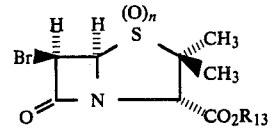

substantially free of the 6-α-bromo epimer, or a pharmaceutically-acceptable base salt thereof, wherein n and R₁₃ are as previously defined. Preferred within this invention are compounds where n is 0 and R₁₃ is hydrogen or an ester-forming residue readily hydrolyzable in vivo as previously defined and said β-lactam antibiotics are selected from penicillins and cephalosporins. Especially preferred within this method are compounds wherein R₁₃ is hydrogen and wherein R₁₃ is pivaloyloxymethyl.

The present invention also includes a process for preparing a compound of the formula

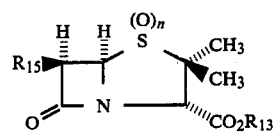

where R₁₅ is fluoro, chloro, bromo, iodo, alkoxy of one to four carbon atoms or alkylthio of one to four carbon atoms; n is 0 to 2, and R₁₃ is hydrogen or ester-forming residues readily hydrolyzable in vivo, which comprises reacting a compound of the formula

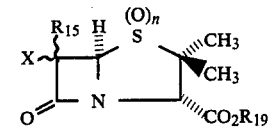

where X is chloro, bromo or iodo; and R₁₉ is ester-forming residues readily hydrolyzable in vivo or conventional penicillin carboxy protecting groups, which an organotin monohydride at about 0°–110° C., followed by removal of R₁₉ when it is a conventional penicillin carboxy protecting group, with the proviso that when R₁₉ is a conventional penicillin carboxy protecting group n is 0 to 1.

A preferred feature of the present process is the use of an organotin monohydride of the formula

where R₁₆, R₁₇ and R₁₈ are each alkyl of one to five carbon atoms, phenyl or benzyl.

A further preferred feature of this process is the use of compounds where R₁₉ is a conventional penicillin carboxy protecting group selected from (a) —PR₂R₃ where R₂ and R₃ are each alkyl of one to three carbon atoms, alkoxy of one to three carbon atoms or phenyl;

(b) 3,5-di-t-butyl-4-hydroxybenzyl;

(c) —CH₂—Y where Y is —C(O)R₄ wherein R₄ is phenyl or alkyl of one to three carbon atoms, cyano or carboalkoxy of two to four carbon atoms;

(d) —N=CHR₅ where R₅ is phenyl or alkyl of one to three carbon atoms;

(e) —CH(COCH₃)CO₂R₆ wherein R₆ is alkyl of one to four carbon atoms;

(f) —CR$_7$R$_8$R$_9$ where R$_7$ and R$_8$ are each hydrogen, phenyl or methyl and R$_9$ is phenyl, 4-methoxyphenyl, or methyl with the proviso that when R$_7$ and R$_8$ are each methyl, R$_9$ is methyl;

(g) —Si(CH$_3$)$_3$ and —Si(CH$_3$)$_2$t—C$_4$H$_9$;

(h) —SnR$_{16}$R$_{17}$R$_{18}$ where R$_{16}$, R$_{17}$ and R$_{18}$ are each alkyl of one to five carbon atoms, phenyl or benzyl;

Especially preferred is the process wherein R$_{19}$ is a conventional penicillin carboxy protecting group —SnR$_{16}$R$_{17}$R$_{18}$ wherein R$_{16}$, R$_{17}$ and R$_{18}$ are each n-butyl, R$_{15}$ and X are each bromo, n is o and the organo-tin monohydride is tri-n-butyltin hydride, said protecting group being removed by aqueous hydrolysis. Also especially preferred is the process wherein R$_{19}$ is a conventional penicillin carboxy protecting group —SnR$_{16}$R$_{17}$R$_{18}$ where R$_{16}$, R$_{17}$ and R$_{18}$ are each n-butyl, R$_{15}$ is chloro, X is iodo, n is 0 and the organotin monohydride is tri-n-butyltin hydride, said protecting group being removed by aqueous hydrolysis. Expecially preferred is the process wherein R$_{19}$ is a conventional penicillin carboxy protecting group —Si(CH$_3$)$_3$, R$_{15}$ and X are each bromo or wherein R$_{15}$ is chloro and X is iodo, n is 0 and the organotin monohydride is tri-n-butyltin hydride, said protecting group being removed by aqueous hydrolysis. Also especially preferred is the process wherein R$_{19}$ is a conventional penicillin carboxy protecting group —CR$_7$R$_8$R$_9$ wherein R$_7$ and R$_8$ are each hydrogen and R$_9$ is 4-methoxyphenyl, R$_{15}$ and X are each iodo, n is 0 and the organotin monohydride is tri-n-butyltin hydride, said protecting group being removed by hydrolysis.

An additional preferred feature of this process is the use of compounds where R$_{19}$ is an ester-forming residue readily hydrolyzable in vivo selected from alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gammabutyrolacton-4-yl. Especially preferred is the process wherein R$_{19}$ is pivaloyloxymethyl, R$_{15}$ and X are each bromo, n is 0 and the organotin monohydride is triphenyltin hydride, the process wherein R$_{19}$ is pivaloxymethyl, R$_{15}$ is chloro and X is iodo n is 0 and the organotin monohydride is tri-n-butyltin hydride and the process wherein R$_{19}$ is pivaloyloxymethyl, R$_{15}$ and X are each iodo, n is 0 and the organotin monohydride is tri-n-butyltin hydride.

The process of the present invention is unique in that it allows for the synthesis of a wide variety of 6-$\beta$-penicillanic acids and derivatives thereof substantially free of the corresponding 6-$\alpha$-epimer, and gives 6-substituted penicillanic acids which are comprised of at least 75% of the $\beta$-epimer. In many instances the content of the desired $\beta$-epimer is as high as 99.5%. Since the $\alpha$-epimer is essentially inactive as a $\beta$-lactamase inhibitor, it is essential for this utility that the products have as high a $\beta$-epimer content as possible. Products containing large amounts of the $\alpha$-epimer must be used in larger doses to achieve inhibition of the $\beta$-lactamase enzymes and potentiation of the $\beta$-lactam antibiotics. The larger doses of these materials may lead to toxicity problems for the mammalian host.

DETAILED DESCRIPTION OF THE INVENTION

Most of the biologically active compounds of the present invention are prepared by the process of the instant invention which is depicted in the following scheme:

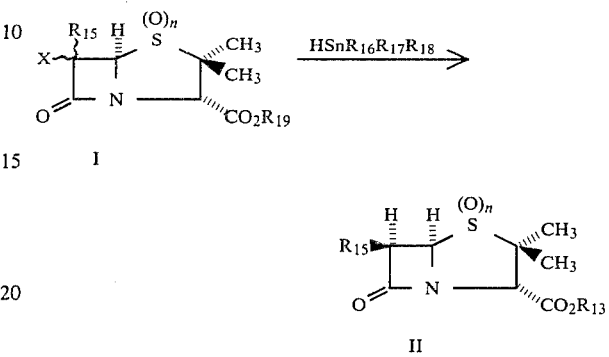

wherein X, R$_{15}$, n, R$_{19}$, R$_{16}$, R$_{17}$, R$_{18}$ and R$_{13}$ are as previously defined.

In general, the reduction can be carried out neat, without the use of a solvent or can be conducted in a solvent provided that said solvent is a reaction-inert solvent which appreciably solubilizes the reactant without reacting to any great extent with the reactants or the product under reaction conditions. When a solvent is employed, it is preferred that said solvent be an aprotic solvent, immiscible with water and with a boiling and freezing point compatible with reaction temperatures. Such solvents or mixtures thereof include aromatic solvents such as benzene or toluene.

When the aforementioned reaction is conducted without a solvent the reactants are mixed thoroughly and heated to the prescribed reaction temperature.

The molar ratio of the starting penicillanic acid derivative and the organotin monohydride is not critical to the claimed process. The use of a slight excess of the tin hydride, up to as much as ten percent above an equimolar quantity, aids in the completion of the reaction and offers no serious problem in isolating the desired product in purified form.

Reaction time is inherently depenedent on concentration, reaction temperature and reactivity of the starting reagents. When the present process is conducted without a solvent a reaction temperature of 60°–100° C. is employed. Under these temperature conditions the reaction is usually complete in 5–8 hours. When a solvent is employed a reaction temperature of 80°–100° C. is used, the reaction requiring 4–6 hours for completion.

The reaction time and temperature can be markedly reduced by carrying out the process under ultraviolet irradiation. Under these conditions the reaction is indicated with a free radical initiator, such as azobisisobutyronitrile, and conducted under cooling such that the temperature is maintained at about 15°–25° C. The reaction time under these conditions is about 15 minutes to several hours.

The preferred reaction temperatures are those which allow the reaction to proceed at a practical rate without resulting in thermal degradation of the starting reagents or products of said process. Accordingly, temperatures of 0°–100° C. are operable.

While the order of addition of the reactants is not critical, it is preferred that the organotin monohydride be added to the 6,6-disubstituted penicillanic acid derivative. In this preferred manner the bis dehalogenation when a 6,6-dihalopenicillanic acid derivative is employed is reduced to a minimum.

In the compounds of the aforementioned formulae, the broken line attachment of a substituent to the bicyclic penicillanic acid nucleus indicates that the substituent is below the plane of said nucleus, and is said to be in the α-configuration. Solid line attachment of a substituent to said nucleus indicates that the substituent is attached above the plane, and is referred to as the β-configuration. The wavy line is intended to denote the two epimers or mixtures thereof.

The organotin monohydrides used as reactants in the present process are prepared by methods known to those skilled in the art. Those which are not available commercially can be prepared by the methods as taught by Hayashi, et al., *J. Organometal. Chem.*, 10, 81(1967).

Those biologically active compounds of the present invention not synthesized by the aforemention process of the instant invention are prepared according to the following scheme:

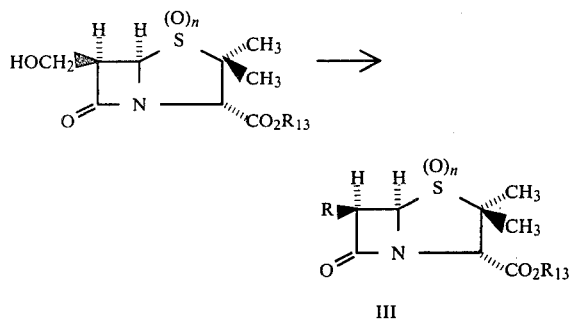

wherein $R_{13}$ is a penicillin carboxy protecting group, n is as previously defined and R is fluoromethyl, chloromethyl or bromomethyl.

Following the above reaction, the carboxy protecting group can be removed to provide for those compounds wherein $R_1$ is hydrogen.

The 6β-hydroxymethyl substituent is replaced by fluoromethyl through a reaction with the fluorinating agent diethylaminosulfurtrifluoride. The reaction is conducted in a reaction-inert-solvent which does not react appreciably with the reactants or product under reaction conditions. Such solvents are preferred to be aprotic solvents which can solubilize the starting reagents, are immiscible with water and have boiling and freezing points compatible with reaction conditions. Such solvents include chlorinated hydrocarbons such as methylene chloride.

Equimolar amounts of the fluorinating reagent and penicillanate are usually employed along with two moles of a tertiary amine, such as pyridine.

The preferred reaction temperatures are those which allow the reaction to proceed at a practical rate. Accordingly, temperatures of −50° to −78° C. are operable.

The reaction time is inherently dependent on concentration, reaction temperature and reactivity of the starting reagents. When the reaction is conducted at −78° C. it is usually substantially complete after 45–60 minutes.

After completion water is added to quench the reaction, and the product is subsequently isolated from the organic phase and purified, if necessary, by chromatography on silica gel.

Preparation of compounds of formula III wherein R is chloromethyl or bromomethyl are effected by treating the requisite 6β-hydroxymethylpenicillanate with triphenylphosphine and carbon tetrachloride or carbon tetrabromide, respectively.

Experimentally, one mole of the penicillanate is reacted with two moles of triphenylphosphine in an excess of the appropriate carbon tetrahalide. In instances where it is not desired to use the carbon tetrahalide as the solvent and reactant, a co-solvent can be employed. It is preferred that the co-solvent be miscible with the carbon tetrahalide and be inert toward reactions with either the starting reagent or the product of the reaction. A preferred co-solvent is methylene chloride.

The preferred reaction temperature is about 0°–5° C., with a corresponding reaction time of about 1–3 hours.

Upon completion of the reaction the product, which can be isolated by removal of the solvent or precipitation of the product by the addition of a solvent in which the product has little or no solubility, is purified, if necessary, by chromatography on silica gel.

The synthesis of compounds of formula III are not carried out on the free acids, but on compounds wherein the carboxy group is modified with a penicillin carboxy protecting as hereinbefore mentioned.

In addition the reaction of 6,6-disubstituted penicillanic acids to the corresponding 6-β-substituted compounds is not carried out on the free acids, but is also conducted with a derivative of said acid as defined by $R_{19}$. These types of derivatives at the 3-carboxy group of the penicillanic acid are known to those skilled in the art and are relatively easy to prepare. Subsequent to the process of the present invention certain of these derivatives, i.e. those which are conventional penicillin carboxy protecting groups, can be removed from the carboxy moiety and provide for the generation of the free acid of formula II (wherein $R_{13}$ is hydrogen). As one skilled in the art can readily appreciate, the removal of a specific protecting group must be compatible with the reactivity of the substituent at the 6-β-position. Accordingly, the removal of a benzyl protecting group from a penicillanic acid containing a 6-β-halo or halomethyl substituent by hydrogenolysis may provide a lower than optimum yield of the desired product because of the tendency of halogens to dehalogenate under such reaction conditions.

The first of these conventional penicillin carboxy protecting groups is the phosphine ester. Following the procedure of West German application No. 2,218,209, the appropriate 6β-hydroxymethyl or 6,6-disubstituted penicillanic acid, as a triethylamine salt, is reacted with a dialkyl- or dialkoxy-chlorophosphine to yield a desired starting reagent for the instant process. On completion of the reaction of said reagent with a halogenating agent or an organotin monohydride, the protecting group is removed from the 6-β-substituted penicillin by addition of water to provide those products wherein $R_{13}$ is hydrogen.

The second protecting group is the 3,5-di-t-butyl-4-hydroxybenzyl ester. This is conveniently prepared from the requisite 6β-hydroxymethyl or 6,6-disubstituted penicillanic acid following the procedure of West German application No. 2,033,493, which comprises reacting the aforementioned penicillanic acid, as a triethylamine salt, with ethyl chloroformate and the subsequent reaction of the resultant mixed anhydride with 3,5-di-t-butyl-4-hydroxybenzyl alcohol. Subsequent to the reaction of the starting reagent with a halogenating reagent or an organotin monohydride by the present process, the protecting group is removed by aqueous hydrolysis at pH 8.0.

The third type of protecting group suitable in the process of the present invention are those where $R_{19}$ is —$CH_2Y$ wherein Y is previously defined. These 6β-hydroxymethyl and 6,6-disubstituted penicillanic acid esters are prepared by alkylation of the corresponding penicillanic acid triethylamine salt with the appropriate halide following the procedure as taught in *Acta. Chem. Scand.*, 21, 2210(1967). Following the reaction of the aforementioned reagent with a halogenating reagent or an organotin monohydride, the protecting group is removed, preferrably, with potassium thiophenoxide.

The fourth type of protecting group in this series, wherein $R_{19}$ is —$N=CHR_5$ and where $R_5$ is as previously defined, is incorporated into the 6β-hydroxymethyl or 6,6-disubstituted penicillanic acid following the procedure taught in *J. Chem. Soc.*, 1917 (1971c), which comprises reacting the mixed anhydride, formed from the requisite 6β-hydroxymethyl or 6,6-disubstituted penicillanic acid and ethyl chloroformate, with the appropriate aldehyde oxime. Subsequent to the reaction of 6β-hydroxymethyl compounds with a halogenating agent or the 6,6-disubstituted compounds with tin hydride in the present process, the protecting group is removed from the 6-β-substituted penicillanic acid by treatment with potassium thiophenoxide.

The fifth type of protecting group is an ester derived from acetoacetic acid esters. Methods for introducing this type of protecting group onto a penicillin carboxy group are described by Ishimaru, et al. *Chemistry Letters*, 1313 and 1317(1977) and comprise the treatment of the sodium salt of a 6β-hydroxymethyl or 6,6-disubstituted penicillanic acid with an appropriate alkyl α-haloacetoacetate. Following the reaction of this product with a halogenating reagent or an organotin monohydride, the protecting group is removed from the 6-β-penicillanic derivative by treatment with an aqueous solution of sodium nitrite.

The sixth type of protecting group where $R_{19}$ is —$CR_7R_8R_9$ can be prepared by a number of routes, the details of which are all represented in the chemical literature. The preferred synthesis comprises starting with known 6-β-aminopenicillanic acid esters followed by replacement of the 6-amino moiety through the 6-diazo group as taught, for example, by Cama, et al., *J. Am. Chem. Soc.*, 94, 1408 (1972) and Harrison, et al., *J. Chem. Soc.* (Perkin I), 1772 (1976). Following the reaction of the 6,6-disubstituted penicillanic acid having the 3-carboxy group a conventional penicillin carboxy protecting group with an organotin monohydride, the protecting group is removed. When two or more of the substituents $R_7$, $R_8$ and $R_9$ are phenyl or if $R_9$ is 4-methoxyphenyl or if $R_7$, $R_8$ and $R_9$ are each methyl, the protecting group can be removed by treatment with trifluoroacetic acid. This method of removal is compatible with all possible substituents at the 6-β position. When $R_7$ or $R_8$ is methyl or $R_7$ and $R_8$ are hydrogen and $R_9$ is phenyl said protecting groups can be removed by treatment with trimethylsilyl iodide as taught by Jung, et al., *J. Am. Chem. Soc.*, 99, 968(1977); alternately these groups can be removed by hydrogenolysis provided that the 6-β-substituent is not a halogen or an alkylthio moiety.

The preparation of the requisite 6β-hydroxymethylpenicillanates can be carried out by reaction of the corresponding 6β-hydroxymethylpenicillanic acid as an activated anhydride with the appropriate alcohol $HOR_7R_8R_9$ or by the alkylation of a salt of said acid with $R_7R_8R_9C$-halide. Following the treatment of the 6β-hydroxymethylpenicillanate with the appropriate halogenating reagent the protecting group is removed as indicated above.

The seventh type of protecting group is a trimethylsilyl or dimethyl-t-butylsilyl ester which is generated in situ through the reaction of a triethylamine salt of a 6,6-disubstituted penicillanic acid and appropriate silyl chloride, according to the procedure as taught in *Ann.*, 673, 166(1964). Following the reaction of the protected 6,6-disubstituted penicillanic acid with the organotin monohydride, the protecting group is removed by aqueous hydrolysis.

The eighth protecting group contemplated by the present invention and discussed previously is that wherein $R_{19}$ is —$SnR_{16}R_{17}R_{18}$, and where $R_{16}$, $R_{17}$ and $R_{18}$ are as previously defined. The tin ester protecting group is formed by adding a molar amount of bis(tin)oxide to two moles of the free 6,6-disubstituted penicillanic acid according to *Chem. Inc.* 1025 (1976). On completion of said process, the protecting group is removed by aqueous hydrolysis.

A penicillin carboxy protecting group which is particularly useful in the synthesis of compounds of formula II, wherein $R_{15}$ is said alkylthio, n is 0 or 1 and $R_{13}$ is hydrogen, is trichloroethyl. This group is introduced onto the carboxy group of the appropriate 6,6-disubstituted penicillanic acid using the procedure as taught in West German application No. 1,937,962. Conversion of said disubstituted penicillanic acid trichloroethyl ester to a 6-halo-6-alkylthiopenicillanic acid trichloroethyl ester or sulfoxide following the hereinafter described procedure, followed by treatment with an organotin monohydride results in the preparation of a 6-β-alkylthiopenicillanic acid trichloroethyl ester or sulfoxide. Removal of the protecting trichloroethyl moiety to provide a compound of formula II wherein $R_{13}$ is hydrogen is achieved by treatment with zinc dust in a buffered solution.

As one skilled in the art recognizes, there are numerous, other unmentioned penicillin carboxy protecting grops which are applicable to the operation of the present process for preparing compounds of the aforementioned formula wherein $R_{13}$ is hydrogen. The concept of the use of such protecting groups for the instant process, while not being exhaustively illustrated, is considered within the broad purview of the present invention. The 6-β-substituted penicillanic acid containing conventional penicillin carboxy protecting groups are valuable intermediates leading to the corresponding free acids.

When $R_{13}$ is an ester-forming residue readily hydrolyzable in vivo in a compound of formula II, it is a group which is notionally derived from an alcohol of the formula $R_{13}$—OH, such that the moiety $COOR_{13}$ in such a compound of formula II represents an ester grouping. Moreover, $R_{13}$ is of such a nature that the grouping $COOR_{13}$ is readily cleaved in vivo to liberate a free carboxy group (COOH). That is to say, $R_{13}$ is a group of the type that when a compound of formula II, wherein $R_{13}$ is an ester-forming residue readily hydrolyzed in vivo, is exposed to mammalian blood or tissue, the compound of formula II, wherein $R_{13}$ is hydrogen, is readily produced. The groups $R_{13}$ are known in the penicillin art. In most instances they improve the absorption characteristics of the penicillin compound. Additionally, $R_{13}$ should be of such a nature that it imparts pharmaceutically-acceptable properties to a compound of formula II, and it liberates pharmaceutically-acceptable fragments when cleaved in vivo.

As indicated above, the groups $R_{13}$ are known and are readily identified by those skilled in the penicillin art, as taught in West German application No. 2,517,316. Typical groups for $R_{13}$ are 3-phthalidyl, 4-crotonlactonyl, γ-butyrolacton-4-yl, alkanoyloxyalkyl and alkoxycarbonyloxyalkyl. However, preferred groups for $R_{13}$ are alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonlactonyl and γ-butyrolacton-4-yl.

Compounds of the formula II, wherein $R_{13}$ is an ester-forming residue readily hydrolyzable in vivo, can be prepared directly from the compound of formula II, wherein $R_{13}$ is hydrogen, by esterification. The specific method chosen will depend naturally upon the precise structure of the ester-forming residue, but an appropriate method will be readily selected by one skilled in the art. In the case wherein $R_{13}$ is selected from the group consisting of 3-phthalidyl, 4-crotonolactonyl, γ-butyrolacton-4-yl, alkanoyloxyalkyl and alkoxycarbonyloxyalkyl they can be prepared by alkylation of the compound of formula II, wherein $R_{13}$ is hydrogen, with a 3-phthalidyl halide, a 4-crotonolactonyl halide, a γ-butyrolacton-4-yl halide, an alkanoyloxyalkyl halide or an alkoxycarbonyloxyalkyl halide. The term "halide" is intended to mean derivative of chlorine, bromine and iodine. The reaction is conveniently carried out by dissolving a salt of the compound of formula II, wherein $R_{13}$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salt, and tertiary amine salts, such as triethylamine, N-ethylpiperidine, N,N-dimethylaniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent to an alkali metal iodide. This has the effect of speeding up the reaction. With full regard for the foregoing factors, reaction times of from 1 to about 24 hours are commonly used.

Alternately, compounds of the present invention of formula II wherein $R_{13}$ is an ester-forming residue readily hydrolyzable in vivo can be prepared from compounds of formula I wherein $R_{19}$ is comprised of said ester-forming groups by the process of the present invention.

The starting reagents of formula I wherein $R_{19}$ is an ester-forming residue readily hydrolyzable in vivo selected from the group consisting of 3-phthalidyl, 4-crotonolactonyl, γ-butyrolacton-4-yl, alkanoyloxyalkyl and alkoxycarbonyloxyalkyl can be prepared by alkylation of the compound of formula I wherein $R_{15}$, X and n are as defined and wherein $R_{19}$ is hydrogen with a phthalidyl halide, a crotonolactonyl halide, a γ-butyrolacton-4-yl halide, an alkanoyloxyalkyl halide or an alkoxycarbonyloxyalkyl halide. The reaction is carried out by dissolving a salt of the compound of formula I, wherein $R_{19}$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salt, and tertiary amine salts, such as triethylamine, N-ethylpiperidine, N,N-dimethylaniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halide compound, the iodide reacts faster than the bromide, which in turn reacts faster than the chloride. In fact, it is sometimes advantageous, when utilizing a chloro compound to add up to one molar equivalent of an alkali metal iodide. This has the effect of speeding up the reaction. With full regard for the foregoing factors, reaction times of from about 1 to about 24 hours are commonly used.

An alternate method for preparing the starting reagents for the instant process of formula I wherein $R_{19}$ is said ester-forming residue is by the diazotization of the appropriate 6-β-aminopenicillanic acid ester and the reaction of the resulting diazopenicillanic acid ester to give the desired 6,6-disubstituted penicillanic acid ester as herein-after described.

Compounds of formula I, wherein $R_{19}$, X and n are as defined and $R_{15}$ is said alkylthio, are most conveniently prepared from the corresponding 6,6-dihalopenicillanic acid ester, preferably the 6,6-dibromopenicillanic acid ester. Said 6,6-dihalopenicillanic acid ester is converted to a 6-bromo-6 Grignard derivative by reaction of the 6,6-dihalo compound with about an equimolar amount of t-butyl magnesium chloride in anhydrous tetrahydrofuran at −75° C. The intermediate Grignard is subsequently reacted, without isolation, with a methyl alkylthiosulfonate to give, on hydrolysis and purification, the requisite 6-halo-6-alkylthiopenicillanic acid ester of formula I wherein X and n are as defined, $R_{15}$ is alkylthio and $R_{19}$ is an ester-forming residue readily hydrolyzable in vivo or a protecting group.

Compounds of the instant invention of formula II wherein $R_{15}$ is as defined with the exception of alkylthio and $R_{13}$ is as defined and n is an integer of 1 or 2 can be prepared by the direct oxidation of compounds of formula II wherein $R_{15}$ is as defined with the exception of alkylthio, $R_{13}$ is as defined and n is 0.

When a compound of Formula II as defined above, wherein n is 0, is oxidized to the corresponding compound of the formula II wherein n is 2 using a metal permanganate, the reaction is usually carried out by treating the compound of the formula II with from 1.0 to about 5 molar equivalents of the permanganate, and preferably about 2 molar equivalents of the permanganate, in an appropriate solvent system. An appropriate solvent system is one that does not adversely interact with either the starting materials or the product, and water is commonly used. If desired, a co-solvent which is miscible with water but will not interact with the permanganate, such as tetrahydrofuran, can be added. The reaction is normally carried out at a temperature in the range from about $-20°$ to about $50°$ C., and preferably at about $0°$ C. At about $0°$ C. the reaction is normally substantially complete within a short period, e.g. within one hour. Although the reaction can be carried out under neutral, basic or acid conditions, it is preferable to operate under substantially neutral conditions in order to avoid decomposition of the $\beta$-lactam ring system of the compound of the formula II, Indeed, it is often advantageous to buffer the pH of the reaction medium in the vicinity of neutrality. The product is recovered by conventional techniques. Any excess permanganate is usually decomposed using sodium bisulfite, and the product is isolated by the usual procedure of solvent extraction, preceeded by acidification of the water layer.

When a compound of formula II, as earlier defined, wherein n is 0, is oxidized to the corresponding compound of the formula II wherein n is 2 using an organic peroxy acid, e.g., a peroxycarboxylic acid, the reaction is usually carried out by treating the compound of the formula II with from about 2 to about 4 molar equivalents, and preferably about 2.2 equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from $-20°$ to about $50°$ C., and preferably at about $0°$ C. At about $25°$ C. reaction times of about 2 to about 16 hours are commonly used. The product is normally isolated by removal of the solvent by evaporation in vacuo. The product can be purified by conventional methods, well-known in the art.

Compounds of formula II wherein $R_{15}$ is as defined, with the exception of said alkylthio, $R_{13}$ is hydrogen, and n is 1, can also be prepared by removal of the penicillin carboxy protecting group as defined by $R_{19}$ in those compounds of formula I. It is only required that said protecting group be:
 (i) stable during oxidation of the compounds of formula I wherein $R_{19}$ is said protecting group and $R_{15}$ and X are as defined;
 (ii) removable from the compounds of formula II, using conditions under which the $\beta$-lactam remains substantially intact; and
 (iii) removable from compounds of formula II, using conditions under which epimerization of the $\beta$-substituent is substantially avoided.

Compounds of formula II wherein $R_{15}$ is as defined, with the exception of alkylthio, $R_{13}$ is hydrogen and n is 2 cannot be practically prepared by removal of the penicillanic carboxy protecting group as defined by $R_{19}$. Said compounds, with the exception of those wherein $R_{15}$ is alkylthio, are best prepared by direct oxidation of those congeners wherein $R_{13}$ is hydrogen.

In like manner, oxidation of the compounds discussed above wherein n is 0 to corresponding compounds wherein n is 1 can be carried out in exactly the same manner as described hereinbefore, except that one-half as much oxidant is employed. The sulfoxides as described in the present invention are meant to embrace both the $\alpha$- and $\beta$-epimers and mixtures thereof.

Those compounds of formula II wherein $R_{13}$ is as defined, n is an integer of 1 or 2 and $R_{15}$ is alkylthio cannot practically be formed by direct oxidation of compounds of formula II wherein $R_{13}$ is as defined, n is 0 and $R_{15}$ is alkylthio. Frequently such oxidations lead to mixtures of products which include those oxidized on the alkylthio moiety, and require careful separation and purification of the desired product. For the preparation of said products it is preferred that they are prepared by initial oxidation, under the conditions previously described, of the 6,6-dihalopenicillanic acid and derivatives thereof to provide the corresponding 6,6-dihalopenicillanic acid sulfones or sulfoxides and ester derivatives thereof. The conversion of the resulting sulfones and sulfoxides to the corresponding 6-halo-6-Grignard reagent is carried out by the method previously described, as is the conversion of said Grignard to the appropriate 6-halo-6-alkylthiopenicillanic acid sulfone or sulfoxide and derivatives thereof. The subsequent reaction of these products with an organotin monohydride by the previously described instant process provides the useful products of the present invention.

In a similar manner, preparation of compounds of the formula

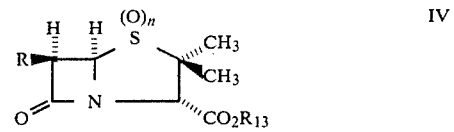

wherein n is as previously defined and $R_{13}$ is as ester-forming residue readily hydrolyzable in vivo and R is fluoromethyl, chloromethyl or bromomethyl are most conveniently prepared by treatment of the appropriate $6\beta$-hydroxymethyl penicillanate ester with the requisite halogenating reagent as previously described. The said $6\beta$-hydroxymethylpenicillanate ester, in turn, is synthesized through the alkylation of the corresponding $6\beta$-hydroxymethylpenicillanic acid, sulfoxide or sulfone in a manner also previously described.

As hereinbefore indicated, compounds of formula IV wherein $R_{13}$ is an ester-forming residue readily hydrolyzable in vivo are converted in vivo into compounds wherein $R_{13}$ is hydrogen as follows:

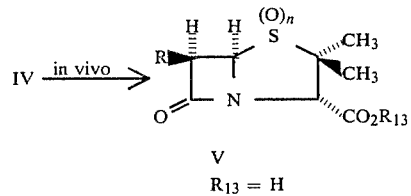

R, n = as previously indicated.

The compounds of formulae II and V wherein $R_{13}$ is hydrogen, are acidic and will form salts with basic agents. Such salts are considered to be within the scope of this invention. These salts can be prepared by standard techniques, such as contacting the acidic and basic components usually in a 1:1 molar ratio, in an aqueous, non-aqueous or partially aqueous medium as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formulae II and V wherein $R_{13}$ is hydrogen are the sodium, potassium and triethylamine salts.

As indicated hereinbefore, the compounds of formulae II and V, wherein $R_{13}$ is hydrogen or an ester-forming residue readily hydrolyzable in vivo, are potent inhibitors of microbial β-lactamases, and they increase the antibacterial effectiveness of β-lactam antibiotics (penicillins and cephalosporins) against many microorganisms, particularly those which produce a β-lactamase. The manner in which the said compounds of formula II and V increase the effectiveness of a β-lactam antibiotic can be appreciated by reference to experiments in which the MIC of a given antibiotic alone, and a compound of formulae II or V alone, are measured. These MIC's are then compared with the MIC values obtained with a combination of the given antibiotic and the compound of formulae II or V. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of formulae II, IV and V wherein $R_{13}$ is hydrogen or an ester-forming residue readily hydrolyzable in vivo, enhance the antibacterial effectiveness of β-lactam antibiotics in vivo. That is, they lower the amount of the antibiotic which is needed to protect mice against an otherwise lethal inoculum of certain β-lactamase producing bacteria.

The ability of the compounds of formulae II IV or V, wherein $R_{13}$ is hydrogen or an ester-forming residue readily hydrolyzable in vivo, to enhance the effectiveness of a β-lactam antibiotic against β-lactamase-producing bacteria makes them valuable for co-administration with β-lactam antibiotics in the treatment of bacterial infections in mammals, particularly man. In the treatment of a bacterial infection, the said compound of the formulae II IV or V can be comingled with the β-lactam antibiotic, and the two agents thereby administered simultaneously. Alternatively, the said compound of the formulae II, IV or V can be administered as a separate agent during a course of treatment with a β-lactam antibiotic. In some instances it will be advantageous to pre-dose the subject with the compound of the formulae II, IV or V before initiating treatment with a β-lactam antibiotic.

When using compounds of formulae II, IV or V wherein $R_{13}$ is hydrogen or an ester thereof readily hydrolyzable in vivo to enhance the effectiveness of β-lactam antibiotic, it is administered preferably in formulation with standard pharmaceutical carriers or diluents. A pharmaceutical composition comprising a pharmaceutically-acceptable carrier, a β-lactam antibiotic and a compound of formulae II, IV or V wherein $R_{13}$ is hydrogen or a readily hydrolyzable ester thereof will normally contain from about 5 to about 80 percent of the pharmaceutically acceptable carrier by weight.

When using the compounds of formulae II, IV or V wherein $R_{13}$ is hydrogen or an ester thereof readily hydrolyzable in vivo in combination with another β-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formulae II, IV or V and the β-lactam antibiotic will normally be in the range from about 1:3 to 3:1. Additionally, when using the compounds of formulae II, IV or V in combination with another β-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some case it may be necessary to use dosages outside these limits.

Typical β-lactam antibiotics with which the compounds of formulae II, IV or V and its esters readily hydrolyzable in vivo can be co-administered are:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid
6-(D-2-amino-2-[4-hydroxyphenyl]acetamido)penicillanic acid,
6-(D-2-amino-2-[1,4-cyclohexadienyl]acetamido penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)-penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-2-[3-methylsulfonylimidazolidin-2-one-1-carboxamido]-2-phenylacetamido)penicillanic acid, 6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid
6-(2-[5-indanyloxycarbonyl]-2-phenylacetamido)penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid,
6-(2,2-dimethyl-5-oxo-4-phenyl-1-imidazolidinyl)penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-formyloxy-2-phenylacetamido)-3-(5-[1-methyltetrazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(D-2-amino-2-p-hydroxyphenylacetamido)desacetoxycephalosporanic acid,
7-(2-[4-pyridylthio]acetamido)cephalosporanic acid,
7-(D-2-amino-2[1,4-cyclohexadienyl]acetamido)cephalosporanic acid,
7-(D-2-amino-2-phenylacetamido)cephalosporanic acid,
7-[D-(−)-alpha-(4-ethyl-2,3,-dioxo-1-piperazinecarboxamido)-alpha-(4-hydroxyphenyl)acetamido]-3-[(1-methyl-1,2-3,4-tetrazol-5-yl)thiomethyl]-3-cephem-4-carboxylic acid,
7-(D-2-amino-2-phenylacetamido)-3-chloro-3-cephem-4-carboxylic acid,
7-[2-(2-amino-4-thiazolyl)-2-(methoximino)acetamido]cephalosporanic acid,
[6R,7R-3-carbamoyloxymethyl-7(2Z)-2-methoxyimino(fur-2-yl)acetamido-ceph-3-em-4-carboxylate]
7-[2-(2-aminothiazol-4-yl)acetamido]-3-[([1-2-dimethylaminoethyl])-1H-tetrazol-5-yl]thio)methyl]ceph-3-em-4-carboxylic acid, and a pharmaceutically acceptable salt thereof.

As will be appreciated by one skilled in the art, some of the above β-lactam compounds are effective when administered orally or parenterally, while others are effective only when administered by the parenteral route. When compounds of formulae II, IV or V wherein $R_{13}$ is hydrogen or an ester thereof readily hydrolyzable in vivo is to be used simultaneously (i.e. co-mingled) with a β-lactam antibiotic which is effective only on parenteral administration, a combination formulation suitable for parenteral use will be required. When the compounds of formulae II, IV or V wherein $R_{13}$ is hydrogen or ester thereof is to be used simultaneously (co-mingled) with a β-lactam antibiotic which is effective orally or parenterally, combinations suitable for either oral or parenteral administration can be prepared. Additionally, it is possible to administer preparations of the compounds of formulae II, IV or V orally, while at the same time administering a further β-lactam antibiotic parenterally; and it is also possible to administer preparations of the compounds of formulae II, IV or V parenterally, while at the same time administering the further β-lactam antibiotic orally.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

6-β-Chloropenicillanic Acid

A 2.95 g. sample of sodium 6-chloro-6-iodopenicillanic acid was converted to the free acid, and then it was dissolved in 125 ml. of benzene under nitrogen. To the solution was added 1.08 ml. of triethylamine, and the mixture was cooled to 0°–5° C. To the cooled mixture was then added 0.977 ml. of trimethylsilyl chloride, and the reaction mixture was stirred at 0°–5° C. for 5 min., at 25° C. for 60 min. and at 50° C. for 30 min. The reaction mixture was cooled to 25° C. and the triethylamine hydrochloride was removed by filtration. The filtrate was heated to reflux and 15 mg. of azobisisobutyronitrile, and 2.02 ml. of tri-n-butyltin hydride were added. The refluxing mixture was irradiated with ultraviolet light for 5 min. The solvent was then removed by evaporation in vacuo, and the residue was dissolved in a 1:1 mixture of tetrahydrofuran-water. The pH was adjusted to 7.0 and the tetrahydrofuran was removed by evaporation in vacuo. The aqueous phase was washed with ether, and then an equal volume of ethyl acetate was added. The pH was adjusted to 1.8 and the ethyl acetate layer removed. The aqueous phase was extracted with further ethyl acetate, and then the combined ethyl acetate solutions were dried and evaporated in vacuo. This afforded 980 mg. of 6-β-chloropenicillanic acid.

The above product was dissolved in tetrahydrofuran, and an equal volume of water was added. The pH was adjusted to 6.8, and the tetrahydrofuran was removed by evaporation in vacuo. The aqueous phase remaining was freeze-dried to give 850 mg. of sodium 6-β-chloropenicillanic acid. The NMR spectrum (D$_2$O) showed absorption at 5.70 (d, 1H, J=4 Hz), 5.50 (d, 1H, J=4 Hz), 4.36 (s, 1H), 1.60 (s, 3H) and 1.53 (s, 3H) ppm.

EXAMPLE 2

6-β-Iodopenicillanic Acid

The title compound is prepared by reduction of 6,6-diiodopenicillanic acid, using tri-n-butyltin hydride according to the procedure of Example 1.

EXAMPLE 3

6-β-Fluoropenicillanic Acid

6-Bromo-6-fluoropenicillanic acid benzyl ester

To a solution of 7.7 ml. of hydrogen fluoride-pyridine and 1.11 g. of N-bromosuccinimide in 10 ml. of diethyl ether cooled to −20° C. was added 1.8 g. of 6-diazopenicillanic acid benzyl ester in 10 ml. of tetrahydrofuran and 5 ml. of diethyl ether. The reaction mixture was stirred for 15 min. at −10° C., and was then poured into ice water. The organic layer was separated and the aqueous further extracted with diethyl ether (3×20 ml.). The organic layer and washing were combined, washing successively with a sodium bicarbonate solution and water and dried over sodium sulfate. Removal of the solvent in vacuo gave 1.6 g. of crude 6-Bromo-6-fluoropenicillanic acid benzyl ester.

The intermediate product was purified by chromatographing on 100 g. of silica gel using chloroform as the eluent. Fractions of 10 ml. each were collected, the desired product being contained in fractions 30–45. Removal of the chloroform gave 0.51 g. of the pure intermediate product.

6-β-Fluoropenicillanic acid benzyl ester

To a solution of 310 mg. of 6-bromo-6-fluoropenicillanic acid benzyl ester in 15 ml. of dry benzene maintained under a nitrogen atmosphere was added 5 mg. of azobisisobutyronitrile followed by 0.208 ml. of tri-n-butyltin hydride. The mixture was irradiated with ultraviolet light for 40 min. with external cooling to maintain the temperature at ca. 25° C. Removal of the solvent gave 500 mg. of crude product which was dissolved in 25 ml. of ethyl acetate to which was then added 25 ml. of water and the pH adjusted to 1.8. The organic phase was separated, dried over sodium sulfate and the solvent removed in vacuo to give the desired intermediate after chromatography on silica gel.

6-β-Fluoropenicillanic acid

In a dry flask protected from moisture and air is added 3.1 g. of 6-β-fluoropenicillanic acid benzyl ester in 40 ml. of dry carbon tetrachloride. Two and two-tenths grams of trimethylsilyl iodide is added and the reaction allowed to stir at room temperature 1.5 hrs. A saturated solution (100 ml.) of sodium bicarbonate is added to the reaction mixture and the aqueous phase separated. The separated aqueous phase is washed with diethyl ether and an equal volume of ethyl acetate is added. The pH is adjusted to 1.8 and the organic phase is separated. The aqueous phase is further extracted with ethyl acetate (2×50 ml.) and the ethyl acetate extracts are combined and dried over sodium sulfate. Removal of the solvent in vacuo gives the desired 6-β-fluoropenicillanic acid.

EXAMPLE 4

6-β-Methoxypenicillanic Acid

6-β-Methoxypenicillanic acid benzyl ester

Under anhydrous conditions a mixture, of 660 mg. of 6-bromo-6-methoxypenicillanic acid benzyl ester (J. Am. Chem. Soc., 94, 1408 (1972), 0.468 ml. of tri-n-butyltin hydride and 5 mg. of azobisisobutyronitrile in 25 ml. of benzene was heated to reflux under an atmosphere of nitrogen for 2 hrs. An additional 0.05 ml. of hydride was added and heating continued for an additional hour. The reaction mixture was concentrated to dryness under reduced pressure to give 1.05 g. of the crude product.

The crude product was chromatographed over 75 g. of silica gel using 2 l. of hexane. The eluate was then changed to chloroform and the chromatographing continued. Fractions 68 through 102 (10 ml. each) were combined and concentrated in vacuo to give 500 mg. of product. The NMR spectrum (CDCl$_3$) shows absorption at 1.45 (s, 3H), 1.68 (s, 3H), 3.58 (s, 3H), 4.5 (s, 1H), 4.82 (d, 1H, J=4 Hz), 5.2 (s, 2H), 5.45 (d, 1H, J=4 Hz) and 7.4 (s, 5H) ppm.

6-β-Methoxypenicillanic acid

A solution of 235 mg. of 6-beta-methoxypenicillanic acid benzyl ester in 15 ml. of methanol was added to 235 mg. of prehydrogenated palladium-on-calcium carbonate in 15 ml. of water and the resulting mixture was shaken in a hydrogen atmosphere at an initial pressure of 55 psi. After 4 hrs. the spent catalyst was filtered and the filtrate concentrated. The cake was washed with methanol and water. The methanol was removed in vacuo and the combined water layers were washed with ethyl acetate. The aqueous was freeze dried to give 94 mg. of the desired product as the calcium salt. The NMR spectrum (D$_2$O) showed absorption at 1.5 (s, 3H), 1.6 (s, 3H), 3.45 (s, 3H), 4.18 (s, 1H), 4.94 (d, 1H, J=4 Hz) and 5.45 (d, 1H, J=4 Hz) ppm.

EXAMPLE 5

Employing the procedures of Example 4 and starting with the appropriate 6-bromo-6-alkoxypenicillanic acid ester, the following 6-β-alkoxypenicillanic esters are prepared:

6-β-ethoxypenicillanic acid benzyl ester; 6-β-methoxypenicillanic acid 4-nitrobenzyl ester; 6-β-i-propoxypenicillanic acid benzhydryl ester; 6-β-n-propoxypenicillanic acid benzhydryl ester; 6-β-n-butoxypenicillanic acid trityl ester; 6-β-methoxypenicillanic acid trityl ester; 6-β-ethoxypenicillanic acid trityl ester; and 6-β-s-butoxypenicillanic acid 4-nitrobenzyl ester.

Starting with the above-mentioned 6-β-alkoxypenicillanic acid ester and employing the hydrogenation procedure of Example 4, the following 6-β-alkoxypenicillanic acid calcium salts are prepared:

6-β-methoxypenicillanic acid; 6-β-ethoxypenicillanic acid; 6-β-isopropoxypenicillanic acid; 6-β-n-propoxypenicillanic acid; 6-β-n-butoxypenicillanic acid; 6-β-n-butoxypenicillanic acid; and 6-β-s-butoxypenicillanic acid.

EXAMPLE 6

6-β-Methylthiopenicillanic Acid 6-bromo-6-methylthiopenicillanic acid trichloroethyl ester To 4.9 g. of 6,6-dibromopenicillanic acid trichloroethyl ester in 100 ml. of dry tetrahydrofuran cooled to −75° C. was added 5.12 ml. of 1.95 M solution of t-butyl magnesium chloride in ether over a 3–4 min. period. The reaction mixture was allowed to stir at −75° C. for 20 min. followed by the addition of 1.26 g. of methyl methylthiosulfonate. Stirring in the cold was continued for slightly over one hour, followed by the addition of 1 ml. of acetic acid. The reaction mixture was allowed to warm to room temperature over a 30 min. period. The reaction was concentrated in vacuo and the residue partitioned between water-ethyl acetate (50 ml./50 ml.). The aqueous layer was further extracted with ethyl acetate (50 ml.) and the combined organic extracts were washed once with water and then with a saturated brine solution. The ethyl acetate layer was separated, dried over sodium sulfate and concentrated to a yellow oil.

The residual oil was chromatographed over 500 g. of silica gel using chloroform as the eluate. Fractions 94–130, comprised of 14 ml. each, were combined and concentrated to give 3.0 g. of the desired product as a light yellow oil which solidified on standing, m.p. 103.5°–105° C. The NMR spectrum (CDCL$_3$) showed absorption at 1.55 (s, 3H), 1.7 (s, 3H), 2.4 (s, 3H), 4.6 (s, 1H), 4.8 (s, 2H) and 5.82 (s, 1H) ppm.

6-β-methylthiopenicillanic acid trichloroethyl ester

To a solution of 500 mg. of 6-bromo-6-methylthiopenicillanic acid trichloroethyl ester in 50 ml of benzene under anhydrous conditions and in a nitrogen atmosphere was added 0.29 ml. of tri-n-butyltin hydride. The resulting reaction mixture was heated under reflux for 6 hrs. An additional 0.1 ml. of the tin hydride was added and heating continued overnight. The solvent was removed in vacuo to give the crude product.

The residue material was chromatographed on 100 g. of silica gel and eluted with a mixture of chloroform-methyl acetate (95/5; vol:vol). Fractions comprising 12 ml. each were collected every 0.5 min. Fractions 33–42 were combined and concentrated to give 300 mg. of product. This was rechromatographed on 60 g. of silica gel, 7 ml. fractions being taken every 0.5 min. Fractions 25–34 were combined and the solvent removed under reduced pressure to give 190 mg. of the desired product as an oil. The NMR spectrum showed absorption (CDCl$_3$) at 1.53 (s, 3H), 1.69 (s, 3H), 2.28 (s, 3H), 4.33 and 4.42 (d, 1H), 4.54 (s, 1H), 4.73 (s, 2H) and 5.48 and 5.56 (d, 1H) ppm.

6-β-Methylthiopenicillanic Acid

In a round-bottom flask fitted with stirrer and stopper were combined 1.38 g. of 6-β-methylthiopenicillanic acid trichloroethyl ester in 28 ml. of tetrahydrofuran, 5.6 g. of zinc dust and 5.6 ml. of 1 M potassium hydrogen phosphate. The reaction mixture was allowed to stir for 15 min. The mixture was filtered through super cel and the cake washed (2×20 ml.) with tetrahydrofuran-water (50/50; vol:vol). The washings were combined with the filtrate and the tetrahydrofuran removed in vacuo. The residual oil and water were extracted (2×30 ml.) with ethyl acetate. The ethyl acetate was discarded and the pH of the aqueous layer was adjusted to pH 2.5 and fresh ethyl acetate added. The combined ethyl acetate extracts were washed with a saturated brine solution and dried over sodium sulfate. Removal of the solvent gave 620 mg. of the product as a clear oil. The residue was taken up in 50 ml. of ethyl acetate and treated with 490 mg. of sodium 2-ethylhexanoate in 15 ml. of ethyl acetate. The precipitate which formed was filtered, washed with ether and dried to give 628 mg. of the desired product as its sodium salt. The NMR spectrum shows absorption (DMSO-D$_6$) at 1.43 (s, 3H), 1.52 (s, 3H), 2.17 (s, 3H), 3.86 (s, 1H), 4.48 and 4.55 (d, 1H) and 5.37 and 5.44 (d, 1H) ppm.

EXAMPLE 7

The procedure of Example 6 is repeated starting with 6,6-dibromopenicillanic acid trichloroethyl ester and the appropriate alkyl methylthiosulfonate, to give the following penicillanic acids as their sodium salts:

6-β-ethylthiopenicillanic acid; 6-β-n-propylthiopenicillanic acid; 6-β-i-propylthiopenicillanic acid; 6-β-n-butylthiopenicillanic acid; and 6-β-s-butylthiopenicillanic acid.

EXAMPLE 8

6-β-Methylthiopenicillanic Acid Pivaloyloxymethyl Ester 6-bromo-6-methylthiopenicillanic acid pivaloyloxymethyl ester Under anhydrous conditions and a nitrogen atomsphere, 4.73 g. of 6,6-dibromopenicillanic acid pivaloyloxymethyl ester in 100 ml of dried tetrahydrofuran was cooled to −75° C. and treated with 5.12 ml. of 1.95 M t-butyl magnesium chloride in ether over a period of 3–4 min. The resulting reaction mixture was allowed to stir at −75° C. for an additional 20 min. followed by the addition of 1.26 g. of methyl methylthiosulfonate. After stirring in the cold for 15 min. the reaction mixture was treated with 1 ml. of acetic acid and allowed to warm to room temperature. The solvents were removed in vacuo and the residual crude product partitioned between 50 ml. of ethyl acetate and 50 ml. of water. The aqueous layer was further extracted with ethyl acetate and the organic extracts combined, washed with a saturated brine solution and dried over sodium sulfate. The crude product, 4.6 g., was obtained on removal of the solvent under reduced pressure.

The product was purified by chromatographing on 500 g. of silica gel, using chloroform as the eluate. Fractions containing 14 ml. each were collected every 0.6 min. Fraction 126 through 242 were combined and concentrated in vacuo to give 2.2 g. of the pure product as a light yellow oil which crystallized on standing, m.p. 79°–81° C. The NMR spectrum (CDCl$_3$) showed absorption at 1.24 (s, 9H), 1.45 (s, 3H), 1.68 (s, 3H), 2.40 (s, 3H), 4.5 (s, 1H), 5.8 (s, 1H) and 5.88 (s, 2H) ppm.

6-β-methylthiopenicillanic acid pivaloyloxymethyl ester

A reaction mixture of 2.2 g. of 6-bromo-6-methylthiopenicillanic acid pivaloyloxymethyl ester and 2.64 ml. of tri-n-butyltin hydride in 75 ml. of benzene was heated under reflux under a nitrogen atmosphere and anhydrous conditions overnight.

The solvent was removed in vacuo and the residue chromatographed over 400 g. of silica gel using chloroform-ethyl acetate (95/5; vol:vol.) as the eluent, and collecting 14 ml. fractions every 0.6 min. Fractions 18–21 were combined and concentrated to give 1.6 g. of the product. The product was further purified by rechromatographing over 350 g. of silica gel to give 1.2 g. of the pure product as an oil. The NMR spectrum (CDCl$_3$) showed absorption at 1.2 (s, 9H), 1.5 (s, 3H), 1.63 (s, 3H), 2.26 (s, 3H), 4.3 and 4.4 (d, 1H), 4.4 (s, 1H), 5.42 and 5.5 (d, 1H), and 5.61, 5.71, 5.73 and 5.83 (q, 2H) ppm.

EXAMPLE 9

The procedure of Example 8 is repeated, starting with the appropriate 6,6-dibromopenicillanic acid ester and alkyl methylthiosulfate, to give the following congeners:

6-β-methylthiopenicillanic acid 3-phthalidyl ester; 6-β-methylthiopenicillanic acid 1-(acetoxy)ethyl ester; 6-β-ethylthiopenicillanic acid pivaloyloxymethyl ester; 6-β-ethylthiopenicillanic acid 4-crotonolactonyl ester; 6-β-methylthiopenicillanic acid gamma-butyrolacton-4-ylester; 6-β-n-propylthiopenicillanic acid acetoxymethyl ester; 6-β-n-propylthiopenicillanic acid pivaloyloxymethyl ester; 6-β-i-propylthiopenicillanic acid hexanoyloxymethyl ester; 6-β-i-propylthiopenicillanic acid 1-(isobutyryloxy)ethyl ester; 6-β-n-butylthiopenicillanic acid 1-methyl-1-(acetoxy)ethyl ester; 6-β-n-butylthiopenicillanic acid 1-methyl-1-(hexanoyloxy)ethyl ester; 6-β-s-butylthiopenicillanic acid methoxycarbonyloxymethyl ester; 6-β-s-butylpenicillanic acid propoxycarbonyloxymethyl ester; 6-β-methylthiopenicillanic acid 1-(ethoxycarbonyloxy)ethyl ester; 6-β-ethylthiopenicillanic acid 1-methyl-1-(methoxycarbonyloxy)ethyl ester; and 6-β-methylthiopenicillanic acid 1-methyl-1-(isopropoxycarbonyl)ethyl ester.

EXAMPLE 10

6-β-Iodopenicillanic Acid Pivaloyloxymethyl Ester 6,6-diiodopenicillanic acid pivaloyloxymethyl ester A mixture of 5.94 g. of sodium nitrite in 260 ml. of water and 2.63 g. of 6-β-aminopenicillanic acid pivaloyloxymethyl ester in 260 ml. of methylene chloride was stirred with cooling in an ice bath. p-Toluenesulfonic acid (1.2 g.) was added in three portions over a period of 30 min. and the mixture was allowed to stir for one hour at room temperature. The organic phase was separated and dried over sodium sulfate. Iodine (1.3 g.) was added to the organic phase and the resulting solution allowed to stir at room temperature for 4 hrs. The solution was washed with aqueous sodium thiosulfate, separated and concentrated in vacuo to a low volume. The residue was chromatographed on silica gel using petroleum ether (b.p. 60°–80°) containing an increasing proportion of ethyl acetate as the eluent. The fractions containing the product were combined, dried over sodium sulfate and concentrated under vacuum to dryness to give 1.43 g., m.p. 136°–138° C. The NMR spectrum (CDCl$_3$) showed absorption at 5.79 (bs, 2H), 5.71 (s, 1H), 4.52 (s, 1H), 1.65 (s, 3H), 1.44 (s, 3H) and 1.21 (s, 9H) ppm.

6-β-iodopenicillanic acid pivaloyloxymethyl ester

To a solution of 1.29 g. of 6,6-diiodopenicillanic acid pivaloyloxymethyl ester in 8 ml. of benzene under a nitrogen atmosphere was added 500 mg. of triphenyltin hydride and a few crystals (~10 mg.) of azobisisobutyronitrile, and resulting reaction mixture was warmed to 50° C. for one hour. An additional 500 mg. of hydride and 10 mg. of nitrile were added and the heating continued with stirring for 3 hrs. Column chromatographing on silica gel using petroleum ether (b.p. 6080° C.) with an increasing proportion of methylene chloride as the eluent gave 140 mg. of the desired product, m.p. 73°–77° C. The NMR spectrum (CDCl$_3$) showed absorption at 5.9 (d, AB, J=5.8 Hz), 5.82 (d, AB, J=5.8 Hz), 5.66 (d, 1H, AB, J=4.1 Hz), 5.42 (d, 1H, AB, J=4.1 Hz), 4.59 (s, 1H), 1.71 (s, 3H), 1.50 (s, 3H) and 1.24 (s, 9H) ppm.

EXAMPLE 11

6-β-Iodopenicillanic Acid Benzyl Ester

In a manner similar to Example 10, 6-β-aminopenicillanic acid benzyl ester was converted to 6,6-diiodopenicillanic acid benzyl ester. The NMR spectrum (CDCl$_3$) showed absorption at 7.40 (m, 5H), 5.77 (s, 1H), 5.21 (s, 2H), 4.59 (s, 1H), 1.67 (s, 3H) and 1.37 (s, 3H) ppm.

The isolated 6,6-diiodopenicillanic acid benzyl ester was converted to 6-β-iodopencillanic acid benzyl ester using the appropriate portion of the Example 10 procedure. The NMR spectrum (CDCl$_3$) showed absorption at 7.42 (m, 5H), 5.64 (d, 1H, AB, J=4.0 Hz), 5.42 (d, 1H, AB, J=4.0 Hz), 4.59 (s, 1H), 1.69 (s, 3H), and 1.40 (s, 3H) ppm.

EXAMPLE 12

Starting with the appropriate 6-β-aminopenicillanic acid ester and employing the procedure of Example 10, the following 6-β-iodopenicillanic acid esters are prepared:

6-β-iodopenicillanic acid 3-phthalidyl ester, 6-β-iodopenicillanic acid 1-(acetoxy)ethyl ester; 6-β-iodopenicillanic acid 4-crotonolactonyl ester; 6-β-iodopenicillanic acid γ-butyrolacton-4-yl ester; 6-β-iodopenicillanic acid acetoxymethyl ester; 6-β-iodopenicillanic acid hexanoyloxymethyl ester; 6-β-iodopenicillanic acid 1-(isobutyryloxy)ethyl ester; 6-β-iodopenicillanic acid methoxycarbonyloxymethyl ester; 6-β-iodopenicillanic propoxycarbonyloxymethyl ester; 6-β-iodopenicillanic acid 1-(ethoxycarbonyloxy)ethyl ester; 6-β-iodopenicillanic acid 1-(butoxycarbonyl)ethyl ester; 6-β-iodopenicillanic acid 1-methyl-1-(methoxycarbonyloxy)ethyl ester; and 6-β-iodopenicillanic acid 1-methyl-1-(isopropoxycarbonyl)ether ester.

EXAMPLE 13

6-β-Chloropenicillanic Acid Acetoxymethyl Ester

6-Chloro-6-iodopenicillanic acid acetoxymethyl ester

To a solution of 5.03 g. of 6-chloro-6-iodopenicillanic acid in 50 ml. of acetone and 50 ml. of acetonitrile is added 900 mg. of di-isopropylethylamine followed by 0.7 ml. of acetoxymethyl bromide. The resulting solution is allowed to stir at room temperature for 48 hrs. An additional 0.7 ml. of bromide and 900 mg. of amine are added and the stirring is continued for an additional 48 hrs. The solution is concentrated in vacuo to dryness and the residue suspended in ethyl acetate. The insolubles are filtered and the filtrate washed successively with water, 1 N hydrochloric acid and saturated aqueous sodium bicarbonate solution. The organic phase is dried, and the solvent removed in vacuo. The residual product is chromatographed on silica gel using methylene chloride as the eluent. The fractions containing the desired material are combined and the solvent removed under vacuum.

6-β-Chloropenicillanic acid acetoxymethyl ester

A solution of 833 mg. of 6-chloro-6-iodopenicillanic acid acetoxymethyl ester and 700 mg. of diphenylmethyltin hydride in 20 ml. of toluene is warmed to 80° C. under a nitrogen atmosphere for 4.5 hrs. The solvent is removed in vacuo, and the residue chromatographed on silica gel using methylene chloride as the eluate. Fractions containing the product were combined and concentrated to dryness to give 6-β-chloropenicillanic acid acetoxymethyl ester.

EXAMPLE 14

Employing the procedures of Example 13, and starting with the requisite halide, the following 6-β-chloropenicillanic acid ester are prepared:

6-β-chloropenicillanic acid 3-phthalidyl ester; 6-β-chloropenicillanic acid 1-methyl-1-(isopropoxy)ethyl ester; 6-β-chloropenicillanic acid pivaloyloxymethyl ester; 6-β-chloropenicillanic acid 4-crotonolactonyl ester; 6-β-chloropenicillanic acid 1-methyl-1-(methoxycarbonyloxy)ethyl ester; 6-β-chloropenicillanic acid γ-butyrolactonyl-4-yl ester; 6-β-chloropenicillanic acid hexanoyloxymethyl ester; 6-β-chloropenicillanic acid 1-(butoxycarbonyloxy)ethyl ester; 6-β-chloropenicillanic 1-(isobutyryloxy)ethyl ester; 6-β-chloropenicillanic acid methoxycarbonyloxymethyl ester; and 6-β-chloropenicillanic acid propoxycarbonyloxymethyl ester.

EXAMPLE 15

6-β-Fluoropenicillanic Acid 1-(ethoxycarbonyloxy)ethyl Ester 6-bromo-6-fluoropenicillanic acid 1-(ethoxycarbonyloxy)ethyl ester 6-Diazopenicillanic acid 1-(ethoxycarbonyloxy)ethyl ester (3.7 g.) in 20 ml. of tetrahydrofuran and 10 ml. of diethyl ether is added to a solution of 15.4 ml. of hydrogen fluoride-pyridine and 2.22 g. of N-bromosuccinimide in 20 ml. of diethyl ether cooled to −20° C. The reaction mixture is allowed to stir at −10° C. for 20 min., and is then quenched in ice water. The organic phase is separated and the aqueous layer further extracted with diethyl ether (3×40 ml.). The organic phase and extracts are combined, washed successively with an aqueous sodium bicarbonate solution and water, and dried over sodium sulfate. Removal of the solvent under reduced pressure gave the crude 6-bromo-6-fluoropenicillanic acid 1-(ethoxycarbonyloxy)ethyl ester.

The intermediate product is purified by chromatographing on 200 g. of silica gel using chloroform as the eluate. The fractions containing the desired compounds are combined and the solvent removed in vacuo.

6-β-fluoropenicillanic acid 1-(ethoxycarbonyloxy)ethyl ester

To a solution of 614 mg. of 6-bromo-6-fluoropenicillanic acid 1-(ethoxycarbonyloxy)ethyl ester in 15 ml. of dry toluene under a nitrogen atmosphere is added 7 mg. of azobisisobutyronitrile followed by 0.500 ml. of di-n-butylphenyltin hydride. The reaction mixture is irradiated with ultraviolet light for 70 min. with external cooling to maintain the temperature at about 25° C. The solvent is removed in vacuo and the residue treated with 50 ml. of water. The pH of the mixture is adjusted to 1.8 and the organic phase is separated, dried over sodium sulfate and concentrated to dryness, to give the desired product, which can be further purified by chromatography.

EXAMPLE 16

Starting with the requisite 6-diazopenicillanic acid ester and employing the procedure of Example 15, the following esters are prepared:

6-β-fluoropenicillanic acid methoxycarbonyloxymethyl ester; 6-β-fluoropenicillanic acid pivaloyloxymethyl ester; 6-β-fluoropenicillanic acid 3-phthalidyl ester; 6-β-fluoropenicillanic acid 1-methyl-1-(isopropoxy)ethyl ester; 6-β-fluoropenicillanic acid 4-crotonolactonyl ester; 6-β-fluoropenicillanic acid 1-methyl-1-(methoxycarbonyloxy)ethyl ester; 6-β-fluoropenicillanic acid γ-butyrolactonyl-4-yl ester; 6-β-fluoropenicillanic acid hexanoyloxymethyl ester; 6-β-fluoropenicillanic acid 1-butoxycarbonyloxy)ethyl ester; 6-β-fluoropenicillanic acid 1-(isobutyryloxy)ethyl ester; 6-β-fluoropenicillanic acid propoxycarbonyloxymethyl ester; and 6-β-fluoropenicillanic acid acetoxymethyl ester.

EXAMPLE 17

6-β-Methoxypenicillanic Acid Pivaloyloxymethyl Ester 6-bromo-6-methoxypenicillanic acid pivaloyloxymethyl ester A mixture of 11.88 g. of sodium nitrite in 500 ml. of water and 5.26 g. of 6-β-aminopenicillanic acid pivaloyloxymethyl ester in 500 ml. of methylene chloride is stirred with cooling in an ice bath. p-Toluenesulfonic acid (2.4 g.) is added in three equal portions over a period of 30 min., and the mixture is allowed to stir for one hour at room temperature. The organic phase is separated and dried over sodium sulfate. A solution of 2.21 g. of N-bromoacetamide in 100 ml. of absolute methanol is added over a period of 10 min. to the organic phase at −10° C., and the resulting reaction solution allowed to stir at 0° C. for 2 hrs. The solution is washed with a saturated brine solution, and the organic phase separated, dried over sodium sulfate and concentrated under reduced pressure. The residue is chromatographed on silica gel using benzene containing increasing amounts of ethyl acetate as the eluent. The fractions containing the desired intermediate are combined and concentrated in vacuo to dryness.

6-β-methoxypenicillanic acid pivaloyloxymethyl ester

To a solution of 1.93 g. of 6-bromo-6-methoxypenicillanic acid pivaloyloxymethyl ester in 20 ml. of dry toluene under a nitrogen atmosphere is added 1 g. of dibenzylethyltin hydride and a few crystals of azobisisobutyronitrile, and the resulting reaction mixture is warmed to 50° C. for one hour. An additional 750 mg. of hydride and 10 mg. of nitrile are added and stirring at 50° C. continued for an additional 3 hrs. Column chromatography on silica gel using cyclohexane with increasing proportions of ethyl acetate as the eluent is used to purify the desired product. The fractions containing product are combined and concentrated in vacuo to dryness.

EXAMPLE 18

Employing the procedure of Example 17, and starting with the appropriate 6-β-aminopenicillanic acid ester and requisite alcohol, the following compounds are prepared:

6-β-methoxypenicillanic acid 3-phthalidyl ester; 6-β-ethoxypenicillanic acid 1-(acetoxy)ethyl ester; 6-β-methoxypenicillanic acid acetoxymethyl ester; 6-β-isopropoxypenicillanic acid 4-crotonolactonyl ester; 6-β-n-butoxypenicillanic acid γ-butyrolacton-4-yl ester; 6-β-n-propoxypenicillanic acid hexanoyloxymethyl ester; 6-β-methoxypenicillanic acid hexanoyloxymethyl ester; 6-β-s-butoxypenicillanic acid methoxycarbonyloxymethyl ester; 6-β-ethoxypenicillanic acid ethoxycarbonyloxymethyl ester; 6-β-n-butoxypenicillanic acid 1-(ethoxycarbonyloxy)ethyl ester; 6-β-n-propoxypenicillanic acid 1-(butoxycarbonyl)ethyl ester; 6-β-methoxypenicillanic acid 1-methyl-1-(methoxycarbonyloxy)ethyl ester and 6-β-n-butoxypenicillanic acid 1-methyl-1-(isopropoxycarbonyloxy)ethyl ester.

EXAMPLE 19

6-β-Chloropenicillanic Acid Sulfoxide Sodium Salt

A solution containing 100 mg. of 6-β-chloropenicillanic acid sodium salt and 83 mg. of sodium meta periodate in 5 ml. of water was allowed to stir at room temperature for 90 min. Ethyl acetate was added and the pH of the aqueous adjusted to 1.8 with 6 N hydrochloric acid. The organic phase was separated and the aqueous layer further extracted with ethyl acetate (3×10 ml.). The organic phase and washings were combined, back washed with water and a saturated brine solution and dried over sodium sulate. The solvent was removed in vacuo and the residue free acid dissolved in tetrahydrofuran. An equal volume of water was added and the pH of the resulting solution adjusted to 6.8 with dilute sodium hydroxide solution. The tetrahydrofuran was removed in vacuo and the remaining aqueous solution freeze dried to provide 45 mg. of the sodium salt of the desired product. The NMR spectrum (acetone-D$_6$) of the free acid showed absorption at 5.6 and 5.7 (2 sets of doublets, 1H (3:1), J=4 Hz), 4.92 and 5.3 (2 sets of doublets, 1H, (3:1), J=4 Hz), 4.56 (s, 3H), 1.7 (s, 3H) and 1.3 and 1.36 (2 singlets (3:1)3H)ppm.

EXAMPLE 20

6-β-Chloropenicillanic Acid Sulfone Sodium Salt

To a solution of 150 mg. of 6-β-Chloropenicillanic acid sodium salt in 5 ml. of water at 0°–5° C. was added dropwise a solution of 185 mg. of potassium permanganate and 0.063 ml. of 85% phosphoric acid in 5 ml. of water. The pH was maintained between 6.0 and 6.5 by the careful addition of dilute sodium hydroxide solution. When the permanganate color persists the dropwise addition was stopped. A small amount of sodium bisulfite was added to get rid of the permanganate color. The reaction mixture was passed through super cel and 25 ml. of ethyl acetate was added to the filtrate. The pH was adjusted to 1.8 with 6 N hydrochloride acid and the organic phase separated. The aqueous was further extracted with ethyl acetate (3×10 ml.). The organic phase and washings were combined, back-washed with water and a saturated brine solution and dried over sodium sulfate. Removal of the solvent in vacuo gave 118 mg. of the desired acid.

The acid was dissolved in tetrahydrofuran to which was added an equal volume of water. The pH was adjusted to 6.8 with a dilute sodium hydroxide solution. The tetrahydrofuran was removed in vacuo and the residue freeze dried to give 90 mg. of the sodium salt of the desired product. The NMR spectrum (acetone-D$_6$) of the free acid showed absorption at 5.82 (d, 1H, J=4 Hz), 5.25 (d, 1H, J=4 Hz), 4.54 (s, 1H), 1.65 (s, 3H) and 1.5 (s, 3H) ppm.

EXAMPLE 21

6-β-Chloropenicillanic Acid Sulfone 6-chloro-6-iodopenicillanic sulfone

To a suspension of 3.0 g. of 6-chloro-6-iodopenicillanic acid in a mixture of 25 ml. of methylene chloride and 15 ml. of water was added sufficient 3 N sodium hydroxide solution to give a pH of 7.0. The aqueous phase was separated and the organic layer extracted several times with water. The aqueous phase and the washings were combined, cooled to 5° C., and treated dropwise over a period of 20 min. with a solution comprised of 1.64 g. of potassium permanganate and 0.8 ml. of phosphoric acid in 25 ml. of water. The temperature was maintained at 5°–8° C. and the pH at 5.5–6.0 by the addition of 3 N sodium hydroxide solution.

Ethyl acetate (30 ml.) was added to the reaction and the pH adjusted to 1.5 with 6 N hydrochloric acid. A 10% solution of sodium bisulfite (20 ml.) was added dropwise, the pH being kept below 1.6 with 6 N hydrochloric acid. The layers were separated and the aqueous further extracted with ethyl acetate. The combined ethyl acetate layer and washings were dried over sodium sulfate and concentrated in vacuo to give 2.4 g. of the desired intermediate, m.p. 137°–139° C.

6-β-chloropenicillanic acid sulfone

To a solution of 3.02 g. of 6-chloro-6-iodopenicillanic acid sulfone in 125 ml. of toluene at 0°–5° C. is added, under a nitrogen atmosphere, 1.08 ml. of triethylamine followed by 0.977 ml. of trimethylsilyl chloride. After stirring 5 min. at 0°–5° C., 60 min. at 25° C. and 30 min. at 50° C., the reaction is cooled to 25° C. and the triethylamine hydrochloride removed by filtration. To the resulting filtrate is added 15 mg. of azobisisobutyronitrile, followed by 2.02 ml. of tribenzyltin hydride. The mixture is irradiated with ultraviolet light for 15 min. with external cooling to maintain the temperature at about 20°–25° C. The solvent is removed in vacuo and the residue dissolved in a 1:1 mixture of tetrahydrofuran—water. The pH is adjusted to 7.0 and the tetrahydrofuran removed under reduced pressure. The residual aqueous solution is extracted with diethyl ether followed by the addition of an equal volume of ethyl acetate. The pH is adjusted to 1.8 with 6 N hydrochloric acid and the organic phase separated. The aqueous is further extracted with ethyl acetate and the combined organic layer and washings are concentrated under vacuum to dryness to give the desired product, identical with that from Example 20.

EXAMPLE 22

Starting with an appropriate penicillanic acid and employing the procedure of the indicated Example, the following compounds are prepared:

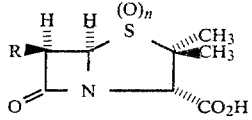

| R | N | Procedure |
|---|---|---|
| I | 1 | Example 19 |
| I | 2 | Example 21 |
| F | 1 | Example 19 |
| F | 2 | Example 20 |
| F | 2 | Example 21 |
| CH$_3$O | 1 | Example 19 |
| CH$_3$O | 2 | Example 21 |
| C$_2$H$_5$O | 1 | Example 19 |
| C$_2$H$_5$O | 2 | Example 20 |
| n-C$_3$H$_7$O | 1 | Example 19 |
| i-C$_3$H$_7$O | 2 | Example 20 |
| i-C$_3$H$_7$O | 2 | Example 21 |
| n-C$_4$H$_9$O | 1 | Example 19 |
| n-C$_4$H$_9$O | 2 | Example 21 |
| s-C$_4$H$_9$O | 1 | Example 19 |

EXAMPLE 23

Pivaloyloxymethyl 6-β-Bromopenicillanate

To a solution of 280 mg. of 6-β-bromopenicillanic acid in 2 ml. of N,N-dimethylformamide is added 260 mg. of diisopropylethylamine followed by 155 mg. of chloromethyl pivalate and 15 mg. of sodium iodide. The reaction mixture is stirred at room temperature for 24 hours, and then it is diluted with ethyl acetate and water. The pH is adjusted to 7.5, and then the ethyl acetate layer is separated and washed three times with water and once with saturated sodium chloride solution. The ethyl acetate solution is then dried using anhydrous sodium sulfate, and evaporated in vacuo to give the title compound.

EXAMPLE 24

Reaction of the appropriate 6-halopenicillanic acid with 3-phthalidyl chloride, 4-crotonolactonyl chloride, gamma-butyrolacton-4-yl chloride or the requisite alkanoyloxymethyl chloride, 1-(alkanoyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Example 23, affords the following compounds:

3-phthalidyl 6-β-chloropenicillanate; 3-phthalidyl-6-β-fluoropenicillanate; 3-phthalidyl 6-β-methoxypenicillanate; 4-crotonolactonyl 6-β-bromopenicillanate; 4-crotonolactonyl 6-β-iodopenicillanate; 4-crotonolactonyl 6-β-ethylthiopenicillanate; γ-butyrolacton-4-yl 6-β-bromopenicillanate; γ-butyrolacton-4-yl 6-β-fluoropenicillanate; γ-butyrolacton-4-yl 6-β-ethoxypenicillanate; acetoxymethyl 6-β-bromopenicillanate; pivaloyloxymethyl 6-β-methylthiopenicillanate; hexanoyloxymethyl 6-β-methylthiopenicillanate; 1-(acetoxy)ethyl 6-β-n-propoxypenicillanate; 1-(isobutyryloxy)ethyl 6-β-chloropenicillanate; 1-methyl-1-(hexanoyloxy)ethyl 6-β-methylthiopenicillanate; methoxycarbonyloxymethyl 6-β-bromopenicillanate; n-propoxycarbonyloxymethyl 6-β-methoxypenicillanate; 1-(ethoxycarbonyloxy)ethyl 6-β-iodopenicillanate; 1-(butoxycarbonyloxy)ethyl 6-β-i-propoxypenicillanate; 1-methyl-1-(ethoxycarbonyloxy)ethyl 6-β-bromopenicillanate and 1-methyl-1-(methoxycarbonyloxy)ethyl 6-β-fluoropenicillanate, respectively.

EXAMPLE 25

6-β-Bromopenicillanic Acid Pivaloyloxymethyl Ester Sulfone 6,6-dibromopenicillanic acid pivaloyloxymethyl ester sulfone To a solution of 1.8 g. of 6,6-dibromopenicillanic acid pivaloyloxymethyl ester in 50 ml. of chloroform was added 1.63 g. of 80% m-chloroperbenzoic acid, and the resulting reaction mixture allowed to stir at room temperature overnight. Water (30 ml.) was added to the reaction and sufficient sodium bisulfite was added to give a negative starch-iodine paper test. The pH was adjusted to 7.5 with dilute sodium hydroxide solution and the organic phase separated. The aqueous was further extracted with chloroform and the organic phase and washings were combined, dried over sodium sulfate and concentrated to dryness. The residue was chromatographed on 250 g. of silica gel using chloroform as the eluent. The fractions containing the product were combined and concentrated to give 1.2 g. of the desired compound.

6-β-bromopenicillanic acid pivaloyloxymethyl ester sulfone

To a solution of 1.15 g. of 6,6-dibromopenicillanic acid pivaloyloxymethyl ester sulfone in 10 ml. of toluene under a nitrogen atmosphere is added 500 mg. of triphenyltin hydride and a few crystals of azobisisobutyronitrile. The resulting reaction mixture is warmed to 40° C. for 30 min. An additional 250 mg. of hydride and small amounts of nitrile are added and the heating continued for an additional 30 min. The solvent is removed in vacuo and the residue treated with 150 ml. of chloroform. The mixture is filtered and the filtrate chromatographed on silica gel using chloroform with increasing proportions of ethyl acetate as the eluent. The fractions containing the product are combined and concentrated in vacuo to give the desired compound.

EXAMPLE 26

6-β-Chloropenicillanic Acid Acetoxymethyl Ester Sulfoxide 6-chloro-6-iodopenicillanic acid acetoxymethyl ester sulfoxide To a solution of 2.1 g. of 6-chloro-6-iodopenicillanic acid acetoxymethyl ester in 55 ml. of chloroform is added 1.06 g. of 80% m-chloroperbenzoic acid and the resulting reaction mixture allowed to stir at room temperature over night. Water (35 ml.) is added and the excess peracid destroyed by the careful addition of sodium bisulfite solution using starch-iodide paper as the indicator. The pH of the aqueous was adjusted to 7.5 and the aqueous separated. The aqueous was extracted (2×10 ml.) with chloroform and is then discarded. The original chloroform layer and washings are combined, washed with a saturated brine solution and dried over sodium sulfate. The residue, after removal of the solvent in vacuo, is dissolved in 60 ml. of chloroform and chromatographed on 250 g. of silica gel using chloroform as the eluent. The fractions containing the product are combined and the solvent removed under reduced pressure.

6-β-chloropenicillanic acid acetoxymethyl ester sulfoxide

Under anhydrous conditions and under a nitrogen atmosphere, 2.63 ml. of tri-n-butyltin hydride is added to a solution of 4.35 g. of 6-chloro-6-iodopenicillanic acid acetoxymethyl ester sulfoxide in 150 ml. of dry toluene, and the resulting reaction mixture allowed to stir at 80° C. for 20 min. Water (50 ml.) is added to the reaction and the organic phase is separated. The organic phase is concentrated in vacuo and the residue dissolved in 75 ml. of chloroform. The resulting solution is chromatographed on 200 g. of silica gel using chloroform as the eluent. The fractions containing the desired product are combined and evaporated to dryness in vacuo.

EXAMPLE 27

Starting with an appropriate 6,6-disubstituted penicillanic acid ester and employing the indicated procedure, the following compounds are synthesized:

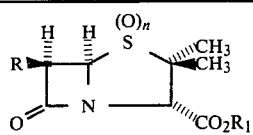

| R | n | Procedure | R$_1$ |
|---|---|---|---|
| Cl— | 2 | Example 25 | —CH$_2$O$_2$CCH$_3$ |
| Br— | 1 | Example 26 | —CH$_2$O$_2$CC(CH$_3$)$_3$ |
| Cl— | 1 | Example 26 | —CH(CH$_3$)O$_2$CCH$_3$ |
| Cl— | 2 | Example 25 | —CH$_2$O$_2$CC(CH$_3$)$_3$ |
| Cl— | 1 | Example 26 | —CH$_2$O$_2$CCH(CH$_3$)$_2$ |
| Cl— | 2 | Example 25 | —CH$_2$O$_2$C(CH$_2$)$_4$CH$_3$ |
| F— | 1 | Example 26 | —CH$_2$O$_2$CCH$_3$ |
| F— | 1 | Example 26 | —CH$_2$O$_2$CC(CH$_3$)$_3$ |
| F— | 2 | Example 25 | —CH(CH$_3$)O$_2$CCH$_3$ |
| F— | 1 | Example 26 | —C(CH$_3$)$_2$O$_2$CCH$_3$ |
| F— | 2 | Example 25 | —CH(CH$_3$)O$_2$C(CH$_2$)$_4$CH$_3$ |
| F— | 2 | Example 25 | —CH$_2$O$_2$CCH$_3$ |
| Br— | 1 | Example 26 | —CH$_2$O$_2$CCH$_3$ |
| Br— | 1 | Example 26 | —CH(CH$_3$)O$_2$CCH$_3$ |
| Br— | 2 | Example 25 | —C(CH$_2$)$_2$O$_2$CCH$_3$ |
| Br— | 2 | Example 25 | —CH$_2$O$_2$C(CH$_2$)$_4$CH$_3$ |
| Br— | 2 | Example 25 | —CH(CH$_3$)O$_2$C(CH$_2$)$_4$CH$_3$ |
| CH$_3$O— | 1 | Example 26 | —CH$_2$O$_2$CCH$_3$ |
| CH$_3$O— | 1 | Example 26 | —CH$_2$O$_2$CC(CH$_3$)$_3$ |
| CH$_3$O— | 2 | Example 25 | —CH(CH$_3$)O$_2$CCH(CH$_3$)$_2$ |
| C$_2$H$_5$O— | 1 | Example 26 | —CH$_2$O$_2$CCH$_3$ |
| C$_2$H$_5$O— | 1 | Example 26 | —CH(CH$_3$)O$_2$CCH$_3$ |
| C$_2$H$_5$O | 2 | Example 25 | —CH$_2$O$_2$CCH(CH$_3$)$_2$ |
| n-C$_3$H$_7$O— | 2 | Example 25 | —CH$_2$O$_2$C(CH$_2$)$_4$CH$_3$ |
| n-C$_3$H$_7$O— | 1 | Example 26 | —CH$_2$O$_2$CC(CH$_3$)$_3$ |
| n-C$_3$H$_7$O— | 1 | Example 26 | —C(CH$_3$)$_2$O$_2$CCH$_3$ |
| i-C$_3$H$_7$O— | 1 | Example 26 | —C(CH$_3$)$_2$O$_2$CCH$_3$ |
| i-C$_3$H$_7$O— | 2 | Example 25 | —C(CH$_3$)$_2$O$_2$CCH$_3$ |
| i-C$_3$H$_7$O— | 1 | Example 26 | —CH$_2$O$_2$CCH(CH$_3$)$_2$ |
| n-C$_4$H$_9$O— | 1 | Example 26 | —CH$_2$O$_2$CCH$_3$ |
| n-C$_4$H$_9$O— | 1 | Example 26 | —CH$_2$O$_2$CC(CH$_3$)$_3$ |
| s-C$_4$H$_9$O— | 1 | Example 26 | —CH$_2$O$_2$CCH$_3$ |
| s-C$_4$H$_9$O— | 2 | Example 25 | —CH$_2$O$_2$CCH$_3$ |
| s-C$_4$H$_9$O— | 1 | Example 26 | —CH$_2$O$_2$CCH$_2$CH$_3$ |
| s-C$_4$H$_9$O— | 1 | Example 26 | —CH(CH$_3$)O$_2$CCH$_3$ |
| I | 1 | Example 26 | —CH$_2$O$_2$CCH$_3$ |
| I | 2 | Example 25 | —CH$_2$O$_2$CC(CH$_3$)$_3$ |
| I | 1 | Example 26 | —CH(CH$_3$)O$_2$CCH$_3$ |
| I | 2 | Example 25 | —C(CH$_3$)$_2$O$_2$CCH$_3$ |
| I | 2 | Example 25 | —CH(CH$_3$)O$_2$CCH(CH$_3$)$_2$ |

EXAMPLE 28

6-β-Methylthiopenicillanic Acid Pivaloyloxymethyl Ester Sulfone 6-bromo-6-methylthiopenicillanic acid pivaloyloxymethyl ester sulfone To 12.37 g. of 6,6-dibromopenicillanic acid pivaloyloxymethyl ester sulfone in 175 ml. of tetrahydrofuran contained in a flask fitted with a stirrer, cold temperature thermometer and nitrogen inlet, and cooled to −75° C. is added 9.4 ml. of a 2.6 M solution of t-butyl magnesium chloride in tetrahydrofuran over a period of 5 min. The reaction mixture is allowed to stir 20 min. at −75° C. and is then treated with 3.09 g. of methyl methylthiosulfonate. Stirring is continued for 3 hrs. at −75° C., one hour at −50° C. and 2 hrs. at 0° C. Acetic acid (3.5 ml.) is added to the reaction mixture and the resulting solution allowed to stir for 15 min. The reaction mixture is then concentrated in vacuo and the residue partitioned between water-ethyl acetate (50 1 ml./50 ml.). The aqueous layer is further extracted with ethyl acetate (50 ml.) and the combined organic extracts are washed once with water and then with a saturated brine solution. The ethyl acetate layer is separated, dried over sodium sulfate and concentrated to give the crude product.

The residual oil is chromatographed on 500 g. of silica gel using chloroform as the eluate. The fractions containing the product are combined and concentrated to give the desired material.

6-β-methylthiopenicillanic acid pivaloyloxymethyl ester sulfone

Under a nitrogen atmosphere and anhydrous conditions a solution of 1.45 g. of 6-bromo-6-methylthiopenicillanic acid pivaloyloxymethyl ester sulfone and 0.81 ml. of tri-n-butyltin hydride in 50 ml. of toluene is heated at 50° C. for 3 hrs. The toluene is removed in vacuo and the residue treated with 25 ml. of ethyl acetate. The desired product crystallized on standing in the cold overnight.

EXAMPLE 29

Employing the procedure of Example 28, and starting with the appropriate penicillanic acid ester, sulfone or sulfoxide and requisite alkyl methylthiosulfonate, the following compounds are prepared:

6-β-methylthiopenicillanic acid 3-phthalidyl ester sulfoxide; 6-β-methylthiopenicillanic acid 1-(acetoxy)ethyl ester sulfone; 6-β-ethylthiopenicillanic acid pivaloyloxymethyl ester sulfone; 6-β-ethylthiopenicillanic acid 4-crotonolactonyl ester sulfoxide; 6-β-methylthiopenicillanic acid γ-butyrolacton-4-yl ester sulfone; 6-β-n-propylthiopencillanic acid acetoxymethyl ester sulfoxide; 6-β-i-propylthiopenicillanic acid hexanoyloxymethyl ester sulfone; 6-β-i-propylthiopenicillanic acid 1-(isobutyryloxy)ethyl ester sulfoxide; 6-β-n-butylthiopenicillanic acid 1-methyl-1-(acetoxy)ethyl ester sulfoxide; 6-β-n-butylthiopenicillanic acid 1-methyl-1-(hexanoyloxymethyl)ethyl ester sulfone; 6-β-s-butylthiopenicillanic acid methoxycarbonyloxy methyl ester sulfone; 6-β-s-butylthiopenicillanic acid propoxycarbonyloxymethyl ester sulfoxide; 6-β-methylthiopenicillanic acid 1-(ethoxycarbonyloxy)ethyl ester sulfoxide; 6-β-ethylthiopenicillanic acid 1-methyl-1-(methoxycarbonyloxy)ethyl ester sulfone;

and 6-β-methylthiopenicillanic acid 1-methyl-1(isopropoxycarbonyloxy)ethyl ester sulfoxide.

EXAMPLE 30

6-β-Bromopenicillanic Acid
1-(Ethoxycarbonyloxy)ethyl Ester Sulfone 6,6-dibromopenicillanic acid
1-(ethoxycarbonyloxy)-ethyl ester sulfone Under a nitrogen atmosphere, 240 mg. of lithium hydroxide was added to 3.91 g. of 6,6-dibromopenicillanic acid sulfone in 30 ml. of dimethylsulfoxide, and the resulting solution allowed to stir at room temperature for 2 hrs. Subsequently, 810 mg. of tetrabutylammonium bromide, 0.56 ml. of N-methylmorpholine and 3.64 g. of α-chlorodiethyl carbonate were added to the reaction mixture in the indicated order, and the reaction mixture allowed to stir at room temperature overnight.

The reaction mixture was poured into 50 ml. of 0.1 N hydrochloric acid and washed with diethyl ether. Removal of the ether gave 2.98 g. of the crude product as a brown oil. A 500 mg. sample was chromatographed on silica gel using ethyl acetate-hexane (1:2; vol:vol) as the eluent to give a sample, 210 mg., of the pure product.

6-β-bromopenicillanic acid 1-(ethoxycarbonyloxy)ethyl ester sulfone

To a solution of 2.53 g. of 6,6-dibromopenicillanic acid 1-(ethoxycarbonyloxy)ethyl ester sulfone in 125 ml. of dry toluene cooled to −5° C. is added 1.82 g. of diphenylbenzyltin hydride followed by 10 mg. of azobisisobutyronitrile. The resulting solution is irradiated with ultraviolet light for 20 min. with external cooling to maintain the temperature at 25° C. The solvent is removed in vacuo and the residue dissolved in a 1:1 mixture of ethyl acetate-water and the pH adjusted to 6.8. The ethyl acetate is separated and the aqueous further extracted with fresh ethyl acetate. The organic phase and the washings are combined, washed with water and a saturated brine solution and dried over sodium sulfate. Removal of the solvent under reduced pressure gives the desired product.

EXAMPLE 31

Starting with an appropriate 6,6-disubstituted penicillanic ester sulfone or sulfoxide, and employing the procedure of Example 30, the following compounds are prepared:

6-β-fluoropenicillanic acid 3-phthalidyl ester sulfoxide; 6-β-fluoropenicillanic acid 4-crotonolactonyl ester sulfoxide; 6-β-fluoropenicillanic acid 1-methyl-1-(methoxycarbonyloxy)ethyl ester sulfone; 6-β-fluoropenicillanic acid 1-(butoxycarbonyloxy)ethyl sulfone; 6-β-fluoropenicillanic acid γ-butyrolacton-4-yl ester sulfoxide; 6-β-chloropenicillanic acid 3-phthalidyl ester sulfoxide; 6-β-chloropenicillanic acid methoxycarbonyloxymethyl ester sulfone; 6-β-chloropenicillanic acid crotonolactonyl ester sulfone; 6-β-chloropenicillanic acid 1-(propoxycarbonyloxy)ethyl ester sulfoxide; 6-β-chloropenicillanic acid 1-methyl-1-(isopropoxycarbonyloxy)ethyl ester sulfoxide; 6-β-chloropenicillanic acid ethoxycarbonyloxymethyl ester sulfone; 6-β-bromopenicillanic acid 1-methyl-1-(propoxycarbonyloxy)ethyl ester sulfone; 6-β-bromopenicillanic acid methoxycarbonyloxymethyl ester sulfoxide; 6-β-bromopenicillanic acid 1-(butoxycarbonyloxy)ethyl ester sulfoxide; 6-β-bromopenicillanic acid 3-phthalidyl ester sulfoxide; 6-β-bromopenicillanic acid γ-butyrolacton-4-yl ester sulfone; 6-β-iodopenicillanic acid 3-phthalidyl ester sulfoxide; 6-β-iodopenicillanic acid 4-crotonolactonyl ester sulfone; 6-β-iodopencillanic acid methoxycarbonyloxymethyl ester sulfoxide; 6-β-iodopenicillanic acid propoxycarbonyloxymethyl ester sulfoxide; 6-β-iodopenicillanic acid 1-(butoxycarbonyloxy)ethyl ester sulfone; 6-β-iodopenicillanic acid 1-methyl-1-(isopropoxycarbonyloxy)ethyl ester sulfoxide; 6-β-methoxypenicillanic acid methoxycarbonyloxymethyl ester sulfoxide; 6-β-methoxypenicillanic acid 1-(ethoxycarbonyloxy)ethyl ester sulfoxide; 6-β-methoxypenicillanic acid 1-methyl-1-(isopropoxycarbonyloxy)ethyl ester sulfoxide; 6-β-ethoxypenicillanic acid γ-butyrolacton-4-yl ester sulfone; 6-β-ethoxypenicillanic acid 3-phthalidyl ester sulfoxide; 6-β-n-propoxypenicillanic acid 1-(propoxycarbonyloxy)ethyl ester sulfoxide; 6-β-i-propoxypenicillanic acid 1-methyl-1-(methoxycarbonyl)ethyl ester sulfone; 6-β-n-butoxypenicillanic acid 3-phthalidyl ester sulfone; 6-β-s-butoxypenicillanic acid ethoxy carbonyloxymethyl ester sulfone; 6-β-n-butoxypenicillanic acid γ-crotonolactonyl ester sulfone; 6-β-n-butoxypenicillanic 1-methyl-1-(butoxycarbonyloxy)ester ester sulfoxide; and 6-β-n-butoxypenicillanic acid 1-methyl-1-(i-propoxycarbonyloxy)ethyl ester sulfoxide.

EXAMPLE 32

6-β-Bromopenicillanic Acid

A mixture of 5.0 g. of 6,6-dibromopenicillanic acid, 1.54 ml. of triethylamine and 100 ml. of benzene was stirred under nitrogen until a solution was obtained. The solution was cooled to 0°–5° C. for 2–3 min., and 1.78 ml. of trimethylsilyl chloride was added. The reaction mixture was stirred at 0°–5° C. for 2–3 min., and then at 50° C. for 35 min. The cooled reaction mixture was filtered and the filtrate was cooled to 0°–5° C. A small quantity of azobisisobutyronitrile was added, followed by 3.68 ml. of tri-n-butyltin hydride. The reaction flask was irradiated with ultraviolet light for 15 min., and then the reaction was stirred at ca. 25° C. for 1.75 hrs. The reaction mixture was irradiated again for 15 min. and then stirring was continued 2.5 hrs. At this point a further small quantity of azobisisobutyronitrile was added, followed by 0.6 ml. of tri-n-butyltin hydride (0.6 ml.) were added and the mixture was again irradiated for 30 min. The solvent was then removed by evaporation in vacuo, and to the residue was added 5% sodium bicarbonate solution and diethyl ether. The two-phase system was shaken vigorously for 10 min. and then the pH was adjusted to 2.0. The ether layer was removed, dried and evaporated in vacuo to give 2.33 g. of an oil. The oil was converted into a sodium salt with sodium bicarbonate followed by freeze drying the solution thus obtained. This afforded sodium 6-β-bromopenicillanic acid, contaminated with a small amount of the alpha-isomer.

The sodium salt was purified by chromatography on Sephadex LH-20. The NMR spectrum (D$_2$O) of the product thus obtained showed absorptions at 5.56 (s, 2H), 4.25 (s, 1H), 1.60 (s, 3H) and 1.50 (s, 3H) ppm.

EXAMPLE 33

6-β-Bromopenicillanic Acid

To 4000 ml. of dry toluene was added 1000 g. of 6,6-dibromopenicillanic acid and 390 ml. of triethylamine and the resulting slurry slowly cooled to 20°–25° C.

Trimethylchlorosilane (355 ml.) was added dropwise over a 10 min. period and the reaction mixture was allowed to warm to 25° C. The triethylamine hydrochloride was filtered and the solids washed with 1.75 l. of toluene. To the combined original filtrate and washings in a flask under a nitrogen atmosphere was added 733 ml. of tri-n-butyltin hydride in 1000 ml. of toluene at the rate of 18–20 ml./min. When the addition was complete, the reaction mixture was allowed to stir for one hour, and was then quenched in 7 l. of a saturated sodium bicarbonate solution. The layers were separated and the organic layer further extracted with an additional 3 l. of the saturated sodium bicarbonate solution. The aqueous layer and extracts were combined, treated with 5 l. of ethyl acetate and treated with sufficient 12 N hydrochloric acid to bring the pH to 1.55. The ethyl acetate layer was separated and the aqueous further extracted with 2.5 l. of ethyl acetate. The original layer and extracts were combined, dried over sodium sulfate and treated with 2.26 l. of an ethyl acetate solution containing an equivalent amount of sodium 2-ethylhexanoate. The precipitate sodium salt was kept at 8°–10° C. overnight and was then filtered and dried to give 391.5 g. of crystalline material.

The above sodium salt (380 g.) was dissolved in 1.9 l. of deionized water at 8° C. and was then treated with sufficient 6 N hydrochloric acid to give a pH of 1.5. After one hour of stirring in the cold (3°–5° C.) the precipitated free acid was filtered and washed with 500 ml. of cold water. To the water-wet free acid in 2 l. of ethyl acetate at 8° C. was added 100 ml. water and the pH adjusted to 1.5 with 6 N hydrochloric acid. The organic layer was separated and the aqueous further extracted with ethyl acetate. The organic layer and the extracts were combined treated with charcoal and dried over magnesium sulfate. To the stirred ethyl acetate is added about one equivalent of sodium 2-ethylhexanoate in 811 ml. of ethyl acetate. After 1.25 hrs. of stirring the precipitated solids were filtered and dried to give 262 g. of sodium 6-β-bromopenicillanate.

To further purify the compound, the above sodium salt was dissolved in 1300 ml. of deionized water and the pH adjusted to 1.3 at 6°–8° C. The precipitated solids were stirred for 1.5 hrs. at 6°–8° C. and were filtered and washed with 300 ml. water. The free acid was treated with 2 l. of ethyl acetate and 200 ml. of water, and the pH adjusted with 6 N hydrochloric acid to 1.35–1.40. The organic layer was separated and dried over magnesium sulfate. To the filtrate was added 802 ml. of ethyl acetate containing about an equivalent of sodium 2-ethylhexanoate. The precipitated sodium salt was allowed to stir for one hour at room temperature and was filtered and dried to give 227 g. of the desired crystalline sodium salt.

A 40.0 g. sample of the above sodium salt was added to 200 ml. of water and the resulting solution at icebath temperature was treated with 6 N hydrochloric acid to pH 1.6. The precipitated free acid was filtered, reslurried twice in water. Drying in vacuo at room temperature overnight gave 34.05 g. of the desired crystalline compound, m.p. 190°–195° C. (dec.).

Anal. Calc'd for $C_8H_{10}NO_3SBr$: C, 34.3; H, 3.6; N, 5.0. Found: C, 34.4; H, 3.7; N, 5.0; $[\alpha]_D = +292°$.

EXAMPLE 34

6-β-Bromopenicillanic Acid Sulfoxide Sodium Salt

To 255 mg. of sodium 6-β-bromopenicillanate in 5 ml. of water was added 182 mg. of sodium periodate and the resulting solution allowed to stir at room temperature for 3 hrs. Ethyl acetate 30 ml. was added to the reaction solution and sufficient 6 N hydrochloric acid added to adjust the pH to 1.3. The ethyl acetate layer was separated, backwashed with a saturated brine solution and dried over magnesium sulfate. The solvent was removed in vacuo and the residual product subsequently dissolved in water containing one equivalent of sodium bicarbonate. Freeze drying of the aqueous solution gave 235 mg. of the desired product as a sodium salt.

EXAMPLE 35

6-β-Bromopenicillanic Acid Sulfone Sodium Salt

To a solution of 255 mg. of sodium 6-β-bromopenicillanate in 5 ml. of water was added 140 mg. of potassium permanganate and 0.11 ml. of phosphoric acid in 3 ml. of water while maintaining the pH at 6.0–6.4 by the careful addition of aqueous sodium hydroxide. The reaction mixture was allowed to stir at 0°–5° C. for 15–20 min. and was then treated with 50 ml. of ethyl acetate. The pH was adjusted to 1.5 with 6 N hydrochloric acid and 330 mg. of sodium bisulfite was added in one portion. The pH was adjusted to 1.7 and the ethyl acetate layer separated and back washed with a saturated brine solution. Removal of the solvent in vacuo gave the product as an oil, 216 mg.

The free acid suspended in 10 ml. of ethyl acetate was added to 10 ml. of water containing 57 mg. of sodium bicarbonate. The aqueous layer was separated and freeze dried to give 140 mg. of the desired compound as the sodium salt.

EXAMPLE 36

6-β-Bromopenicillanic Acid Sulfone Sodium Salt 6-bromo-6-iodopenicillanic acid

To 10 ml. of 2.5 N sulfuric acid, 6.21 g. of iodine-bromide and 2.76 g. of sodium nitrite in 75 ml. of methylene chloride cooled to 0° to −5° C. was added 4.32 g. of 6-β-aminopenicillanic acid over a period of 15 min. After 20 min. stirring at −5° C., 100 ml. of 10% sodium bisulfite was added, care being taken to keep the temperature of the reaction mixture below 10° C. The layers were separated and the aqueous extracted with methylene chloride (3×50 ml.). The combined organic layer and extracts were washed with a saturated brine solution, dried over magnesium sulfate and concentrated in vacuo to give 5.78 of the desired intermedite, m.p. 145°–147° C.

6-bromo-6-iodopenicillanic acid sulfone

To 4.05 g. of 6-bromo-6-iodopenicillanic acid in 30 ml. of methylene chloride and over-laid with 60 ml. of water was added sufficient 3 N sodium hydroxide to give a pH of 7.0. The aqueous layer was separated, cooled to 5° C. and treated dropwise over a 15 min. period with 1.93 g. of potassium permanganate and 1 ml. of 85% phosphoric acid in 30 ml. of water. The pH was maintained at 5.8–6.2 by the addition of 3 N sodium hydroxide and the temperature was kept at about 5° C. On completion of the addition, 100 ml. of ethyl acetate was added and the pH lowered to 1.5 with 6 N hydrochloric acid. A 10% sodium bisulfite solution (30 ml.) was added until the reaction mixture turned a pale yellow. The organic layer was separated and the aqeuous extracted with ethyl acetate (4×50 ml.). The organic layer and extracts were combined, washed with a saturated brine solution, dried over magnesium sulfate and concentrated under reduced pressure to give 3.6 g., m.p. 151°–153° C.

6-β-bromopenicillanic acid sulfone sodium salt

To a solution of 3.36 g. of 6-bromo-6-iodopenicillanic acid sulfone in 130 ml. of toluene at 5° C. is added, under a nitrogen atmosphere, 1.09 ml. of triethylamine followed by 1.3 g. of dimethyl-t-butylsilyl chloride. Stirring is maintained for 5 min. at 5° C., 60 min. at 25° C. and 30 min. at 45° C., and then the reaction mixture is cooled to 25° C. The triethylamine hydrochloride is removed by filtration and 15 mg. of azobisisobutyronitrile and 2.04 ml. of dibenzylphenyltin hydride is added to the filtrate. The mixture is irradiated with ultraviolet light for 15 min., with external cooling to keep the temperature at about 20°–25° C. The solvent is removed in vacuo and residual material dissolved in a 1:1 mixture of tetrahydrofuran-water. The pH is adjusted to 7.0 and the tetrahydrofuran removed under reduced pressure. The aqueous is treated with 100 ml. of ethyl acetate and the pH adjusted to 1.8 with 6 N hydrochloric acid. The organic layer is separated and the aqueous further extracted with ethyl acetate. The organic layer and extracts are combined, backwashed with a saturated brine solution and dried over sodium sulfate. The organic solution is then treated with 2.2 g. of sodium 2-ethylhexanoate in ethyl acetate and allowed to stir for 1 hour. The resulting precipitated salt is filtered and dried.

EXAMPLE 37

6-β-Bromopenicillanic Acid Acetoxymethyl Ester 6,6-dibromopenicillanic acid acetoxymethyl ester To a solution of 5 g. of 6,6-dibromopenicillanic acid and 900 mg. of di-isopropylethylamine in 50 ml. of acetone and 50 ml. of acetonitrile was added 0.7 ml. of acetoxymethyl bromide, and the resulting solution allowed to stir at room temperature for 48 hrs. An additional 0.7 ml. of the bromide and 900 mg. of amine were then added and the stirring continued for a further 48 hrs. The solvent was removed in vacuo and the residue treated with ethyl acetate and filtered. The filtrate was washed with water, 1 N hydrochloric acid and saturated aqueous sodium bicarbonate, and was then dried over sodium sulfate. The residue which remained after the solvent was removed under vacuum was chromatographed on silica gel using methylene chloride as the eluent. The fractions containing the desired material were combined and concentrated to give a colorless oil which solidified on standing. Recrystallization of a portion gave the analytical sample, m.p. 79°–82° C. The NMR spectrum (CDCl$_3$) showed absorption at 5.78 (s, 3H), 4.51 (s, 1H), 2.10 (s, 3H), 1.61 (s, 3H) and 1.48 (s, 3H) ppm.

6-β-bromopenicillanic acid acetoxymethyl ester

A mixture of 430 mg. of 6,6-dibromopenicillanic acid acetoxymethyl ester and 350 mg. of triphenyltin hydride was heated under a nitrogen atmosphere to 90° C. for 5 hrs. The residue was chromatographed on 120 g. of silica gel using methylene chloride as the eluent. Fractions containing the product were combined and concentrated in vacuo to give the desired product. The NMR spectrum (CDCl$_3$) showed absorption at 5.81 (s, 2H) 5.65 (s, 2H), 4.51 (s, 1H), 2.05 (s, 3H), 1.65 (s, 3H) and 1.48 (s, 3H) ppm.

EXAMPLE 38

6-β-bromopenicillanic Acid Pivaloyloxymethyl Ester 6,6-dibromopenicillanic acid pivaloyloxymethyl ester To a solution of 1.8 ml. of pivaloyloxymethyl chloride and 5 g. of 6,6-dibromopenicillanic acid in 15 ml. of dimethylformamide at 0° C. was added 1.9 ml. of triethylamine and the resulting reaction mixture allowed to stir at room temperature for 16 hrs. The reaction mixture was poured into 150 ml. of water and 150 ml. of ethyl acetate and the pH adjusted to 2.0 with 6 N hydrochloric acid. The organic phase was washed with water, aqueous sodium bicarbonate solution and a saturated brine solution, and then dried over magnesium sulfate. Removal of the solvent in vacuo gave 4.7 g. of a red solid which was purified by column chromatography, m.p. 98°–99° C. The NMR spectrum (CDCl$_3$) showed absorption at 5.80 (s, 2H), 5.75 (s, 1H), 4.5 (s, 1H), 1.61 (s, 3H), 1.47 (s, 3H) and 1.21 (s, 9H) ppm.

6-β-bromopenicillanic acid pivaloyloxymethyl ester

The reduction procedure employed in Example 37 was used on 6,6-dibromopenicillanic acid pivaloyloxymethyl ester to give the desired product. The NMR of the product showed absorption at 5.85 (d, 1H, J=5 Hz), 5.76 (d, 1H, J=5 Hz), 5.56 (d, 1H, J=4 Hz), 5.31 (d, 1H, J=4 Hz), 4.53 (s, 1H), 1.67 (s, 3H), 1.49 (s, 3H) and 1.22 (s, 9H) ppm.

EXAMPLE 39

Starting with 6,6-dibromopenicillanic acid and the appropriate halide, and employing the procedure of Example 37, the following compounds are prepared:

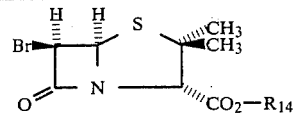

| $R_{14}$ |
| --- |
| —CH(CH$_3$)O$_2$CCH$_3$ |
| —CH$_2$O$_2$CCH(CH$_3$)$_2$ |
| —CH$_2$O$_2$C(CH$_2$)$_4$CH$_3$ |
| —CH(CH$_3$)O$_2$CCH$_3$ |
| —CH(CH$_3$)O$_2$C(CH$_2$)$_4$CH$_3$ |
| —C(CH$_3$)$_2$O$_2$CCH$_3$ |
| —C(CH$_3$)$_2$O$_2$CC(CH$_3$)$_3$ |
| —C$_4$H$_3$O$_2$* |
| —C$_4$H$_5$O$_2$+ |
| —C$_8$H$_5$O$_2$# |
| —CH$_2$O$_2$COCH$_3$ |
| —CH$_2$O$_2$COCH(CH$_3$)$_2$ |
| —CH(CH$_3$)O$_2$CO(CH$_2$)$_3$CH$_3$ |
| —CH(CH$_3$)O$_2$COC$_2$H$_5$ |
| —C(CH$_3$)$_2$O$_2$CO(CH$_2$)$_2$CH$_3$ |

*4-crotonolactonyl
+γ-butyrolacton-4-yl
3-phthalidyl

EXAMPLE 40

6-β-Bromopenicillanic Acid

A. 6,6-dibromopenicillanic acid dimethoxyphosphine ester

To a solution of 3.58 g. of 6,6-dibromopenicillanic acid in 40 ml. of methylene chloride is added 1.08 g. of triethylamine, and the solution is treated with 1.28 g. of dimethoxychlorophosphine and allowed to stir for 30 min. The solvent is removed in vacuo and the residue treated with 125 ml. of dry diethyl ether. The insoluble triethylamine hydrochloride is filtered and the ether removed under reduced pressure to provide the desired intermediate.

B. 6-β-bromopenicillanic acid

To 4.5 g. of 6,6-dibromopenicillanic acid dimethoxyphosphine ester in 150 ml. of dry toluene is added 3.4 g. of di-n-butylphenyltin hydride and the resulting reaction mixture allowed to stir at room temperature for 20 min. A saturated aqueous sodium bicarbonate solution 150 ml. is added to the reaction mixture and the organic phase separated and discarded. The aqueous phase is further extracted with ethyl acetate (2×25 ml.) and the pH is carefully adjusted to 1.5 with 6 N hydrochloric acid. The acidified aqueous layer is extracted (3×50 ml.) with ethyl acetate and the extracts combined, dried over magnesium sulfate and concentrated to give the desired product.

EXAMPLE 41

A. Employing the procedure of Example 40A and starting with the appropriate 6,6-disubstituted penicillanic acid and requisite phosphine chloride, the following compounds are prepared:

6-chloro-6-iodopenicillanic acid diphenylphosphine ester; 6,6-dibromopenicillanic acid di-n-propoxyphosphine ester; 6,6-dibromopenicillanic acid diethylphosphine ester; diiodopenicillanic acid dimethoxyphosphine ester; 6-bromo-6-iodopenicillanic acid diphenylphosphine ester; 6-bromo-6-iodopenicillanic acid di-n-propylphosphine ester; 6-bromo-6-methoxypenicillanic acid dimethylphosphine ester; 6-bromo-6-n-butoxypenicillanic acid dimethoxyphosphine ester; 6-bromo-6-ethoxypenicillanic acid phenylethylphosphine ester; 6-bromo-6-methylthiopenicillanic acid diphenylphosphine ester; 6-bromo-6-i-propylthiopenicillanic acid methylmethoxyphosphine ester; 6-chloro-6-iodopenicillanic acid diethoxyphosphine ester sulfoxide; 6-bromo-6-iodopenicillanic acid di-i-propoxyphosphine ester sulfoxide; 6-bromo-6-methoxypenicillanic acid ethoxyphenylphosphine ester sulfoxide and 6-bromo-6-methylthiopenicillanic acid dimethoxyphosphine ester sulfoxide.

B. Starting with the above compounds, and employing the procedure of Example 40B, affords the following analogs:

6-β-chloropenicillanic acid; 6-β-bromopenicillanic acid; 6-β-iodopenicillanic acid; 6-β-methoxypenicillanic acid; 6-β-n-butoxypenicillanic acid; 6-β-ethoxypenicillanic acid; 6-β-methylthiopenicillanic acid; 6-β-i-propylthiopenicillanic acid, 6-β-chloropenicillanic acid sulfoxide; 6-β-bromopenicillanic acid sulfoxide; 6-β-6-methoxypenicillanic acid sulfoxide and 6-β-methylthiopenicillanic acid sulfoxide.

EXAMPLE 42

6-β-Chloropenicillanic Acid

A. 6-chloro-6-iodopenicillanic acid 3,5-di-t-butyl-4-hydroxybenzyl ester

To a solution of 3.62 g. of 6-chloro-6-iodopenicillanic acid in 200 ml. of dry methylene chloride is added 1.0 g. of triethylamine and the resulting solution cooled to 0°-5° C. Ethyl chloroformate (1.1 g.) is added portionwise to the reaction mixture over a period of 15 min. The reaction is maintained at 0° C. for 30 min. and is then treated with 2.36 g. of 3,5-di-t-butylbenzyl alcohol. After stirring in the cold for 2 hrs. The reaction mixture is allowed to warm to room temperature. Water (75 ml.) is added to the reaction mixture and the organic phase is separated, dried over sodium sulfate and concentrated in vacuo to give the desired compound.

B. 6-β-chloropenicillanic acid

To a solution of 2.9 g. of 6-chloro-6-iodopenicillanic acid 3,5-di-t-butyl-4-hydroxybenzyl ester in 125 ml. of dry toluene under nitrogen is added 10 mg. of azobisisobutyronitrile and 1.5 ml. of tri-n-butylin hydride. The mixture is allowed to stir for 20 min. The solvent is removed under reduced pressure and the residue dissolved in a 1:1 tetrahydrofuran-water mixture to which is then added 1.08 g. of sodium 2-ethylhexanoate in 20 ml. of methanol. After stirring at room temperature for 3 hrs., ethyl acetate is added and the pH adjusted to 7.0. The ethyl acetate layer is separated, fresh ethyl acetate is added to the aqueous and the pH adjusted to 1.5 with 6 N hydrochoric acid. The organic phase is separated, dried over sodium sulfate and concentrated to give the desired product.

EXAMPLE 43

A. Starting with the requisite 6,6-disubstituted penicillanic acid and employing the procedure of Example 42A and B, the following compounds are prepared:

6-β-bromopenicillanic acid; 6-β-iodopenicillanic acid; 6-β-methylthiopenicillanic acid; 6-β-n-butylthiopenicillanic acid; 6-β-chloropenicillanic acid sulfoxide; 6-β-bromopenicillanic acid sulfoxide; and 6-β-methylthiopenicillanic acid sulfoxide.

EXAMPLE 44

6-β-Fluoropenicillanic Acid

A. 6-bromo-6-fluoropenicillanic acid phenacyl ester

To a solution of 2.98 g. of 6-bromo-6-fluoropenicillanic acid and 1.99 g. of phenacyl bromide in 40 ml. of a 1:1 mixture of dry dimethylformamide-tetrahydrofuran cooled to 0° C. is added dropwise over a 14 min. period 1.4 ml. of triethylamine. The cold reaction mixture is stirred for 3 hrs. and is then treated with 100 ml. of ethyl acetate and 100 ml. of a saturated aqueous sodium bicarbonate solution. The aqueous phase is separated and discarded, and fresh water is added to the organic phase. The pH is adjusted to 5.0 with 6 N hydrochloric acid and the organic phase separated, washed with a brine solution, dried over sodium sulfate and concentrated in vacuo to give the desired product.

B. 6-β-fluoropenicillanic acid

A solution of 2.08 g. of 6-bromo-6-fluoropenicillanic acid phenacyl ester in 60 ml. of dry toluene under a nitrogen atmosphere and cooled to 0° C. is treated with 1.59 g. of dibenzylmethyltin hydride and 10 mg. of azobisisobutyronitrile, and the resulting reaction mixture warmed to 50° C. for 5 hrs. The solvent is removed under vacuum and the residue is chromatographed on silica gel using methylene chloride as the eluent. The fractions containing the product are combined and concentrated to dryness.

The residual product is dissolved in 25 ml. of dry dimethylformamide and is treated with 375 mg. of potassium thiophenoxide in 4 ml. of dimethylformamide. After stirring at room temperature for 2 hrs. the reaction mixture is added to 60 ml. of a saturated aqueous sodium bicarbonate solution. Ethyl acetate (60 ml.) is added and the organic phase is separated and fresh ethyl acetate added. The pH of the aqueous phase is adjusted to 1.5 with 6 N hydrochloric acid and the organic phase separated, washed with a saturated brine solution and dried over sodium sulfate. Removal of the solvent in vacuo gives the desired product.

EXAMPLE 45

A.

Starting with the appropriate 6,6-disubstituted penicillanic acid and requisite α-halomethylcarbonyl reagent and employing the procedure of Example 44A, affords the following compounds:

6-bromo-6-fluoropenicillanic acid acetonyl ester; 6-bromo-6-fluoropenicillanic acid propionylmethyl ester; 6,6-dibromopenicillanic acid cyanomethyl ester; 6,6-dibromopenicillanic acid methoxycarbomethyl ester; 6,6-dibromopenicillanic acid phenacyl ester; 6-chloro-6-iodopenicillanic acid phenacyl ester; 6-chloro-6-iodopenicillanic acid acetonyl ester; 6-chloro-6-iodopenicillanic acid propionylmethyl ester; 6-chloro-6-iodopenicillanic acid propoxycarbomethyl ester; 6,6-diiodopenicillanic acid cyanomethyl ester; 6,6-diiodopenicillanic acid i-butyrylmethyl ester; 6,6-diiodopenicillanic acid phenacyl ester; 6-bromo-6-iodopenicillanic acid acetonyl ester; 6-bromo-6-iodopenicillanic acid cyanomethyl ester; 6-bromo-6-methoxypenicillanic acid phenacyl ester; 6-bromo-6-methoxypenicillanic acid propionylmethyl ester; 6-bromo-6-methoxypenicillanic acid ethoxycarbomethyl ester; 6-bromo-6-methylthiopenicillanic acid cyanomethyl ester; 6-bromo-6-methylthiopenicillanic acid phenacyl ester; 6-chloro-6-iodopenicillanic acid n-butyrylmethyl ester sulfoxide; 6,6-dibromopenicillanic acid phenacyl ester sulfoxide; 6,6-diiodopenicillanic acid acetonyl ester sulfoxide; 6-bromo-6-iodopenicillanic acid cyanomethyl ester sulfoxide; and 6-bromo-6-methoxypenicillanic acid methoxycarbomethyl ester sulfoxide.

B. Starting with the esters from Example 45A and employing the procedure of Example 44B, the following congeners are prepared:

6-β-fluoropenicillanic acid; 6-β-bromopenicillanic acid; 6-β-chloropenicillanic acid; 6-β-iodopenicillanic acid; 6-β-methoxypenicillanic acid; 6-β-methylthiopenicillanic acid; 6-β-bromopenicillanic acid sulfoxide; and 6-β-methoxypenicillanic acid sulfoxide.

EXAMPLE 46

6-β-Chloropenicillanic Acid Sulfoxide

A. O-(6-chloro-6-iodopenicillanoyl)benzaldehyde oxime sulfoxide

To a solution of 3.9 g. of 6-chloro-6-iodopenicillanic acid sulfoxide in 200 ml. of methylene chloride is added 1.0 g. of triethylamine and the resulting reaction mixture cooled to 0° C. Ethyl chloroformate (1.1 g.) is added dropwise over a period of 15 min. and the reaction maintained at 0° C. for 30 min. Benzaldehyde oxime (1.2 g.) is added in 10 ml. of dry acetone and the stirring continued for 2 hrs. The reaction mixture is then allowed to warm to room temperature and the stirring is continued for 2 additional hours. The reaction mixture is filtered and the filtrate concentrated to dryness. The residue is distributed between ethyl acetate (100 ml.) and water (50 ml.). The aqueous layer is separated and the organic layer washed with a saturated aqueous sodium bicarbonate solution and is dried over magnesium sulfate. Removal of the solvent in vacuo affords the desired product.

B. 6-β-chloropenicillanic acid sulfoxide

To 2.48 g. of O-(6-chloro-6-iodopenicillanoyl)benzaldehyde oxime sulfoxide in 75 ml. of dry toluene under a nitrogen atmosphere is added 1.62 g. of dibenzyl-n-butyltin hydride and 15 mg. of azobisisobutyronitrile. The resulting reaction mixture is stirred, warmed to 50° C. and maintained at this temperature for 5 hrs. The solvent is removed in vacuo and the residue is partitioned between 100 ml. of ethyl acetate and 75 ml. of water. The organic phase is separated, dried over sodium sulfate and concentrated under reduced pressure to dryness. One and eight tenths grams of the residue is dissolved in 25 ml. of dimethylformamide to which is then added 660 mg. of potassium thiophenoxide in 10 ml. of the same solvent. After stirring for 2 hrs. at room temperature the reaction mixture is added to a saturated sodium bicarbonate solution. The aqueous is extracted with 75 ml. of ethyl acetate and the organic phase separated. The pH of the aqueous is adjusted to 1.5 with 6 N hydrochloric acid and extracted with ethyl acetate. The organic phase is separated, dried over sodium sulfate and concentrated in vacuo to dryness to give the desired product.

EXAMPLE 47

A.

Employing the procedure of Example 46A and starting with the appropriate 6,6-disubstituted penicillanic acid and oxime, the followings compounds are synthesized:

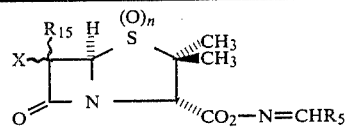

| X   | R$_{15}$ | N | R$_5$ |
| --- | --- | --- | --- |
| Br— | F— | 0 | —C$_6$H$_5$ |
| Br— | F— | 0 | —CH$_3$ |
| Br— | F— | 0 | —i-C$_3$H$_7$ |
| I—  | Cl— | 0 | —C$_2$H$_5$ |
| I—  | Cl— | 0 | —n-C$_3$H$_7$ |
| Br— | Br— | 0 | —C$_6$H$_5$ |
| Br— | Br— | 0 | —C$_2$H$_5$ |
| I—  | I—  | 0 | —CH$_3$ |
| I—  | I—  | 0 | —C$_2$H$_5$ |
| I—  | Br— | 0 | —CH$_3$ |
| I—  | Br— | 0 | —C$_6$H$_5$ |
| Br— | CH$_3$O— | 0 | —C$_6$H$_5$ |
| Br— | CH$_3$S— | 0 | —C$_6$H$_5$ |
| Br— | CH$_3$S— | 0 | —C$_2$H$_5$ |
| Br— | Br— | 1 | —C$_6$H$_5$ |
| Br— | CH$_3$O— | 1 | —C$_6$H$_5$ |
| Br— | F— | 1 | —CH$_3$ |
| Br— | Cl— | 1 | —CH$_3$ |
| Br— | Cl— | 1 | —C$_6$H$_5$ |
| Br— | Cl— | 1 | —C$_6$H$_5$ |
| Br— | Cl— | 1 | —n-C$_3$H$_7$ |

B.

Starting with the esters in Example 47A and utilizing the procedure of Example 46B, the following analogs are prepared:

6-β-fluoropenicillanic acid, 6-β-chloropenicillanic acid, 6-β-bromopenicillanic acid, 6-β-iodopenicillanic acid,; 6-β-methoxypenicillanic acid; 6-β-methylthiopenicillanic acid; 6-β-bromopenicillanic acid sulfoxide; 6-β-methoxypenicillanic acid sulfoxide; 6-β-fluoropenicillanic acid sulfoxide; and 6-β-chloropenicillanic acid sulfoxide.

EXAMPLE 48

6-β-Iodopenicillanic Acid

A. 6,6-diiodopenicillanic acid benzhydryl ester

To a solution of 5.94 g. of sodium nitrite in 250 ml. of water at 5° C. was added with stirring 2.9 g. of 6-β-aminopenicillanic acid benzhydryl ester tosylate salt in 250 ml. of methylene chloride. p-Toluene sulfonic acid (1.2 g.) was added in three portions over a period of 30 min. and the mixture allowed to stir for one hour at room temperature. The organic phase was separated, dried over sodium sulfate and treated with 1.3 g. of iodine. The resulting solution was stirred at room temperature for 4 hrs. and was then washed with an aqueous sodium thiosulfate solution and concentrated to a low volume. The residual was chromatographed on silica gel using petroleum ether with increasing proportions of ethyl acetate as the eluent. The fractions containing the product were combined and concentrated in vacuo to give the desired product.

B. 6-β-iodopenicillanic acid benzhydryl ester

To a solution of 1.92 g. of 6,6-diiodopencillanic acid benzhydryl ester in 8 ml. of benzene was added 500 mg. of triphenyltin hydride and 10 mg. of azobisisobutyronitrile, and the resulting reaction mixture allowed to stir under a nitrogen atmosphere at 50° C. for one hour. An additional amount of hydride (500 mg.) and nitrile (10 mg.) was added and heating at 50° C. continued for 3 hrs. The solvent was removed under vacuum and the residue chromatographed over silica gel using petroleum ether with increasing proportions of ethyl acetate as the eluent. The fractions containing the product were combined and concentrated to dryness. The NMR spectrum ($CDCl_3$) showed absorption at 7.50 (bs, 10H), 6.97 (s, 1H), 5.66 (d, 1H, AB, J=4.0 Hz), 5.44 (d, 1H, AB, J=4.0 Hz), 4.67 (s, 1H), 1.70 (s, 3H) and 1.40 (s, 3H) ppm.

C. 6-β-iodopenicillanic acid

Trifluoroacetic acid (0.5 ml.) was added to 80 mg. of 6-β-iodopenicillanic acid benzhydryl ester in 1 ml. of methylene chloride and the reaction mixture stirred for 30 min. at room temperature. The mixture was evaporated to dryness to yield 76 mg. of crude product. Purification is affected by chromatography on silica gel.

EXAMPLE 49

A.

Starting with the appropriate penicillanic acid ester and employing the procedure of Example 48A, the following compounds are prepared:

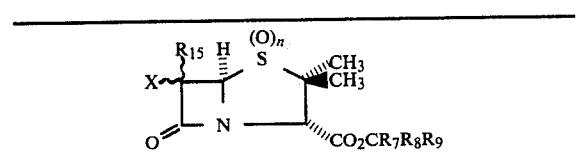

| X | $R_{15}$ | N | $R_7$ | $R_8$ | $R_9$ |
|---|---|---|---|---|---|
| Br— | F— | 0 | H— | $C_6H_5$— | $C_6H_5$— |
| Br— | F— | 0 | $CH_3$— | $C_6H_5$— | $C_6H_5$— |
| Br— | F— | 0 | $C_6H_5$— | $C_6H_5$— | $C_6H_5$— |
| I— | Cl— | 0 | H— | $C_6H_5$— | $C_6H_5$— |
| I— | Cl— | 0 | $CH_3$— | $C_6H_5$— | $C_6H_5$— |
| Br— | Br— | 0 | $C_6H_5$— | $C_6H_5$— | $C_6H_5$— |
| Br— | Br— | 0 | $CH_3$— | $C_6H_5$— | $C_6H_5$— |
| I— | Br— | 0 | $CH_3$— | $C_6H_5$— | $C_6H_5$— |
| Br— | $CH_3O$— | 0 | H— | $C_6H_5$— | $C_6H_5$— |
| Br— | $C_2H_5O$— | 0 | H— | $C_6H_5$— | $C_6H_5$— |
| Br— | $CH_3S$— | 0 | H— | $C_6H_5$— | $C_6H_5$— |
| Br— | Br— | 1 | H— | $C_6H_5$— | $C_6H_5$— |
| Br— | F— | 1 | $CH_3$— | $C_6H_5$— | $C_6H_5$— |
| I— | Cl— | 1 | $CH_3$— | $C_6H_5$— | $C_6H_5$— |
| I— | Cl— | 1 | H— | $C_6H_5$— | $C_6H_5$— |
| Br— | Cl— | 1 | H— | $C_6H_5$— | $C_6H_5$— |
| Br— | Cl— | 1 | H— | $C_6H_5$— | $C_6H_5$— |
| Br— | Cl— | 0 | $C_6H_5$— | $C_6H_5$— | $C_6H_5$— |
| Br— | Cl— | 0 | H— | $C_6H_5$— | $C_6H_5$— |

B.

Following the procedures of Example 48B and C and starting with the esters in Example 49A, affords the following penicillanic acids:

6-β-fluoropenicillanic acid; 6-β-chloropenicillanic acid; 6-β-bromopenicillanic acid; 6-β-methoxypenicillanic acid; 6-β-ethoxypenicillanic acid; 6-β-methylthiopenicillanic acid; 6-β-bromopenicillanic acid sulfoxide; 6-β-fluoropenicillanic acid sulfoxide; and 6-β-chloropenicillanic acid sulfoxide.

EXAMPLE 50

6-β-Iodopenicillanic Acid

A. 6,6-diidopenicillanic acid 4-methoxybenzyl ester

The title compound was prepared from 6-β-aminopenicillanic acid 4-aminopenicillanic acid 4-methoxybenzyl ester following the procedure of Example 48A.

B. 6-β-iodopenicillanic acid 4-methoxybenzyl ester

The title compound was prepared from 6,6-diiodopenicillanic acid 4-methoxybenzyl ester using the procedure of Example 48B. The NMR ($CDCl_3$) spectrum shows absorption at 7.36 (d, 2H, AA', XX', J=9 Hz), 6.95 (d, 2H, AA', XX', J=9.0 Hz), 5.65 (d, 1H, AB, J=4.2 Hz), 5.42 (d, 1H, AB, J=4.2 Hz), 4.58 (s, 1H), 3,89 (s, 3H), 1.71 (s, 3H), 1.70 (s, 3H) and 1.39 (s, 3H) ppm.

C. 6-β-iodopenicillanic acid

6-β-Iodopenicillanic acid 4-methoxybenzyl ester (90 mg.) was dissolved in 2 ml. of methylene chloride to which was then added 1 ml. of trifluoroacetic acid and 3 drops of anisole. The mixture was stirred at room temperature for 5 hrs. and was then evaporated to dryness. The residue was chromatographed on silica using petroleum ether and then ethyl acetate as the eluent. The fractions containing the product were combined and concentrated to give 40 mg. of the desired product. The NMR ($CDCl_3$) spectrum showed absorption ca. 9

(bs, 1H), 5.65 (d, 1H, AB, J4.0 Hz), 5.39 (d, 1H, AB, J=4.0 Hz), 4.57 (s, 2H), 1.74 (s, 3H) and 1.57 (s, 3H).

EXAMPLE 51

A.

Starting with the requisite penicillanic acid ester and employing the procedure of Example 49A, the following compounds are prepared:

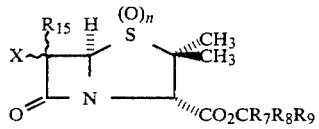

| X | $R_{15}$ | n | $R_7$ | $R_8$ | $R_9$ |
|---|---|---|---|---|---|
| Br— | F— | 0 | H— | H— | 4-CH$_3$OC$_6$H$_4$— |
| Br— | F— | 0 | H— | C$_6$H$_5$— | 4-CH$_3$OC$_6$H$_4$— |
| Br— | F— | 0 | CH$_3$— | CH$_3$— | 4-CH$_3$OC$_6$H$_4$— |
| Br— | F— | 0 | CH$_3$— | CH$_3$— | CH$_3$— |
| I— | Cl— | 0 | H— | CH$_3$— | 4-CH$_3$OC$_6$H$_4$— |
| I— | Cl— | 0 | CH$_3$— | CH$_3$— | 4-CH$_3$OC$_6$H$_4$— |
| Br— | Br— | 0 | CH$_3$— | CH$_3$— | CH$_3$— |
| I— | Br— | 0 | H— | H— | 4-CH$_3$OC$_6$H$_4$— |
| I— | Br— | 0 | H— | CH$_3$— | 4-CH$_3$OC$_6$H$_4$— |
| Br— | CH$_3$S— | 0 | H— | H— | 4-CH$_3$OC$_6$H$_4$— |
| Br— | CH$_3$S— | 0 | CH$_3$— | CH$_3$— | CH$_3$— |
| Br— | C$_2$H$_5$S— | 0 | H— | C$_6$H$_5$— | 4-CH$_3$OC$_6$H$_4$— |
| Br— | Br— | 1 | H— | H— | 4-CH$_3$OC$_6$H$_4$— |
| Br— | F— | 1 | CH$_3$— | CH$_3$— | CH$_3$— |
| Br— | F— | 1 | CH$_3$— | CH$_3$— | 4-CH$_3$OC$_6$H$_4$— |
| I— | Cl— | 1 | H— | H— | 4-CH$_3$OC$_6$H$_4$— |
| I— | Cl— | 1 | H— | CH$_3$— | 4-CH$_3$OC$_6$H$_4$— |
| Br— | CH$_3$S— | 1 | H— | H— | 4-CH$_3$OC$_6$H$_4$— |
| Br— | Cl— | 1 | H— | H— | 4-CH$_3$OC$_6$H$_4$— |
| Br— | Cl— | 1 | CH$_3$— | CH$_3$— | CH$_3$— |
| Br— | Cl— | 0 | H— | C$_6$H$_5$— | 4-CH$_3$OC$_6$H$_4$— |

B.

Starting with compounds in Example 51, and following the procedures of Example 48B and C, affords the following analogs:

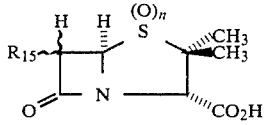

| $R_{15}$ | n |
|---|---|
| F— | 0 |
| Cl— | 0 |
| Br— | 0 |
| CH$_3$S— | 0 |
| C$_2$H$_5$S— | 0 |
| Br— | 1 |
| F— | 1 |
| Cl— | 1 |
| CH$_3$S— | 1 |

EXAMPLE 52

6-β-Bromopenicillanic Acid Sodium Salt

A. 6,6-dibromopenicillanic acid tri-n-butyltin ester

To a slurry of 35.9 g. of 6,6-dibromopenicillanic acid in 700 ml. of toluene was added 29.5 g. of bis(tri-n-butyltin)oxide and the resulting mixture heated to reflux. Over a period of about 45 min. the toluene was allowed to distill from the reaction mixture, water being azeotropically removed during that period of time. The remainder of the solvent was removed at room temperature in vacuo, to give 78.7 g. of the desired intermediate.

B. 6-β-bromopenicillanic acid sodium salt

To 1.0 g. of 6,6-dibromopenicillanic acid tri-n-butyltin ester in 5 ml. of toluene at 55° C. was added 0.4 ml. of tri-n-butyltin hydride dropwise. Heating was continued for 3.5 hrs., after which the solvent was removed and the residue dissolved in 25 ml. of chloroform. The chloroform was washed with a saturated sodium bicarbonate solution (2×50 ml.). The aqueous washes were combined, the pH adjusted to 1.5 with 6 N hydrochloric acid and the product extracted with ethyl acetate. The ethyl acetate extracts were combined, dried over magnesium sulfate and 1.24 ml. (1.24 mmol./CC.) of ethyl acetate containing sodium 2-ethylhexanoate was added. After stirring in the cold for one hour the product was filtered and dried, 114 mg.

EXAMPLE 53

A.

Starting with the appropriate 6,6-disubstituted penicillanic acid and tin oxide, and employing the procedure of Example 52A, the following tin esters are prepared:

6,6-dibromopenicillanic acid triethyltin ester; 6,6-dibromopenicillanic acid triphenyltin ester; 6,6-dibromopenicillanic acid diphenylbenzyltin ester; 6-bromo-6-chloropenicillanic acid triphenyltin ester; 6-bromo-6-chloropenicillanic acid tri-i-propyltin ester; 6-iodo-6-chloropenicillanic acid tri-n-butyltin ester; 6-iodo-6-chloropenicillanic acid dibenzylphenyltin ester; 6,6-diiodopenicillanic acid triphenyltin ester; 6-iodo-6-bromopenicillanic acid triethyltin ester; 6-bromo-6-methylthiopenicillanic acid tri-n-butyltin ester; 6-bromo-6-chloropenicillanic acid tribenzyltin ester sulfoxide; 6,6-dibromopenicillanic acid tri-n-butyltin ester sulfoxide; 6,6-diiodopenicillanic acid tri-n-propyltin ester sulfoxide; and 6-bromo-6-chloropenicillanic acid triphenyltin ester sulfoxide.

B.

Using the reagents of Example 53A and employing the procedure of Example 52B, the following 6-β-substituted penicillanic acids are prepared:

6-β-bromopenicillanic acid; 6-β-chloropenicillanic acid; 6-β-iodopenicillanic acid; 6-β-chloropenicillanic acid sulfoxide; 6-β-bromopenicillanic acid sulfoxide; and 6-β-iodopenicillanic acid sulfoxide.

EXAMPLE 54 6-β-Bromopenicillanic Acid

A. 6,6-dibromopenicillanic acid methyl acetoacetate ester

To 5.0 g. of 6,6-dibromopenicillanic acid sodium salt in 100 ml. of dimethylformamide was added 1.6 ml. of methyl 2-chloroacetoacetate, and the resulting reaction mixture allowed to stir over night at room temperature. The mixture was poured into 400 ml. of ice and water and extracted with ethyl acetate. The organic phase was separated and washed successively with water, a saturated aqueous sodium bicarbonate solution and a brine solution. The organic phase was then dried over magnesium sulfate and concentrated to a dark oil (5.0 g.), which was chromatographed on 300 g. of silica gel. The fractions of eluate, which was comprised of toluene-/ethyl acetate (2:1, V:V), containing the product were combined and concentrated in vacuo to give 4.0 g. of the desired product.

6-β-bromopenicillanic acid

Under anhydrous conditions and a nitrogen atmosphere 2.0 g. of 6,6-dibromopenicillanic acid methyl acetoacetate ester in 140 ml. of dry benzene was treated with 1.1 ml. of tri-n-butyltin hydride, and the resulting reaction mixture allowed to stir over night at room temperature. The benzene solvent was removed in vacuo and the residue slurried in hexane. The undissolved material was chromatographed on 250 g. of silica gel using toluene/ethyl acetate (5:1, V:V) as the eluent. The fractions containing the desired product were combined and concentrated under reduced pressure to dryness.

To 3.9 g. of 6-β-bromopenicillanic acid methyl acetoacetate ester, prepared by the above, procedure, in 50 ml. of acetone is added 2.1 g. of sodium nitrite in 10 ml. of water with stirring. After stirring for 3 hrs. at room temperature the solvent is removed in vacuo and the residue aqueous extracted once with ether. The aqueous is then made acid to pH 1.5 with 6 N hydrochloric and extracted with ethyl acetate. The organic phase is dried over sodium sulfate and concentrated under reduced pressure to give the desired product.

EXAMPLE 55

Employing the procedure of Example 54A, and starting with the requisite 6,6-disubstituted penicillanic acid sodium salts, the following esters are prepared:

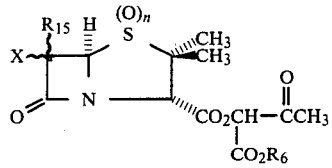

| X   | $R_{15}$  | n | $R_6$      |
|-----|-----------|---|------------|
| I—  | Cl—       | 0 | $CH_3$—    |
| I—  | I—        | 0 | $C_2H_5$—  |
| I—  | Br—       | 0 | $n-C_3H_7$—|
| Br— | $CH_3S$—  | 0 | $CH_3$—    |
| Br— | $C_2H_5S$—| 0 | $C_2H_5$—  |
| I—  | Cl—       | 1 | $CH_3$—    |
| I—  | I—        | 1 | $CH_3$—    |
| Br— | Br—       | 1 | $CH_3$—    |
| Br— | $CH_3S$—  | 1 | $n-C_3H_7$—|

B.

Starting with the esters in Example 55A, and using the procedure of Example 54B, the following compounds are synthesized:

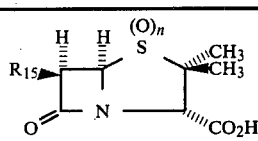

| $R_{15}$   | n |
|------------|---|
| Cl—        | 0 |
| I—         | 0 |
| Br—        | 0 |
| $CH_3S$—   | 0 |
| $C_2H_5S$— | 0 |
| Cl—        | 1 |
| I—         | 1 |
| Br—        | 1 |

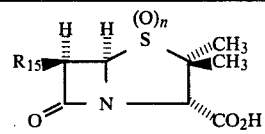

| $R_{15}$ | n |
|----------|---|
| $CH_3S$— | 1 |

EXAMPLE 56

6β-Fluoromethylpenicillanic Acid Sulfone

A. benzyl 6-bromo-6-hydroxymethylpenicillanate

A solution of 44.9 g. of benzyl 6,6-dibromopenicillanate in 600 ml. of dry tetrahydrofuran was cooled to −78° C. and 56.4 ml. of t-butylmagnesium chloride was added dropwise with vigorous stirring under an inert atmosphere while maintaining the temperature at −60° C. After stirring 30 min. at −78° C. the solution was treated with gaseous formaldehyde in a stream of nitrogen until five molar equivalents had been added. The reaction was quenched at −78° C. by the addition of 5.7 ml. of acetic acid dropwise over a period of 25 min. The reaction solution was allowed to warm to room temperature and was concentrated in vacuo. To the residue was added 200 ml. of water and 200 ml. of ethyl acetate. The organic layer was separated and the water layer extracted again with ethyl acetate. The organic phases were combined, washed successively with water (200 ml.), 5% aqueous sodium bicarbonate (200 ml.) and brine (200 ml.) and dried over magnesium sulfate. Removal of the solvent under reduced pressure provides 38.2 g. of the desired product, epimeric at C-6.

B. benzyl 6-fluoromethyl-6-bromopenicillanate

To a cooled (−78° C.) solution of 3.2 g. of diethylaminosulfurtrifluoride in 80 ml. of dry methylene chloride maintained in an atmosphere of nitrogen was added 8.05 g. of benzyl 6-bromo-6-hydroxymethylpenicillanate in 20 ml. of methylene chloride and 3.2 ml. of pyridine. The resulting reaction mixture was allowed to stir in the cold for 45 min. and was allowed to warm to room temperature. The reaction solution was washed with water (2×100 ml.) and a brine solution (2×100 ml.) and dried over magnesium sulfate. The organic layer was then concentrated to dryness in vacuo. The residual material, 6.4 g., was dissolved in 20 ml. of toluene—ethyl acetate (4:1) and chromatographed on a silica gel column, using toluene—ethyl acetate (4:1) as the eluant. Fractions 12 thru 38 were combined and concentrated to dryness to give 3.54 g. of the product.

C. benzyl 6β-fluoromethylpenicillanate

To 3.5 g. of benzyl 6-fluoromethyl-6-bromopenicillanate in 80 ml. of dry benzene maintained under a nitrogen atmosphere was added 2.28 ml. of tri-n-butytin hydride and the resulting reaction mixture heated to reflux. After 1.5 hrs. the reaction mixture was cooled to room temperature and concentrated to an oil, 2.1 g. The residual oil was dissolved in toluene-ethyl acetate (4:1) and was chromatographed on a silica gel column using toluene-ethyl acetate as the eluant. Fractions 33 thru 46 were combined and concentrated to give 1.8 g. of the product as an oil.

D. benzyl 6β-fluoromethylpenicillanate sulfone

To 20 ml. of methylene chloride was added 485 mg. of benzyl 6β-fluoromethylpenicillanate and the resulting solution cooled to 0° C. m-Chlorobenzoic acid (85%) (853 mg.) was added in portions and the reaction allowed to stir for 2 hrs. in the cold and was then allowed to stir at room temperature overnight. The solvent was removed in vacuo and the residue partitioned between ethyl acetate—water (1:1). The pH of the mixture was adjusted to 7.2 with sodium bicarbonate solution and sufficient sodium bisulfite added until a negative starch iodide test was obtained. The organic phase was separated and washed successively with a saturated sodium bicarbonate solution and a saturated brine solution, and dried over magnesium sulfate. Removal of the solvent under reduced pressure gave 400 mg. of the product.

E. 6β-fluoromethylpenicillanic acid sulfone

To a suspension of 365 mg. of 5% palladium-on-calcium carbonate, prereduced with hydrogen at 50 psi for 20 min., in 20 ml. of methanol-water (1:1) was added 356 mg. of benzyl 6β-fluoromethylpenicillanate sulfone, and the mixture shaken in a hydrogen atmosphere at an initial pressure of 48 psi for one hour. The catalyst was filtered and the filtrate freeze dried to give 220 mg. of the final product as the calcium salt.

The NMR spectrum ($D_2O$) showed absorption at 1.45 (s, 3H) 1.57 (s, 3H), 4.2 (s, 1H), 4.4 and 4.9 (d, m, 1H), 5.1 (d, 1H, J=4 Hz), 4.6 and 5.4 (d, m, 2H) ppm.

EXAMPLE 57

6β-Chloromethylpenicillanic Acid Sulfone

A. benzyl 6β-hydroxymethylpenicillanate

A solution containing 10 g. of benzyl 6-bromo-6-hydroxymethylpenicillanate (Example 56A), 6.9 ml. tri-n-butyltin hydride and a trace of azobisisobutyronitirle in 200 ml. of benzene was refluxed for 5 hrs. under nitrogen. The reaction mixture was cooled and concentrated in vacuo. The residue was triturated with hexane and was chromatographed on silica gel, using toluene/ethyl acetate (2:1) as the eluent to give 7.5 g. of the product.

B. benzyl 6β-chloromethylpenicillanate

A solution of 1.28 g. of benzyl 6β-hydroxymethylpenicillanate and 1.88 g. of triphenylphosphine in 5 ml. of carbon tetrachloride was allowed to stir at room temperature for 2 hrs. The reaction mixture was treated with diethyl ether and the solids from the resulting slurry were filtered and chromatographed on 75 g. of silica gel using toluene—ethyl acetate as the eluant. Fractions 20 thru 24 were combined and concentrated to give 358 mg. of product.

The NMR spectrum ($CDCl_3$) showed absorption at 1.42 (s, 3H), 1.6 (s, 3H), 3.83 (m, 3H), 4.4 (s, 1H), 5.18 (s, 2H), 5.4 (d, 1H, J=4 Hz) and 7.37 (s, 5H) ppm.

C. benzyl 6β-chloromethylpenicillanate sulfone

To a cold (0°-5° C.) solution of 200 mg. of benzyl 6β-chloromethylpenicillanate in 30 ml. of methylene chloride under a nitrogen atmosphere was added 300 mg. of 85% m-chloroperbenzoic acid in portions. The resulting reaction mixture was allowed to stir overnight, and was then concentrated to dryness. The residue was partitioned between water-ethyl acetate (1:1) and the pH adjusted to 7.2 with sodium bicarbonate. Sufficient sodium bisulfite was added to destroy the excess peracid and the organic layer was separated, washed with a saturated sodium bicarbonate solution and saturated brine solution, and dried over magnesium sulfate. Removal of the solvent in vacuo gave 189 mg. of the product as an oil.

The NMR spectrum ($CDCl_3$) showed absorption at 1.3 (s, 3H), 1.52 (s, 3H), 3.6 (m, 1H), 3.9 (m, 2H), 4.5 (s, 1H), 4.59 (cl, 1H), J=4 Hz), 5.22 (ABq, 2H, JAB=12 Hz) and 7.35 (s, 5H) ppm.

D. 6β-chloromethylpenicillanic acid sulfone

To a suspension of 200 mg. of 5% palladium-on-calcium carbonate, prereduced with hydrogen at 50 psi for 20 min. in 20 ml. of methanol-water (1:1) was added 189 mg. of benzyl 6β-chloromethylpenicillanate sulfone and the resulting suspension shaken in a hydrogen atmosphere at an initial pressure of 50 psi for 40 min. The catalyst was filtered and the filtrate concentrated under reduced pressure to dryness to give 125 mg. of the final product as the calcium salt.

The NMR spectrum ($D_2O$) showed absorption at 1.41 (s, 3H), 1.57 (s, 3H), 4.0 (m, 3H), 4.22 (s, 1H) and 5.05 (d, 1H, J=4 Hz) ppm.

EXAMPLE 58

6β-Bromomethylpenicillanic Acid Sulfone

A. benzyl 6β-bromomethylpenicillanate

To a solution of 830 mg. of benzyl 6β-hydroxymethylpenicillanate and 2.2 g. of carbon tetrabromide in 5 ml. of methylene chloride cooled to 0°-5° C. and under a nitrogen atmosphere added dropwise 1.47 g. of triphenylphosphine in 5 ml. of methylene chloride. After one hour of stirring in the cold the reaction mixture was chromatographed on silica gel using methylene chloride as the eluant. Fractions 4 thru 11 were combined and concentrated to give 580 mg. of the product as an oil.

The NMR spectrum ($CDCl_3$) showed absorption at 1.42 (s, 3H), 1.60 (s, 3H), 3.6 (m, 2H), 3.9 (m 1H), 4.40 (s, 1H), 5.18 (s, 2H), 5.4 (d, 1H, J=4 Hz) and 7.37 (s, 5H) ppm.

B. benzyl 6β-bromomethylpenicillanate sulfone

To a solution of 250 mg. of benzyl 6β-bromomethylpenicillanate in 30 ml. of methylene chloride cooled to 0°-5° C. and maintained under a nitrogen atmosphere was added 330 mg. of 85% m-chloroperbenzoic acid. After stirring at 0°-5° C. for 2 hrs. the reaction mixture was allowed to stir at room temperature overnight. The solvent was removed under reduced pressure and the residue partitioned between water-ethyl acetate (1:1). The pH was adjusted to 7.2 with a saturated sodium bicarbonate solution and sufficient sodium bisulfite was added to destroy any residual peracid. The organic layer is washed with a saturated sodium bicarbonate solution followed by a saturated brine solution and drying over magnesium sulfate. Removal of the solvent in vacuo gave 220 mg. of product as an oil.

The NMR spectrum ($CDCl_3$) showed absorption at 1.29 (s, 3H), 1.55 (s, 3H), 3.5 (m, 2H), 3.9 (m, 1H), 4.5 (s, 1H), 4.59 (a, 1H, J=4 Hz), 5.22 (ABq, 2H, JAB=12 Hz) and 7.35 (s, 5H) ppm.

C. 6β-bromomethylpenicillanic acid sulfone

A suspension of 290 mg. of benzyl 6β-bromomethylpenicillanate sulfone and 300 mg. of 5% palladium-on-calcium carbonate, prereduced with hydrogen at 50 psi for 20 min., in 20 ml. of methanol-water (1:1) was shaken in a hydrogen atmosphere at an initial pressure of 50 psi for 35 min. The catalyst was filtered and the methanol removed from the filtrate in vacuo. The residual aqueous solution was extracted with ethyl acetate and freeze dried to give 200 mg. of the product as the calcium salt.

The NMR spectrum ($D_2O$) showed absorption at 1.4 (s, 3H), 1.60 (s, 3H), 3.8 (m, 2H), 4.0 (m, 1H), 4.2 (s, 1H) and 5.0 (d, 1H, J=4 Hz) ppm.

EXAMPLE 59

6β-Chloromethylpenicillanic Acid

To a suspension of 300 mg. of 5% palladium-on-calcium carbonate, prereduced with hydrogen at 50 psi for 20 min., in 20 ml. of methanol-water (1:1) was added 300 mg. of benzyl 6β-chloromethylpenicillanate (Example 57B) and the resulting suspension shaken in a hydrogen atmosphere at an initial pressure of 50 psi for 45 min. An additional 300 mg. of catalyst was added and the hydrogenation continued for 35 min. The catalyst was filtered and the methanol removed in vacuo from the filtrate. The aqueous residue was extracted with ethyl acetate and then freeze dried to give 220 mg. of the product as the calcium salt.

The NMR spectrum ($D_2O$) showed absorption at 1.52 (s, 3H), 1.62 (s, 3H), 3.95 (m, 3H), 4.2 (s, 1H) and 5.4 (d, 1H, J=4 Hz) ppm.

In a similar manner, starting with benzyl 6β-fluoromethylpenicillanate and benzyl 6β-bromomethylpenicillanate, 6β-fluoromethylpenicillanic acid and 6β-bromomethylpenicillanic acid are prepared respectively.

EXAMPLE 60

6β-Fluoromethylpenicillanic Acid Sulfoxide

A. benzyl 6β-fluoromethylpenicillanic acid sulfoxide

To a solution of 323 mg. of benzyl 6β-fluoromethylpenicillanate in 25 ml. of dry methylene chloride at 0° C. is added 240 mg. of 85% m-chloroperbenzoic acid in portions. After two hours the cooling bath is removed and the reaction mixture allowed to stir at room temperature overnight. The solvent is removed in vacuo, and the residue partitioned between ethyl acetate and water (1:1) at pH 7.5. The organic phase is separated, washed with a saturated sodium bicarbonate and brine solution and dried over magnesium sulfate. Removal of the solvent gives the desired product.

B. 6β-fluoromethylpenicillanic acid sulfoxide

A suspension of 400 mg. of 5% palladium-on-calcium carbonate, prereduced with hydrogen at 50 psi for 20 min., and 400 mg. of benzyl 6β-fluoromethylpenicillanate in 20 ml. of methanol-water (1:1) are shaken in an atmosphere of hydrogen at an initial pressure of 50 psi for one hour. The catalyst is filtered and the methanol removed from the filtrate. The aqueous residue is extracted with ethyl acetate and is then acidified to pH 1.5 with dilute 6 N hydrochloric acid. Fresh ethyl acetate is added and the organic phase is separated, washed with a saturated brine solution and dried over magnesium sulfate. Removal of the solvent in vacuo gives the desired compound as the free acid.

Starting with benzyl 6-chloromethylpenicillanate or benzyl 6-bromomethylpenicillanate and employing the above procedures gives 6-chloromethylpenicillanic acid sulfoxide and 6-bromomethylpenicillanic acid sulfoxide, respectively.

EXAMPLE 61

6β-Hydroxymethylpenicillanic Acid Sulfone

A. benzyl 6β-hydroxymethylpenicillanate sulfone m-Chloroperbenzoic acid (11.8 g.) was added to a solution of 7.5 g. of benzyl 6β-hydroxymethylpenicillanate (Example 57A) in 600 ml. of methylene chloride cooled to 0°–5° C. The solution was then allowed to warm to room temperature and was stirred for 5 hrs. The solvent was removed in vacuo and the residue partitioned between 200 ml. of water and 200 ml. of ethyl acetate. The pH of the mixture was adjusted to 7 by the addition of a saturated sodium bicarbonate solution, and sufficient sodium bisulfite was added to give a negative peroxide test (starch-iodide). The layers were separated, and the aqueous washed with ethyl acetate. The organic layer and washings were combined, washed successively with water, 5% sodium bicarbonate solution and brine and dried over magnesium sulfate. Removal of the solvent under reduced pressure gave a foam, which on chromatographing on silica gel (chloroform-ethyl acetate 20:3) gave 3.5 g. of the desired intermediate product.

B. calcium 6β-hydroxymethylpenicillanate sulfone

To a 30 ml. of solution of water-methanol (1:1) was added 3.5 g. of 5% palladium on calcium carbonate and the catalyst prehydrogenated at 47 psi in a hydrogenation apparatus. To the resulting catalyst was added 3.5 g. of benzyl 6β-hydroxymethylpenicillanate sulfone in 10 ml. of methanol and 20 ml. of tetrahydrofuran, and the mixture was shaken in a hydrogen atmosphere at 48 psi for 30 min. The catalyst was filtered through a filter aid and the filtrate concentrated in vacuo. The aqueous residue was extracted with ethyl acetate (2×100 ml.) and freeze dried to give 3.0 g. of the desired product as the calcium salt.

The NMR spectrum ($CDCl_3$-free acid) showed absorption at 1.49 (s, 3H), 1.6 (s, 3H), 4.1 (m, 3H), 4.32 (s, 1H) and 4.9 (d, 1H, J=4 Hz) ppm.

EXAMPLE 62

6β-Hydroxymethylpenicillanic Acid Sulfoxide

A.

To a solution of 7.5 g. of benzyl 6β-hydroxymethylpenicillanate (Example 57A) in 500 ml. of dry methylene chloride cooled to 0°–5° C. is added 5.9 g. of m-chloroperbenzoic acid in portions. The solution is then allowed to warm to room temperature and stir overnight. The solvent is removed in vacuo and the residue treated with water-ethyl acetate (1:1). The pH of the mixture is adjusted to 7.2 and sufficient sodium bisulfite is added to destroy any remaining peracid. The organic layer is separated, washed successively with water, 5% sodium bicarbonate solution and a saturated brine solution, and dried over magnesium sulfate. Removal of the solvent under reduced pressure gives the desired product.

EXAMPLE 63

Pivaloyloxymethyl 6β-hydroxymethylpenicillanate sulfone

To a solution of 1.0 g. of 6β-hydroxymethylpenicillanic acid sulfone sodium salt in 10 ml. of dimethylformamide and cooled to 0°–5° C. was added 0.52 ml. of chloromethyl pivalate. After stirring overnight at room temperature, the reaction mixture was poured into a mixture of water-ethyl acetate. The ethyl acetate layer was separated, backwashed with water (3×100 ml.) and a brine solution (3×50 ml.) and dried over magnesium sulfate. The solvent was removed in vacuo to give 1.1 g. of the product as an oil.

The NMR spectrum (CDCl$_3$) showed absorption at 1.27 (s, 9H), 1.42 (s, 3H), 1.6 (s, 3H), 2.9 (bs, 1H), 4.2 (m, 3H), 4.58 (s, 1H), 4.75 (m, 1H) and 5.82 (ABq, 2H, $8_A$–$8_B$=16 Hz) ppm.

EXAMPLE 64

Starting with the appropriate 6β-hydroxymethylpenicillanic acid, sulfoxide or sulfone and requisite halide and employing the procedure of Example 63, the following intermediate compounds are prepared:

[Structure: HOCH$_2$ substituted β-lactam with S(O)$_n$, N, CO$_2$R$_{13}$, CH$_3$, CH$_3$]

| n | R$_{13}$ |
|---|---|
| 0 | —CH$_2$O$_2$CCH$_3$ |
| 0 | —CH$_2$O$_2$CCH(CH$_3$)$_2$ |
| 0 | —CH(CH$_3$)O$_2$CCH$_3$ |
| 0 | —CH$_2$O$_2$C(CH$_2$)$_4$CH$_3$ |
| 0 | —C$_4$H$_3$O$_2$* |
| 0 | —C(CH$_3$)$_2$O$_2$CO(CH$_2$)$_2$CH$_3$ |
| 1 | —CH$_2$O$_2$CC(CH$_3$)$_3$ |
| 1 | —CH(CH$_3$)O$_2$COC$_2$H$_5$ |
| 1 | —C(CH$_3$)$_2$O$_2$CO(CH$_2$)$_2$CH$_3$ |
| 1 | —C$_4$H$_5$O$_2$+ |
| 1 | —CH$_2$O$_2$CCH(CH$_3$)$_2$ |
| 1 | —CH(CH$_3$)O$_2$CCH$_3$ |
| 2 | —CH$_2$O$_2$CCH$_3$ |
| 2 | —CH(CH$_3$)O$_2$COC$_2$H$_5$ |
| 2 | —C(CH$_3$)$_2$O$_2$CCH$_3$ |
| 2 | —CH$_2$O$_2$COCH(CH$_3$)$_2$ |
| 2 | —C$_4$H$_3$O$_2$* |
| 2 | —CH$_2$O$_2$C(CH$_2$)$_4$CH$_3$ |
| 2 | —C$_4$H$_5$O$_2$+ |
| 2 | —C$_8$H$_5$O$_2$# |

*4-crotonolactonyl
+γ-butyrolacton-4-yl
3-phthalidyl

EXAMPLE 65

Pivaloyloxymethyl 6β-fluoromethylpenicillanate Sulfone

To a solution of 3.2 g. of diethylaminosulfurtrifluoride in 80 ml. of dry methylene chloride cooled to −78° C. and maintained under a nitrogen atmosphere is added 7.5 g. of pivaloyloxymethyl 6-hydroxymethylpenicillanate sulfone (Example 63) in 20 ml. of methylene chloride containing 3.2 ml. of pyridine. The reaction mixture is allowed to stir in the cold for 45 min. and then allowed to warm to room temperature. The reaction solution is washed with water (2×100 ml.) and a saturated brine solution (2×100 ml.) and dried over magnesium sulfate. The organic phase is separated and concentrated to dryness. The residual material is chromatographed on silica gel, and the fractions containing the product combined and concentrated to give the desired material.

EXAMPLE 66

Pivaloyloxymethyl 6β-chloromethylpenicillanate Sulfoxide

A solution of 1.88 g. of triphenylphosphine and 1.44 g. of pivaloyloxymethyl 6β-hydroxymethylpenicillanate sulfoxide (Example 64) in 6 ml. of carbon tetrachloride is allowed to stir at room temperature for 3 hrs. The reaction mixture is treated with diethyl ether and the resulting solids are filtered and chromatographed on silica gel. The fractions containing the desired material are combined and concentrated in vacuo to give the product.

EXAMPLE 67

Acetoxymethyl 6β-bromomethylpenicillanate

To a solution of 788 mg. of acetoxymethyl 6β-hydroxymethylpenicillanate and 2.2 g. of carbon tetrabromide in 6 ml. of methylene chloride cooled to 0° C. and under a nitrogen atmosphere is added dropwise 1.47 g. of triphenylphosphine in 5 ml. of methylene chloride. After 2.5 hrs. of stirring in the cold the reaction mixture is treated with diisopropyl ether and the solids filtered, and chromatographed on silica gel. The fractions containing the desired material are combined and concentrated in vacuo to give the product.

EXAMPLE 68

Starting with the appropriate 6β-hydroxymethylpenicillanate ester and employing the procedure from the indicated example, the following compounds are prepared:

[Structure: R-substituted β-lactam with S(O)$_n$, N, CO$_2$R$_{13}$, CH$_3$, CH$_3$]

| R | n | Procedure | R$_{13}$ |
|---|---|---|---|
| FCH$_2$— | 0 | Example 65 | —CH$_2$O$_2$CCH$_3$ |
| FCH$_2$— | 0 | Example 65 | —CH(CH$_3$)O$_2$CCH$_3$ |
| FCH$_2$— | 0 | Example 65 | —(CH$_3$)$_2$O$_2$CO(CH$_2$)$_2$CH$_3$ |
| ClCH$_2$— | 0 | Example 66 | —C$_4$H$_3$O$_2$* |
| ClCH$_2$ | 0 | Example 66 | —CH$_2$O$_2$CCH$_3$ |
| ClCH$_2$— | 0 | Example 66 | —C(CH$_3$)$_2$O$_2$CO(CH$_2$)$_2$CH$_3$ |
| BrCH$_2$— | 0 | Example 67 | —CH$_2$O$_2$CCH(CH$_3$)$_2$ |
| BrCH$_2$— | 0 | Example 67 | —CH$_2$O$_2$C(CH$_2$)$_4$CH$_3$ |
| FCH$_2$— | 1 | Example 65 | —C$_4$H$_5$O$_2$+ |
| FCH$_2$— | 1 | Example 65 | —CH(CH$_3$)O$_2$COC$_2$H$_5$ |
| FCH$_2$— | 1 | Example 65 | —CH$_2$O$_2$CCH$_3$ |
| ClCH$_2$— | 1 | Example 66 | —C(CH$_3$)$_2$O$_2$CO(CH$_2$)$_2$CH$_3$ |
| ClCH$_2$— | 1 | Example 66 | —CH(CH$_3$)O$_2$CCH$_3$ |
| ClCH$_2$— | 1 | Example 66 | —CH(CH$_3$)O$_2$COC$_2$H$_5$ |
| BrCH$_2$— | 1 | Example 67 | —CH$_2$O$_2$CC)CH$_3$)$_3$ |
| FCH$_2$— | 2 | Example 65 | —CH$_2$O$_2$CCH$_3$ |
| FCH$_2$— | 2 | Example 65 | —CH(CH$_3$O$_2$COC$_2$H$_5$ |
| ClCH$_2$— | 2 | Example 66 | —C$_8$H$_5$O$_2$* |
| BrCH$_2$— | 2 | Example 67 | —CH$_2$O$_2$COCH(CH$_3$)$_2$ |
| BrCH$_2$— | 2 | Example 67 | —C$_8$H$_5$O$_2$* |

*4-crotonolactonyl
*γ-butyrolacton-4-yl
3-phthalidyl

EXAMPLE 69

6β-Fluoromethylpenicillanic Acid

A. 6β-hydroxymethylpenicillanic acid phenacyl ester

To a solution of 2.31 g. of 6β-hydroxymethylpenicillanic acid and 1.98 g. of phenacyl bromide in 40 ml. of a 1:1 mixture of dry dimethylformamide-tetrahydrofuran cooled to 0° C. is added dropwise over a 15 min. period 1.4 ml. of triethylamine. The cold solution is stirred for 3.5 hrs. and is then treated with 125 ml. of ethyl acetate and 100 ml. of a saturated aqueous sodium bicarbonate solution. The aqueous phase is separated and discarded and fresh water is added to the organic phase. The pH is adjusted to 5.0 with 6 N hydrochloric acid and the organic phase separated, washed with a brine solution, dried over magnesium sulfate and concentrated in vacuo to give the desired product.

B. 6β-fluoromethylpenicillanic acid

In a procedure similar to that in Example 56B, to a solution of 3.2 g. of diethylaminosulfurtrifluoride in 80 ml. of methylene chloride cooled to −78° C. and maintained under a nitrogen atmosphere is added 6.98 g. of a 6β-hydroxymethylpenicillanic acid phenacyl ester in 25 ml. of methylene chloride containing 3.2 ml. of pyridine. The resulting reaction mixture is allowed to stir for 45 min. in the cold and is then allowed to warm to room temperature. The reaction solution is washed with water (2×100 ml.) and a saturated brine solution (2×100 ml.), and dried over magnesium sulfate. The organic phase is separated and concentrated to dryness in vacuo. The residue is chromatographed on silica gel and the fractions containing the desired material are combined and concentrated to give the intermediate product.

C. 6β-fluoromethylpenicillanic acid

The above residual product is dissolved in 25 ml. of dry dimethylformamide and is treated with 375 mg. of potassium thiophenoxide in 4 ml. of dimethylformamide. After stirring at room temperature for 2 hrs. the reaction mixture is added to 60 ml. of a saturated aqueous sodium bicarbonate solution. Ethyl acetate (60 ml.) is added and the organic phase is separated and fresh ethyl acetate added. The pH of the aqueous phase is adjusted to 1.5 with 6 N hydrochloric acid and the organic phase separated, washed with a saturated brine solution and dried over sodium sulfate. Removal of the solvent in vacuo gives the desired product.

EXAMPLE 70

A.

Starting with the appropriate 6β-hydroxymethylpenicillanic acid, sulfoxide or sulfone and requisite α-halomethylcarbonyl, reagent and employing the procedure of Example 69A, the following compounds are prepared:

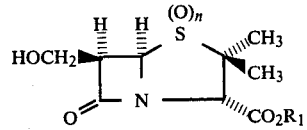

| n | $R_1$ |
|---|---|
| 1 | —$CH_2COC_6H_5$ |
| 2 | —$CH_2COC_6H_5$ |
| 0 | —$CH_2COCH_3$ |
| 2 | —$CH_2COCH_3$ |
| 0 | —$CH_2COCH_2CH_3$ |
| 1 | —$CH_2COCH_2CH_3$ |
| 0 | —$CH_2CN$ |
| 0 | —$CH_2CO_2CH_3$ |
| 1 | —$CH_2CO_2CH_3$ |
| 0 | —$CH_2CO_2CH_2CH_2CH_3$ |
| 0 | —$CH_2COCH(CH_3)_2$ |
| 2 | —$CH_2COCH(CH_3)_2$ |
| 1 | —$CH_2CO_2C_2H_5$ |
| 0 | —$CH_3CO(CH_2)_2CH_3$ |
| 1 | —$CH_2CO(CH_2)_2CH_3$ |
| 2 | —$CH_2CO(CH_2)_2CH_3$ |

B.

Starting with the esters from Example 69A and 70A and employing the indicated procedure, the following intermediates are synthesized:

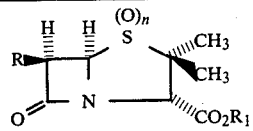

| R | n | $R_1$ | Procedure |
|---|---|---|---|
| $ClCH_2$— | 0 | —$CH_2COC_6H_5$ | Example 66 |
| $ClCH_2$— | 2 | —$CH_2CO_6H_5$ | Example 66 |
| $FCH_2$— | 1 | —$CH_2COC_6H_5$ | Example 69B |
| $ClCH_2$ | 0 | —$CH_2COCH_3$ | Example 66 |
| $ClCH_2$— | 2 | —$CH_2COCH_3$ | Example 66 |
| $FCH_2$— | 0 | —$CH_2COCH_2CH_3$ | Example 69B |
| $BrCH_2$— | 0 | —$CH_2CO_6H_5$ | Example 67 |
| $BrCH_2$— | 1 | —$CH_2COCH_2CH_3$ | Example 67 |
| $FCH_2$— | 0 | —$CH_2CN$ | Example 69B |
| $ClCH_2$— | 0 | —$CH_2CN$ | Example 66 |
| $BrCH_2$— | 0 | —$CH_2CO_2CH_3$ | Example 67 |
| $BrCH_2$— | 1 | —$CH_2CO_2CH_3$ | Example 67 |
| $FCH_2$— | 0 | —$CH_2CO_2(CH_2)_2CH_3$ | Example 69B |
| $FCH_2$— | 0 | —$CH_2COCH(CH_3)_2$ | Example 69B |
| $ClCH_2$— | 0 | —$CH_2COCH(CH_3)_2$ | Example 66 |
| $ClCH_2$— | 2 | —$CH_2C)CH(CH_3)_2$ | Example 66 |
| $BrCH_2$— | 2 | —$CH_2C)CH(CH_3)_2$ | Example 67 |
| $ClCH_2$— | 1 | —$CH_2CO_2C_2H_5$ | Example 66 |
| $ClCH_2$— | 0 | —$CH_2CO(CH_2)_2CH_3$ | Example 66 |
| $BrCH_2$— | 1 | —$CH_2CO(CH_2)_2CH_3$ | Example 67 |
| $FCH_2$— | 1 | —$CH_2CO(CH_2)_2CH_3$ | Example 69B |
| $FCH_2$— | 2 | —$CH_2CO(CH_2)_2CH_3$ | Example 69B |
| $ClCH_2$— | 2 | —$CH_2CO(CH_2)_2CH_3$ | Example 66 |

C.

Starting with the esters of Example 70B, and employing the procedure of Example 69C the following penicillanic acids are prepared:

6β-chloromethylpenicillanic acid, 6β-chloromethylpenicillanic acid sulfone, 6β-fluoromethylpenicillanic acid sulfoxide, 6β-fluoromethylpenicillanic acid, 6β-bromomethylpenicillanic acid, 6β-bromomethylpenicillanic acid sulfoxide, 6β-bromomethylpenicillanic acid sulfone, 6β-chloromethylpenicillanic acid sulfoxide and 6β-fluoromethylpenicillanic acid sulfone.

EXAMPLE 71

6β-Chloromethylpenicillanic Acid Sulfoxide

A. 0-(6-β-hydroxymethylpenicillanoyl)benzaldehyde oxime sulfoxide

To a solution of 2.47 g. of 6β-hydroxymethylpenicillanic acid sulfoxide in 200 ml. of methylene chloride is added 1.0 g. of triethylamine and the resulting reaction mixture cooled to 0° C. Ethyl chloroformate (1.1 g.) is added dropwise over a period of 15 min. and the reaction maintained at 0° C. for 30 min. Benzaldehyde oxime (1.2 g.) is added in 10 ml. of dry acetone and the stirring continued for 2 hrs. The reaction mixture is then allowed to warm to room temperature and the stirring is continued for 2 additional hours. The reaction mixture is filtered and the filtrate concentrated to dryness. The residue is distributed between ethyl acetate (100 ml.) and water (50 ml.). The aqueous layer is separated and the organic layer washed with a saturated aqueous sodium bicarbonate solution and is dried over magnesium sulfate. Removal of the solvent in vacuo affords the desired product.

B. 0-(6β-chloromethylpenicillanoyl)benzaldehyde oxime sulfoxide

A solution of 2.8 g. of 0-(6β-hydroxymethylpenicillanoyl)benzaldehyde oxime sulfoxide and 4.19 g. of triphenylphosphine in 10 ml. of carbon tetrachloride is allowed to stir at room temperature for 2.5 hrs. The reaction mixture is treated with diethyl ether and the solids filtered and chromatographed on 150 g. of silica gel. The fractions containing the product are combined and concentrated in vacuo to dryness.

C. 6β-chloromethylpenicillanic acid sulfoxide

One and eight tenths grams of the above residue is dissolved in 25 ml. of dimethylformamide to which is then added 660 mg. of potassium thiophenoxide in 10 ml. of the same solvent. After stirring for 2 hrs. at room temperature the reaction mixture is added to a saturated sodium bicarbonate solution. The aqueous is extracted with 75 ml. of ethyl acetate and the organic phase separated. The pH of the aqueous is adjusted to 1.5 with 6 N hydrochloric acid and extracted with ethyl acetate. The organic phase is separated, dried over sodium sulfate and concentrated in vacuo to dryness to give the desired product.

EXAMPLE 72

A.

Starting with the appropriate 6β-hydroxymethylpenicillanic acid, sulfoxide or sulfone and employing the procedure of Example 71A, the following compounds are prepared:

0-(6β-hydroxymethylpenicillanoyl)benzaldehyde oxime and 0-(6β-hydroxymethylpenicillanoyl)benzaldehyde oxime sulfone.

B.

Starting with the esters from Example 71A and 72A and employing the indicated procedure, the following intermediates are prepared:

0-(6-β-fluoromethylpenicillanoyl)benzaldehyde oxime-Procedure Example 65; 0-(6β-fluoromethylpenicillanoyl)benzaldehyde oxime sulfoxide-Procedure Example 65; 0-(6β-fluoromethylpenicillanoyl)benzaldehyde oxime sulfone-Procedure Example 65; 0-(6β-chloromethylpenicillanoyl)benzaldehyde oxime-Procedure Example 66; 0-(6β-chloromethylpenicillanoyl)benzaldehyde oxime sulfoxide-Procedure Example 66; 0-(6β-bromopenicillanoyl)benzaldehyde oxime sulfoxide-Procedure Example 67; and 0-(6β-bromomethylpenicillanoyl)benzaldehyde oxime sulfone—Procedure Example 67.

C.

Starting with the esters of Example 72B and employing the procedure of Example 71C, the following compounds are synthesized:

6β-fluoromethylpencillanic acid; 6β-fluoromethylpenicillanic acid sulfoxide: 6β-fluoromethylpenicillanic acid sulfone; 6β-chloromethylpenicillanic acid; 6β-chloromethylpenicillanic acid sulfone; 6β-bromomethylpenicillanic acid sulfoxide; and 6β-bromomethylpenicillanic acid sulfone.

EXAMPLE 73

6β-Bromomethylpenicillanic Acid

A. benzhydryl 6β-hydroxymethylpenicillanate

Diphenyl diazomethane (19.4 g.) in 100 ml. of ether is added to a solution of 23.1 g. of 6β-hydroxymethylpenicillanic acid in 200 ml. of tetrahydrofuran. After 2 hrs. the solvents are removed under vacuum and the residue dissolved in methylene chloride and washed with saturated aqueous sodium carbonate solution.

The organic phase is dried over magnesium sulphate and evaporated. The crude product is triturated with a mixture of ether and petroleum ether (b.p. 40°–60° C.) and filtered to give the desired intermediate.

B. Benzhydryl 6β-bromomethylethylpenicillanate

To a solution of 1.03 g. of benzhydryl 6β-hydroxymethylpencillanate and 2.2 g. of carbon tetrabromide in 5 ml. of methylene chloride cooled to 0° C. and under a nitrogen atmosphere is added dropwise 1.47 g. of triphenylphosphine in 6 ml. of methylene chloride. After 1.5 hrs. of stirring at 0° C. the reaction solvent is removed in vacuo and the residue chromatographed on silica gel. The fractions containing the product are combined and concentrated to dryness.

C. 6β-bromomethylpenicillanic acid

Trifluoroacetic acid (0.5 ml.) is added to 80 mg. of benzhydryl 6β-bromomethylpenicillanate in 1 ml. of methylene chloride and the reaction mixture stirred for 30 min. at room temperature. The mixture is evaporated to dryness to yield the crude product, which is purified by chromatography on silica gel.

EXAMPLE 74

A.

Starting with the appropriate 6β-hydroxymethylpenicillanic acid sulfoxide or sulfone and diphenyl diazomethane and following the procedure of Example 73A, the following intermediate compounds are prepared: benzhydryl 6β-hydroxymethylpenicillanate sulfoxide and benzhydryl 6β-hydroxymethylpenicillanate sulfone.

B.

Employing the appropriate benzhydryl 6β-hydroxymethylpenicillanate and using the indicated procedure the following compounds are prepared:

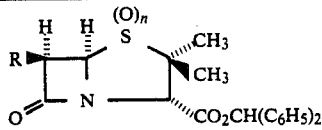

| R | n | Procedure |
|---|---|---|
| FCH₂— | 0 | Example 65 |
| FCH₂— | 1 | Example 65 |
| ClCH₂— | 1 | Example 66 |
| ClCH₂— | 2 | Example 66 |
| BrCH₂— | 0 | Example 67 |
| BrCH₂— | 1 | Example 67 |
| BrCH₂— | 2 | Example 67 |

C.

Using the appropriate ester from Example 74B and employing the procedure of Example 73C, the following products are synthesized:

6β-fluoromethylpenicillanic acid; 6β-fluoromethylpenicillanic acid sulfoxide; 6β-chloromethylpenicillanic acid sulfoxide; 6β-chloromethylpenicillanic acid sulfone, 6β-bromomethylpenicillanic acid; 6β-bromomethylpenicillanic acid sulfoxide; and 6β-bromomethylpenicillanic acid sulfone.

EXAMPLE 75

6β-Fluoromethylpenicillanic Acid Sulfone

A. 4-methoxybenzyl 6β-hydroxymethylpenicillanate sulfone

To a solution of 2.6 g. of 6β-hydroxymethylpenicillanic acid sulfone and 2.01 g. of 4-methoxybenzyl bromide in 50 ml. of a 1:1 mixture of dry dimethylformamide-tetrahydrofuran cooled to 0° C. is added dropwise over a 20 min. period 1.4 ml. of triethylamine. The solution is allowed to stir in the cold for 4 hrs. and is then treated with 150 ml. of ethyl acetate and 125 ml. of a saturated aqueous sodium bicarbonate solution. The aqueous phase is separated and discarded, and fresh water added to the organic phase. The pH is adjusted to 5.0 with 6 N hydrochloric acid and the organic phase separated, washed with a brine solution, dried over magnesium sulfate and concentrated in vacuo to give the desired product.

B. 4-methoxybenzyl 6β-fluoromethylpenicillanate sulfone

To a cold solution (−78° C.) of 3.2 g. of diethylaminosulfurtrifluoride in 85 ml. of dry methylene chloride under a nitrogen atmosphere is added 7.0 g. of 4-methoxybenzyl 6β-hydroxymethylpenicillanate in 25 ml. of methylene chloride containing 3.2 ml. of pyridine. The resulting reaction mixture is allowed to stir at −78° C. for one hour and is then allowed to warm to room temperature. The reaction mixture is washed with warm water (2×100 ml.) and a saturated brine solution (2×100 ml.), and dried over magnesium sulfate. The organic layer is concentrated to dryness to give the intermediate product.

C. 6β-fluoromethylpenicillanic acid sulfone

4-Methoxybenzyl 6β-fluoromethylpenicillnate sulfone (90 mg.) is dissolved in 2 ml. of methylene chloride to which is then added 1 ml. of trifluoroacetic acid and 3 drops of anisole. The mixture is stirred at room temperature for 5 hrs. and is then evaporated to dryness. The residue is chromatographed on silica. The fractions containing the product are combined and concentrated to give the desired product.

EXAMPLE 76

A.

Using the appropriate 6β-hydroxymethylpenicillanic acid, sulfoxide or sulfone and requisite halide, and employing the procedure from Example 75A, the following intermediates are prepared:

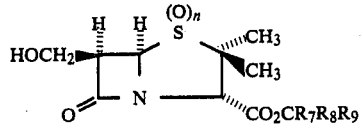

| n | R₇ | R₈ | R₉ |
|---|---|---|---|
| 0 | CH₃— | C₆H₅— | C₆H₅— |
| 0 | C₆H₅— | C₆H₅— | C₆H₅— |
| 0 | H— | CH₃— | 4-CH₃OC₆H₄— |
| 0 | CH₃— | CH₃— | 4-CH₃OC₆H₄— |
| 0 | H— | C₆H₅— | 4-CH₃OC₆H₄— |
| 1 | H— | H— | 4-CH₃OC₆H₄— |
| 1 | H— | CH₃— | 4-CH₃OC₆H₄ |
| 1 | C₆H₅— | C₆H₅— | C₆H₅— |
| 1 | CH₃— | CH₃— | 4-CH₃OC₆H₄— |
| 1 | CH₃— | C₆H₅ | C₆H₅ |
| 2 | CH₃— | CH₃— | 4-CH₃OC₆H₄— |
| 2 | C₆H₅— | C₆H₅— | C₆H₅— |

B.

Starting with the esters in Example 76A, and using the indicated procedure, the following compounds are prepared:

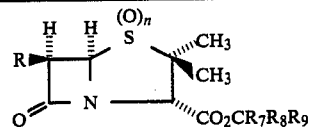

| R | n | R₇ | R₈ | R₉ | Procedure |
|---|---|---|---|---|---|
| FCH₂— | 0 | CH₃— | C₆H₅— | C₆H₅— | Example 65 |
| FCH₂— | 0 | C₆H₅— | C₆H₅— | C₆H₅— | Example 65 |
| ClCH₂ | 0 | H— | CH₃— | 4-CH₃OC₆H₄— | Example 66 |
| ClCH₂— | 0 | CH₃— | CH₃— | 4-CH₃OC₆H₄— | Example 66 |
| BrCH₂— | 0 | H— | C₆H₅— | 4-CH₃OC₆H₄— | Example 67 |
| BrCH₂— | 0 | C₆H₅— | C₆H₅— | C₆H₅— | Example 67 |
| FCH₂— | 1 | H— | H— | 4-CH₃OC₆H₄— | Example 65 |
| FCH₂— | 1 | CH₃— | C₆H₅— | C₆H₅— | Example 65 |
| ClCH₂— | 1 | H— | CH₃— | 4-CH₃OC₆H₄— | Example 66 |
| ClCH₂— | 1 | C₆H₅— | C₆H₅— | C₆H₅— | Example 66 |
| ClCH₂— | 1 | CH₃— | CH₃— | 4-CH₃OC₆H₄— | Example 66 |
| BrCH₂— | 1 | C₆H₅— | C₆H₅— | C₆H₅— | Example 67 |
| FCH₂— | 2 | C₆H₅— | C₆H₅— | C₆H₅— | Example 65 |
| FCH₂— | 2 | CH₃— | CH₃— | 4-CH₃OC₆H₄— | Example 65 |
| ClCH₂— | 2 | CH₃— | CH₃— | 4-CH₃OC₆H₄— | Example 66 |
| BrCH₂— | 2 | CH₃— | CH₃— | 4-CH₃OC₆H₄— | Example 67 |
| BrCH₂— | 2 | C₆H₅— | C₆H₅— | C₆H₅— | Example 67 |

C.

Employing the esters in Example 76B, and using the procedure of Example 75C the following compounds are synthesized:

6β-fluoromethylpenicillanic acid; 6β-chloromethylpenicillanic acid; 6β-bromomethylpenicillanic acid; 6β-fluoromethylpenicillanic acid sulfoxide; 6β-chloromethylpenicillanic acid sulfoxide; 6β-bromomethylpenicillanic acid sulfoxide; 6β-fluoromethylpenicillanic acid sulfone; 6β-chloromethylpenicillanic acid sulfone; and 6β-bromomethylpenicillanic acid sulfone.

EXAMPLE 77

6β-Bromomethylpenicillanic Acid

A. 6β-hydroxymethylpenicillanic acid methyl acetoacetate ester

To 3.22 g. of 6β-hydroxymethylpenicillanic acid sodium salt in 100 ml. of dimethylformamide is added 1.6 ml. of methyl 2-chloroacetoacetate, and the resulting reaction mixture allowed to stir over night at room temperature. The mixture is poured into 400 ml. of ice and water and extracted with ethyl acetate. The organic phase is separated and washed successively with water, a saturated aqueous sodium bicarbonate solution and a brine solution. The organic phase is then dried over magnesium sulfate and concentrated and chromatographed on silica gel. The fractions of eluate, containing the product are combined and concentrated in vacuo to give the desired product.

B. 6β-bromomethylpenicillanic acid methyl acetoacetate ester

To a solution of 897 mg. of 6β-hydroxymethylpenicillanic acid methyl acetoacetate ester and 2.2 g. of carbon tetrabromide in 5 ml. of methylene chloride cooled to 0° C. and maintained under a nitrogen atmosphere is added dropwise 1.47 g. of triphenylphosphine in 7 ml. of methylene chloride. After 1.5 hrs. of stirring at 0° C. the reaction is allowed to warm to room temperature and is concentrated to dryness. The residual material is chromatographed on silica gel, and the fractions containing the product combined and concentrated to give the desired intermediate.

C. 6β-bromopenicillanic acid

To 4.1 g. of 6β-bromomethylpenicillanic acid methyl acetoacetate ester, prepared by the above procedure, in 50 ml. of acetone is added 2.1 g. of sodium nitrite in 10 ml. of water with stirring. After stirring for 3 hrs. at room temperature the solvent is removed in vacuo and the residue aqueous extracted once with ether. The aqueous is then made acid to pH 1.5 with 6 N hydrochloric and extracted with ethyl acetate. The organic phase is dried over sodium sulfate and concentrated under reduced pressure to give the desired product.

EXAMPLE 78

A.

Starting with the appropriate 6β-hydroxymethylpenicillanic acid, sulfoxide or sulfone, and the requisite 2-chloroacetoacetate and using the procedure of Example 77A the following compounds are prepared:

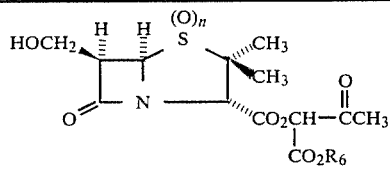

| n | R6 |
|---|---|
| 0 | C2H5 |
| 0 | n-C3H7— |
| 0 | n-C3H7— |

-continued

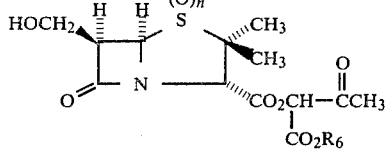

| n | R6 |
|---|---|
| 1 | CH3— |
| 1 | C2H5 |
| 1 | n-C3H7 |
| 2 | CH3 |
| 2 | n-C3H7 |
| 2 | i-C3H7 |

B.

Using the esters of Example 77A and employing the indicated procedure, the following intermediates are synthesized:

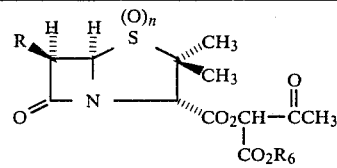

| R | n | R6 | Procedure |
|---|---|---|---|
| FCH2— | 0 | CH3— | Example 65 |
| FCH2— | 0 | n-C3H7— | Example 65 |
| ClCH2 | 0 | C2H5— | Example 66 |
| ClCH2 | 0 | i-C3H7— | Example 66 |
| BrCH2— | 0 | C2H5— | Example 67 |
| FCH2— | 1 | CH3— | Example 65 |
| FCH2— | 1 | i-C3H7— | Example 65 |
| ClCH2— | 1 | CH3— | Example 66 |
| BrCH2— | 1 | n-C3H7— | Example 67 |
| BrCH2— | 1 | CH3— | Example 67 |
| FCH2— | 2 | CH3— | Example 65 |
| FCH2— | 2 | n-C3H7— | Example 65 |
| ClCH2— | 2 | n-C3H7— | Example 66 |
| ClCH2— | 2 | i-C3H7— | Example 66 |
| BrCH—2 | 2 | CH3— | Example 67 |

C.

Starting with the esters in Example 78B and using the procedure of Example 77C, the following compounds are prepared:

6-β-fluoromethylpenicillanic acid; 6β-chloromethylpenicillanic acid; 6β-bromomethylpenicillanic acid; 6β-bromomethylpenicillanic acid; 6β-fluoromethylpenicillanic acid sulfoxide; 6β-chloromethylpenicillanic acid sulfoxide; 6β-bromomethylpenicillanic acid sulfoxide; 6β-fluoromethylpenicillanic acid sulfone; 6β-chloromethylpenicillanic acid sulfone; and 6β-bromomethylpenicillanic acid sulfone.

EXAMPLE 79

6β-Chloromethylpenicillanic Acid

A. 6β-hydroxymethylpenicillanic acid dimethoxyphosphine ester

To a solution of 2.31 g. of 6β-hydroxymethylpenicillanic acid in 40 ml. of methylene chloride is added 1.08 g. of triethylamine, and the solution is treated with 1.28 g. of dimethoxychlorophosphine and allowed to stir for 30 min. The solvent is removed in vacuo and the residue treated with 125 ml. of dry diethyl ether. The insoluble triethylamine hydrochloride is filtered and the ether removed under reduced pressure to provide the desired intermediate.

B. 6β-chloromethylpenicillanic acid dimethoxyphosphine ester

To 5 ml. of carbon tetrachloride containing 1.29 g. of 6β-hydroxymethylpenicillanic acid dimethoxyphosphine ester is added 1.88 g. of triphenylphosphine, and the resulting solution allowed to stir at room temperature for 3 hrs. The reaction mixture is treated with diethyl ether (75 ml.) and the resulting slurry is filtered and chromatographed on silica gel. The fractions containing the desired material are combined and concentrated in vacuo to give the intermediate.

C. 6β-chloropenicillanic acid

The above residual material is dissolved in 10 ml. of ethyl acetate-water and the pH adjusted to 5. After stirring at room temperature for 20 min. the organic layer is separated, dried over magnesium sulfate and concentrated to dryness to give the desired product.

EXAMPLE 80

A.

Starting with appropriate 6β-hydroxypenicillanic acid, sulfoxide or sulfone and employing the procedure of Example 79A, the following compounds are prepared:

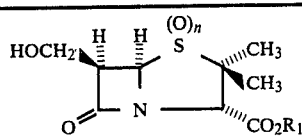

| n | $R_1$ |
|---|---|
| 0 | $P(C_6H_5)_2$ |
| 0 | $P(O-n-C_3H_7)_2$ |
| 0 | $P(C_2H_5)_2$ |
| 0 | $P(n-C_3H_7)_2$ |
| 0 | $P(CH_3)C_6H_5$ |
| 1 | $P(OCH_3)_2$ |
| 1 | $P)OC_2H_5)C_6H_5$ |
| 1 | $P(OC_2H_5)_2$ |
| 1 | $P(C_6H_5)_2$ |
| 2 | $P(OCH_3)_2$ |
| 2 | $P(C_2H_5)C_6H_5$ |
| 2 | $P(OC_2H_5)CH_3$ |

B.

Using the esters from Examples 80A and employing the indicated procedures, the following intermediates are synthesized:

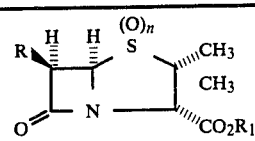

| R | n | $R_1$ | Procedure |
|---|---|---|---|
| $ClCH_2-$ | 0 | $P(OCH_3)_2$ | Example 66 |
| $ClCH_2-$ | 0 | $P(C_6H_5)_2$ | Example 66 |
| $ClCH_2-$ | 0 | $P(C_2H_5)_2$ | Example 66 |
| $BrCH_2-$ | 0 | $P(O-n-C_3H_7)_2$ | Example 67 |

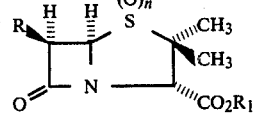

| R | n | $R_1$ | Procedure |
|---|---|---|---|
| $BrCH_2-$ | 0 | $P(n-C_3H_7)_2$ | Example 67 |
| $BrCH_2-$ | 0 | $P(CH_3)C_6H_5$ | Example 67 |
| $ClCH_2-$ | 1 | $P(OCH_3)_2$ | Example 66 |
| $ClCH_2-$ | 1 | $P(C_6H_5)_2$ | Example 66 |
| $BrCH_2-$ | 1 | $P(OC_2H_5)C_6H_5$ | Example 67 |
| $BrCH_2-$ | 1 | $P(OC_2H_5)_2$ | Example 67 |
| $ClCH_2-$ | 2 | $P(OCH_3)_2$ | Example 66 |
| $ClCH_2-$ | 2 | $P(OC_2H_5)CH_3$ | Example 66 |
| $BrCH_2-$ | 2 | $P(C_2H_5)C_6H_5$ | Example 67 |

C.

Employing the above esters from Example 80B, and using the procedure of Example 79C, the following compounds are synthesized:

6β-chloromethylpenicillanic acid, 6β-chloromethylpenicillanic acid sulfoxide; 6β-chloromethylpenicillanic acid sulfone; 6β-bromomethylpenicillanic acid; 6β-bromomethylpenicillanic acid sulfoxide; and 6β-bromomethylpenicillanic acid sulfone.

EXAMPLE 81

6β-Fluoromethylpenicillanic Acid

To a solution of 40 ml. of dry methylene chloride containing 1.6 g. of diethylaminosulfurtrifluoride at $-78°$ C. and under a nitrogen atmosphere is added 3.23 g. of 6β-hydroxymethylpenicillanic acid dimethoxyphosphine ester (Example 79A) and 1.6 ml. of pyridine in 10 ml. of methylene chloride. The reaction mixture is stirred at $-78°$ C. for 45 min. and is then allowed to warm to room temperature. The reaction mixture is then treated with 100 ml. of water and the pH adjusted to 5.0 with 6 N hydrochloric acid. The organic phase is separated, dried over magnesium sulfate and concentrated under reduced pressure to dryness. The final product is purified by chromatographing on silica gel.

EXAMPLE 82

6β-chloromethylpenicillanic acid

A. 3,5-di-t-butyl-4-hydroxybenzyl 6β-hydroxy methylpenicillanate

To a solution of 2.3 g. of 6β-hydroxymethylpenicillanic acid in 200 ml. of dry methylene chloride is added 1.0 g. of triethylamine and the resulting solution cooled to 0°-5° C. Ethyl chloroformate (1.1 g.) is added portionwise to the reaction mixture over a period of 15 min. The reaction is maintained at 0° C. for 30 min. and is then treated with 2.36 g. of 3,5-di-t-butylbenzyl alcohol. After stirring in the cold for 2 hrs. the reaction mixture is allowed to warm to room temperature. Water (75 ml.) is added to the reaction mixture and the organic phase is separated, dried over sodium sulfate and concentrated in vacuo to give the desired compound.

B. 3,5-t-butyl-4-hydroxybenzyl 6β-chloromethylpenicillanate

A solution of 1.7 g. of 3,5-di-t-butyl-4-hydroxybenzyl 6β-hydroxymethylpenicillanate and 1.88 g. of triphenylphosphine in 5 ml. of carbon tetrachloride is allowed to stir at room temperature for 2 hrs. The reaction mixture is treated with diethyl ether and the resulting slurry filtered.

C. 6β-chloromethylpenicillanic acid

The residual solids are dissolved in tetrahydrofuran-water (1:1) and the pH carefully adjusted to 8.0. After stirring for 20 min. 100 ml. of ethyl acetate is added and the pH adjusted to 7.0. The ethyl acetate is separated and fresh ethyl acetate is added to the aqueous and the pH adjusted to 1.5 with 6 N hydrochloric acid. The organic phase is separated, dried over magnesium sulfate and concentrated to give the desired product.

EXAMPLE 83

A.

Starting with the requisite 6β-hydroxymethylpenicillanic acid sulfoxide and sulfone and using the procedure of Example 82A, 3,5-di-t-butyl-4-hydroxybenzyl 6β-hydroxymethylpenicillanate sulfoxide and 3,5-di-t-butyl-4-hydroxybenzyl 6β-hydroxymethylpenicillanate sulfone are prepared.

C.

Using the appropriate esters from Examples 82A nd 83A and employing the indicated procedure the following intermediates are synthesized:

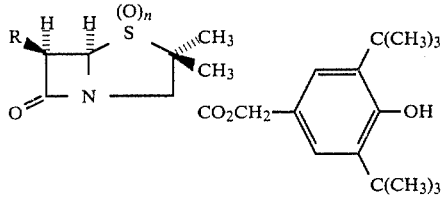

| R | n | Procedure |
|---|---|-----------|
| $FCH_2-$ | 0 | Example 65 |
| $BrCH_2-$ | 0 | Example 67 |
| $FCH_2-$ | 1 | Example 65 |
| $ClCH_2-$ | 1 | Example 66 |
| $BrCH_2$ | 1 | Example 67 |
| $FCH_2-$ | 2 | Example 65 |
| $ClCH_2-$ | 2 | Example 66 |
| $BrCH_2-$ | 2 | Example 67 |

C.

Starting with the esters of Example 83B and using the procedure of Example 82C, the following final products are prepared:

6β-fluoromethylpencillanic acid; 6β-bromomethylpenicillanic acid; 6β-fluoromethylpenicillanic acid sulfoxide; 6β-chloromethylpenicillanic acid sulfoxide; 6β-bromomethylpenicillanic acid sulfoxide; 6β-fluoromethylpenicillanic acid sulfone; 6β-chloromethylpenicillanic acid sulfone; and 6β-bromomethylpenicillanic acid sulfone.

We claim:

1. A proceess for the preparation of a compound selected from those of the formula

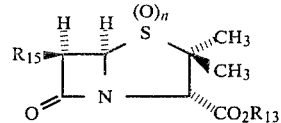

wherein $R_{15}$ is selected from the group consisting of fluoro, chloro, bromo, iodo, alkoxy having from one to four carbon atoms and alkylthio having from one to four carbon atoms; n is an integer of from 0 to 2; and $R_{13}$ is selected from the group consisting of hydrogen and ester-forming residues readily hydrolyzable in vivo which comprises reacting a compound of the formula

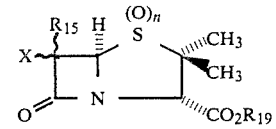

wherein X is selected from the group consisting of chloro, bromo and iodo; and $R_{19}$ is selected from the group consisting of ester-forming residues readily hydrolyzable in vivo and conventional penicillin carboxy protecting groups, with an organotin monohydride at about 0°–110° C., followed by removal of $R_{19}$ when it is a conventional penicillin carboxy protecting group, with the proviso that when said $R_{19}$ is a conventional penicillin carboxy protecting group n is an integer of from 0 to 1.

2. The process of claim 1, wherein the organotin monohydride is of the formula $$HSnR_{16}R_{17}R_{18}$$

wherein $R_{16}$, $R_{17}$ and $R_{18}$ are each selected from the group consisting of alkyl having from one to five carbon atoms, phenyl and benzyl.

3. The process of claim 2, wherein $R_{19}$ is a conventional penicillin carboxy protecting group selected from the group consisting of
 (a) $-PR_2R_3$ wherein $R_2$ and $R_3$ are each selected from the group consisting of alkyl having from one to three carbon atoms, alkoxy having from one to three carbon atoms and phenyl;
 (b) 3,5-di-t-butyl-4-hydroxybenzyl;
 (c) $-CH_2-Y$ wherein Y is selected from the group consisting of $-C(O)R_4$ wherein $R_4$ is phenyl or alkyl having from one to three carbon atoms, cyano and carboalkoxy having from two to four carbon atoms;
 (d) $-N=CH-R_5$ wherein $R_5$ is selected from the group consisting of phenyl and alkyl having from one to three carbon atoms;
 (e) $-CH(COCH_3)CO_2R_6$ wherein $R_6$ is alkyl having from one to four carbon atoms;
 (f) $-CR_7R_8R_9$ wherein $R_7$ and $R_8$ are each selected from the group consisting of hydrogen, phenyl and methyl and $R_9$ is selected from the group consisting of phenyl 4-methoxyphenyl and methyl, with the proviso that when $R_7$ and $R_8$ are each methyl, $R_9$ is methyl;
 (g) $-Si(CH_3)_3$ and $-Si(CH_3)_2t-C_4H_9$; and
 (h) $-SnR_{16}R_{17}R_{18}$ wherein $R_{16}$, $R_{17}$ and $R_{18}$ are each selected from the group consisting of alkyl having from one to five carbon atoms, phenyl and benzyl.

4. The process of claim 3, wherein $R_{19}$ is a conventional penicillin carboxy protecting group —$SnR_{16}R_{17}R_{18}$ wherein $R_{16}$, $R_{17}$ and $R_{18}$ are each n-butyl, $R_{15}$ and X are each bromo, n is 0 and the organotin monohydride is tri-n-butyltin hydride.

5. The process of claim 4, wherein the conventional penicillin carboxy protecting group is removed by aqueous hydrolysis.

6. The process of claim 3, wherein $R_{19}$ is a conventional penicillin carboxy protecting group —$SnR_{16}R_{17}R_{18}$ wherein $R_{16}$, $R_{17}$ and $R_{18}$ are each n-butyl, $R_{15}$ is chloro, X is iodo, n is 0 and the organotin monohydride is tri-n-butyltin hydride.

7. The process of claim 6, wherein the conventional penicillin carboxy protecting group is removed by aqueous hydrolysis.

8. The process of claim 3, wherein $R_{19}$ is a conventional penicillin carboxy protecting group —$Si(CH_3)_3$, $R_{15}$ and X are each bromo, n is 0 and the organotin monohydride is tri-n-butyltin hydride.

9. The process of claim 8, wherein the conventional penicillin carboxy protecting group is removed by aqueous hydrolysis.

10. The process of claim 3, wherein $R_{19}$ is a convention penicillin carboxy protecting group —$CR_7R_8R_9$ wherein $R_7$ and $R_8$ are each hydrogen and $R_9$ is 4-methoxyphenyl, $R_{15}$ and X are each iodo, n is 0 and the organotin monohydride is tri-n-butyltin hydride.

11. The process of claim 3, wherein $R_{19}$ is a conventional penicillin carboxy protecting group —$Si(CH_3)_3$, $R_{15}$ is chloro and X is iodo, n is 0 and the organotin monohydride is tri-n-butyltin hydride.

12. The process of claim 11, wherein the conventional penicillin carboxy protecting group is removed by aqueous hydrolysis.

13. The process of claim 10, wherein the conventional pencillin carboxy protecting group is removed by hydrolysis.

14. The process of claim 2, wherein $R_{19}$ is an ester-forming residue readily hydrolyzable in vivo selected from the group consisting of alkanoyloxymethyl having from 3 to 6 carbon atoms, 1-(alkanoyloxy)ethyl having from 4 to 7 carbon atoms, 1-methyl-1-(alkanoyloxy)ethyl having from 5 to 8 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

15. The process of claim 14, wherein $R_{19}$ is pivaloyloxymethyl, $R_{15}$ and X are each bromo, n is 0 and the organotin monohydride is triphenyltin hydride.

16. The process of claim 14, wherein $R_{19}$ is pivaloyloxymethyl, $R_{15}$ is chloro, X is bromo, n is 0 and the organotin monohydride is tri-n-butyltin hydride.

17. The process of claim 14, wherein $R_{19}$ is pivaloyloxymethyl, $R_{15}$ and X are each iodo, n is 0 and the organotin monohydride is tri-n-butyltin hydride.

18. A process for the preparation of a compound selected from those of the formula:

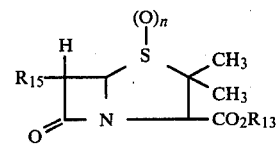

wherein $R_{15}$ is selected from the group consisting of fluoro, chloro, bromo, iodo, alkoxy having from one to four carbon atoms and alkylthio having from one to four carbon atoms; n is an integer from 0 to 2; $R_{13}$ is an ester group which comprises reacting a compound of the formula:

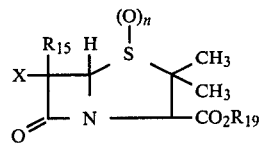

wherein X is selected from the group consisting of chloro, bromo and iodo; $R_{19}$ is an ester group with a tri-alkyl tin hydride.

* * * * *